United States Patent
Lee et al.

(10) Patent No.: US 9,193,707 B2
(45) Date of Patent: Nov. 24, 2015

(54) TETRAHYDROISOQUINOLIN-2-YL-(QUINAZOLIN-4-YL)METHANONE COMPOUNDS

(71) Applicants: Young Bok Lee, Clarksburg, MD (US); Jae Min Kim, Clarksburg, MD (US); Deog Joong Kim, Rockville, MD (US); Chang-Ho Ahn, Potomac, MD (US)

(72) Inventors: Young Bok Lee, Clarksburg, MD (US); Jae Min Kim, Clarksburg, MD (US); Deog Joong Kim, Rockville, MD (US); Chang-Ho Ahn, Potomac, MD (US)

(73) Assignee: Rexahn Pharmaceuticals, Inc., Rockville, MD (US)

( * ) Notice: Subject to any disclaimer, the term of this patent is extended or adjusted under 35 U.S.C. 154(b) by 0 days.

(21) Appl. No.: 14/212,031

(22) Filed: Mar. 14, 2014

(65) Prior Publication Data

US 2014/0275129 A1  Sep. 18, 2014

Related U.S. Application Data

(60) Provisional application No. 61/788,740, filed on Mar. 15, 2013.

(51) Int. Cl.
*C07D 401/06* (2006.01)
*C07D 417/14* (2006.01)
*C07D 401/14* (2006.01)

(52) U.S. Cl.
CPC ............ *C07D 401/06* (2013.01); *C07D 401/14* (2013.01); *C07D 417/14* (2013.01)

(58) Field of Classification Search
CPC ... A01N 43/54; A61K 31/517; C07D 239/72; C07D 401/00
USPC ............. 514/266.1, 266.2; 544/283, 284
See application file for complete search history.

(56) References Cited

U.S. PATENT DOCUMENTS

2007/0259871 A1* 11/2007 Chessari et al. ........... 514/235.2

FOREIGN PATENT DOCUMENTS

WO   WO-2009/010139      1/2009
WO   WO 2009/010139  *   1/2009  ............ C07D 239/72

OTHER PUBLICATIONS

El-Azab et al., "Design, synthesis and biological evaluation of novel quinazoline derivatives as potential antitumor agents: Molecular docking study", European Journal of Medicinal Chemistry, 2010, pp. 4188-4198, vol. 45.
International Search Report of International Application No. PCT/US2014/028165.

* cited by examiner

*Primary Examiner* — Paul V Ward
(74) *Attorney, Agent, or Firm* — Venable LLP; Keith G. Haddaway; Annette K. Kwok

(57) ABSTRACT

Tetrahydroisoquinolin-2-yl-(quinazolin-4-yl)methanone derivatives represented by formula (I), pharmacologically acceptable salts thereof, and compositions containing such compounds are described. Methods for treating hyperproliferative disorders by administering the compounds are also described. 1,2,3,4-tetrahydroisoquinoline derivatives for making tetrahydroisoquinolin-2-yl-(quinazolin-4-yl)methanone compounds are also described.

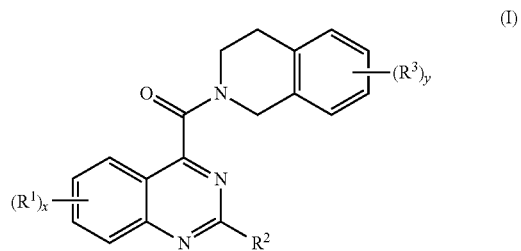

(I)

20 Claims, 1 Drawing Sheet

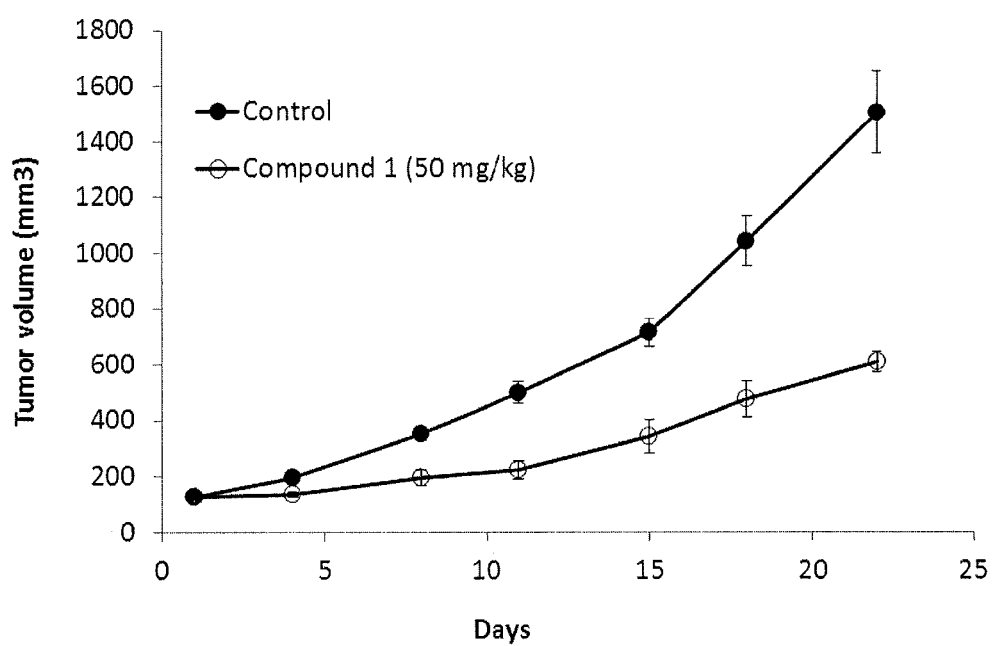

TETRAHYDROISOQUINOLIN-2-YL-(QUINAZOLIN-4-YL)METHANONE COMPOUNDS

CLAIM OF PRIORITY

This application claims priority to U.S. Application No. 61/788,740, filed Mar. 15, 2013, which is incorporated by reference in its entirety.

TECHNICAL FIELD

The present invention relates to tetrahydroisoquinolin-2-yl-(quinazolin-4-yl)methanone compounds and pharmacologically acceptable salts thereof, compositions containing such compounds and therapeutic methods for the treatment of hyperproliferative disorders, including cancers, by administering tetrahydroisoquinolin-2-yl-(quinazolin-4-yl) methanone compounds. This invention also relates methods of making tetrahydroisoquinolin-2-yl-(quinazolin-4-yl) methanone compounds, and to 1,2,3,4-tetrahydroisoquinoline compounds useful in making tetrahydroisoquinolin-2-yl-(quinazolin-4-yl)methanone compounds.

BACKGROUND

Chemotherapeutics kill tumor cells by interfering with various stages of the cell division process. There are a number of classes of chemotherapeutics including alkylating agents (e.g., cyclophosphamide, carmustine, cisplatin), antimetabolites (e.g., methotrexate, 5-FU, gemcitabine), cytotoxic antibiotics (e.g., doxorubicin, mitomycin) and plant derivatives (e.g., paclitaxel, vincristine, etoposide). Chemotherapy is also used as a primary treatment for leukemias, other blood cancers, and inoperable or metastatic solid cancers.

Current chemotherapeutic agents suffer several problems, including limited efficacy, debilitating adverse side effects and development of multidrug resistance.

SUMMARY

Tetrahydroisoquinolin-2-yl-(quinazolin-4-yl) methanone compounds are useful for the treatment of hyperproliferative disorders, including tumors, such as breast tumors, prostate tumors, colon tumors, ovary tumors, kidney tumors, pancreas tumors, glioblastoma, stomach tumors, lung tumors, liver tumors, cervix and melanoma.

In one aspect, a compound of formula (I):

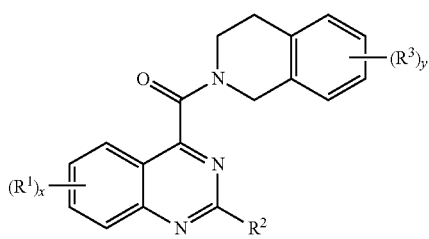

(I)

Each $R^1$, independently, can be hydrogen, halogen, or —O—$R^4$. $R^2$ can be —$(CR^aR^b)_z$—$R^5$. Each $R^3$, independently, can be hydrogen, halogen, —$N(R^4)_2$, —O—$R^4$, alkyl, alkoxy, alkenyl, alkynyl, cycloalkyl, heterocyclyl, aryl, or heteroaryl.

Each $R^a$, independently, can be hydrogen, halogen, hydroxy, alkyl, alkoxy, alkenyl, alkynyl, cycloalkyl, heterocyclyl, aryl, or heteroaryl. Each $R^b$, independently, can be hydrogen, halogen, hydroxy, alkyl, alkoxy, alkenyl, alkynyl, cycloalkyl, heterocyclyl, aryl, or heteroaryl.

Each $R^4$, independently, can be hydrogen or $C_1$-$C_6$ alkyl. $R^5$ can be hydrogen, halo, alkyl, hydroxy, alkyl, alkoxy, alkenyl, alkynyl, cycloalkyl, heterocyclyl, —N($R^4$)CO—$R^4$ or Ar.

Ar can be aryl or heteroaryl, wherein each of aryl and heteroaryl can be optionally substituted by one to five substituents independently selected from hydrogen, halogen, —$R^4$, —$N(R^4)_2$, nitro, —$(CH_2)_n$—NHCO—$R^4$, —O—$R^4$, alkyl, alkenyl, alkynyl, cycloalkyl, heterocyclyl, aryl, or heteroaryl.

n can be 0, 1, 2, or 3. x can be 0, 1, 2, 3, or 4. y can be 0, 1, 2, 3, or 4. z can be 0, 1, 2, 3, 4, 5, or 6.

A compound of formula (I) can be in the form of a pharmaceutically acceptable salt.

In some embodiment, $R^2$ can be —$(CR^aR^b)_z$—$N(R^4)$CO—$R^4$, or Ar. $R^2$ can be Ar optionally substituted by one to five substituents independently selected from hydrogen, halogen, —$R^4$, —$N(R^4)_2$, and —O—$R^4$. $R^2$ can be aryl optionally substituted by one to five substituents independently selected from hydrogen, halogen, —$R^4$, —$N(R^4)_2$, and —O—$R^4$. $R^2$ can be heteroaryl optionally substituted by one to five substituents independently selected from hydrogen, halogen, —$R^4$, —$N(R^4)_2$, and —O—$R^4$.

In some embodiments, x can be 1 or 2 and each $R^1$, independently, can be hydrogen, halogen or —O$R^4$. y can be 1 or 2 and each $R^3$, independently, is hydrogen, halogen, —$R^4$, —$N(R^4)_2$, or —O$R^4$.

In some embodiments, the compound has the structure of formula (II):

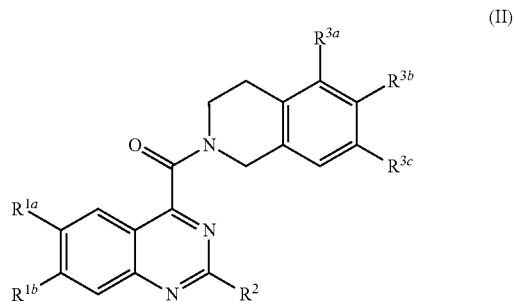

(II)

Each of $R^{1a}$ and $R^{1b}$, independently, can be H, halogen, hydroxy, alkyl, haloalkyl, or alkoxy.

$R^2$ can be acetamidoethyl or Ar, wherein Ar is selected from phenyl and heteroaryl, wherein each of phenyl and heteroaryl can be optionally substituted by one to five substituents independently selected from hydrogen, halogen, —$R^4$, —$N(R^4)_2$, nitro, —O—$R^4$, —NHCO—$CH_3$, —$CH_2$—NHCO—$CH_3$, and trifluoromethyl. Each of $R^{3a}$, $R^{3b}$, and $R^{3c}$, independently, can be H, halogen, hydroxy, alkyl, alkoxy, or —$N(R^4)_2$.

In some embodiments, each of $R^{1a}$ and $R^{1b}$, independently, can be hydrogen, halogen, or alkoxy; $R^2$ can be acetamidoethyl, 4-pyrimidinyl, 4-thiazolyl, 3-pyridinyl, or phenyl optionally substituted by 1 to 3 substituents independently selected from hydrogen, halogen, nitro, trifluoromethyl, amino, dimethylamino, —NHCO—$CH_3$, —$CH_2$—NHCO—$CH_3$, methyl, or methoxy; each of $R^{3a}$, $R^{3b}$, and $R^{3c}$, independently, can be hydrogen, halogen, hydroxyl, dimethylamino, methyl or methoxy; and y can be 1 or 2.

R$^{3c}$ can be H. Each R$^1$ can be independently hydrogen or halogen; R$^2$ can be phenyl, 4-nitrophenyl, 4-aminophenyl, 3-fluorophenyl, 4-fluorophenyl, 2,4-difluorophenyl, 4-methylphenyl, 3-methoxyphenyl, 4-methoxyphenyl, 4-chlorophenyl, 4-(dimethylamino)phenyl, 3-(trifluoromethyl)phenyl, 4-(trifluoromethyl)phenyl, 4-acetamidophenyl, 4-pyrimidinyl, 4-thiazolyl or 3-pyridinyl; R$^{3a}$ can be hydroxy or methoxy; R$^{3b}$ can be methoxy, methyl, or dimethylamino; and R$^{3c}$ can be hydrogen.

Each R$^4$, independently, can be hydrogen or C$_1$-C$_6$ alkyl.

In some embodiments, the compound has an IC$_{50}$ of not greater than 1.0 µM, or not greater than 0.1 µM, with respect to at least one cell line for a tumor selected from breast tumors, prostate tumors, colon tumors, ovary tumors, kidney tumors, pancreas tumors, glioblastoma, stomach tumors, lung tumors, liver tumors, cervix and melanoma. The cell line can be selected from human MDA-MB-231, PC3, HCT116, OVCAR-3, Caki-1, PANC-1, U251, MKN-45, A549, HepG2, HeLa and SK-MEL-28.

In another aspect, a compound selected from the group consisting of:

2-[[2-(4-fluorophenyl)quinazolin-4-yl]carbonyl]-5-hydroxy-6-methoxy-1,2,3,4-tetrahydroisoquinoline; 2-[[2-(4-fluorophenyl)quinazolin-4-yl]carbonyl]-5,6-dihydroxy-1,2,3,4-tetrahydroisoquinoline; 2-[[2-(4-fluorophenyl)quinazolin-4-yl]carbonyl]-5,6-dimethoxy-1,2,3,4-tetrahydroisoquinoline; 2-[[2-(4-fluorophenyl)quinazolin-4-yl]carbonyl]-5-hydroxy-6-dimethylamino-1,2,3,4-tetrahydroisoquinoline; 2-[[2-(4-fluorophenyl)quinazolin-4-yl]carbonyl]-5-hydroxy-6-methyl-1,2,3,4-tetrahydroisoquinoline; 2-[[2-(4-fluorophenyl)quinazolin-4-yl]carbonyl]-5-methoxy-1,2,3,4-tetrahydroisoquinoline; 2-[[2-(4-fluorophenyl)quinazolin-4-yl]carbonyl]-6-methoxy-1,2,3,4-tetrahydroisoquinoline; 2-[[2-(4-fluorophenyl)quinazolin-4-yl]carbonyl]-5,7-dimethoxy-1,2,3,4-tetrahydroisoquinoline; 2-[[2-(4-fluorophenyl)quinazolin-4-yl]carbonyl]-5-hydroxy-1,2,3,4-tetrahydroisoquinoline; 2-[[2-(4-fluorophenyl)quinazolin-4-yl]carbonyl]-5-fluoro-1,2,3,4-tetrahydroisoquinoline; 2-[[2-(4-fluorophenyl)quinazolin-4-yl]carbonyl]-6-fluoro-1,2,3,4-tetrahydroisoquinoline; 2-[[2-(4-methylphenyl)quinazolin-4-yl]carbonyl]-5-hydroxy-6-methoxy-1,2,3,4-tetrahydroisoquinoline; 2-[[2-(4-methylphenyl)quinazolin-4-yl]carbonyl]-5,6-dihydroxy-1,2,3,4-tetrahydroisoquinoline; 2-[[2-(4-methylphenyl)quinazolin-4-yl]carbonyl]-5,6-dimethoxy-1,2,3,4-tetrahydroisoquinoline; 2-[[2-(4-methylphenyl)quinazolin-4-yl]carbonyl]-5-hydroxy-6-dimethylamino-1,2,3,4-tetrahydroisoquinoline; 2-[[2-(4-methylphenyl)quinazolin-4-yl]carbonyl]-5-hydroxy-6-methyl-1,2,3,4-tetrahydroisoquinoline; 2-[[2-phenylquinazolin-4-yl]carbonyl]-5-hydroxy-6-methoxy-1,2,3,4-tetrahydroisoquinoline; 2-[[2-phenylquinazolin-4-yl]carbonyl]-5,6-dihydroxy-1,2,3,4-tetrahydroisoquinoline; 2-[[2-phenylquinazolin-4-yl]carbonyl]-5,6-dimethoxy-1,2,3,4-tetrahydroisoquinoline; 2-[[2-phenylquinazolin-4-yl]carbonyl]-5-hydroxy-6-dimethylamino-1,2,3,4-tetrahydroisoquinoline; 2-[[2-phenylquinazolin-4-yl]carbonyl]-5-hydroxy-6-methyl-1,2,3,4-tetrahydroisoquinoline; 2-[[2-(4-methoxyphenyl)quinazolin-4-yl]carbonyl]-5-hydroxy-6-methoxy-1,2,3,4-tetrahydroisoquinoline; 2-[[2-(4-methoxyphenyl)quinazolin-4-yl]carbonyl]-5,6-dihydroxy-1,2,3,4-tetrahydroisoquinoline; 2-[[2-(4-methoxyphenyl)quinazolin-4-yl]carbonyl]-5,6-dimethoxy-1,2,3,4-tetrahydroisoquinoline; 2-[[2-(4-methoxyphenyl)quinazolin-4-yl]carbonyl]-5-hydroxy-6-dimethylamino-1,2,3,4-tetrahydroisoquinoline; 2-[[2-(4-methoxyphenyl)quinazolin-4-yl]carbonyl]-5-hydroxy-6-methyl-1,2,3,4-tetrahydroisoquinoline; 2-[[2-(4-chlorophenyl)quinazolin-4-yl]carbonyl]-5-hydroxy-6-methoxy-1,2,3,4-tetrahydroisoquinoline; 2-[[2-(4-chlorophenyl)quinazolin-4-yl]carbonyl]-5,6-dihydroxy-1,2,3,4-tetrahydroisoquinoline; 2-[[2-(4-chlorophenyl)quinazolin-4-yl]carbonyl]-5,6-dimethoxy-1,2,3,4-tetrahydroisoquinoline; 2-[[2-(4-chlorophenyl)quinazolin-4-yl]carbonyl]-5-hydroxy-6-dimethylamino-1,2,3,4-tetrahydroisoquinoline; 2-[[2-(4-chlorophenyl)quinazolin-4-yl]carbonyl]-5-hydroxy-6-methyl-1,2,3,4-tetrahydroisoquinoline; 2-[[2-(4-(dimethylamino)phenyl)quinazolin-4-yl]carbonyl]-5-hydroxy-6-methoxy-1,2,3,4-tetrahydroisoquinoline; 2-[[2-(4-(dimethylamino)phenyl)quinazolin-4-yl]carbonyl]-5,6-dihydroxy-1,2,3,4-tetrahydroisoquinoline; 2-[[2-(4-(dimethylamino)phenyl)quinazolin-4-yl]carbonyl]-5,6-dimethoxy-1,2,3,4-tetrahydroisoquinoline; 2-[[2-(4-(dimethylamino)phenyl)quinazolin-4-yl]carbonyl]-5-hydroxy-6-dimethylamino-1,2,3,4-tetrahydroisoquinoline; 2-[[2-(4-(dimethylamino)phenyl)quinazolin-4-yl]carbonyl]-5-hydroxy-6-methyl-1,2,3,4-tetrahydrosoquinoline; 2-[[2-(4-(trifluoromethyl)phenyl)quinazolin-4-yl]carbonyl]-5-hydroxy-6-methoxy-1,2,3,4-tetrahydroisoquinoline; 2-[[2-(4-(trifluoromethyl)phenyl)quinazolin-4-yl]carbonyl]-5,6-dihydroxy-1,2,3,4-tetrahydroisoquinoline; 2-[[2-(4-(trifluoromethyl)phenyl)quinazolin-4-yl]carbonyl]-5,6-dimethoxy-1,2,3,4-tetrahydroisoquinoline; 2-[[2-(4-(trifluoromethyl)phenyl)quinazolin-4-yl]carbonyl]-5-hydroxy-6-dimethylamino-1,2,3,4-tetrahydroisoquinoline; 2-[[2-(4-(trifluoromethyl)phenyl)quinazolin-4-yl]carbonyl]-5-hydroxy-6-methyl-1,2,3,4-tetrahydroisoquinoline; 2-[[2-(3-fluorophenyl)quinazolin-4-yl]carbonyl]-5-hydroxy-6-methoxy-1,2,3,4-tetrahydroisoquinoline; 2-[[2-(3-fluorophenyl)quinazolin-4-yl]carbonyl]-5,6-dihydroxy-1,2,3,4-tetrahydroisoquinoline; 2-[[2-(3-fluorophenyl)quinazolin-4-yl]carbonyl]-5,6-dimethoxy-1,2,3,4-tetrahydroisoquinoline; 2-[[2-(3-fluorophenyl)quinazolin-4-yl]carbonyl]-5-hydroxy-6-dimethylamino-1,2,3,4-tetrahydroisoquinoline; 2-[[2-(3-fluorophenyl)phenyl)quinazolin-4-yl]carbonyl]-5-hydroxy-6-methyl-1,2,3,4-tetrahydroisoquinoline; 2-[[2-(3-methoxylphenyl)quinazolin-4-yl]carbonyl]-5-hydroxy-6-methoxy-1,2,3,4-tetrahydroisoquinoline; 2-[[2-(3-methoxylphenyl)quinazolin-4-yl]carbonyl]-5,6-dihydroxy-1,2,3,4-tetrahydroisoquinoline; 2-[[2-(3-methoxylphenyl)quinazolin-4-yl]carbonyl]-5,6-dimethoxy-1,2,3,4-tetrahydroisoquinoline; 2-[[2-(3-methoxylphenyl)quinazolin-4-yl]carbonyl]-5-hydroxy-6-dimethylamino-1,2,3,4-tetrahydroisoquinoline; 2-[[2-(3-methoxylphenyl)phenyl)quinazolin-4-yl]carbonyl]-5-hydroxy-6-methyl-1,2,3,4-tetrahydroisoquinoline; 2-[[2-(3-(trifluoromethyl)phenyl)quinazolin-4-yl]carbonyl]-5-hydroxy-6-methoxy-1,2,3,4-tetrahydroisoquinoline; 2-[[2-(3-(trifluoromethyl)phenyl)quinazolin-4-yl]carbonyl]-5,6-dihydroxy-1,2,3,4-tetrahydroisoquinoline; 2-[[2-(3-(trifluoromethyl)phenyl)quinazolin-4-yl]carbonyl]-5,6-dimethoxy-1,2,3,4-tetrahydroisoquinoline; 2-[[2-(3-(trifluoromethyl)phenyl)quinazolin-4-yl]carbonyl]-5-hydroxy-6-dimethylamino-1,2,3,4-tetrahydroisoquinoline; 2-[[2-(3-(trifluoromethyl)phenyl)quinazolin-4-yl]carbonyl]-5-hydroxy-6-methyl-1,2,3,4-tetrahydroisoquinoline; 2-[[2-(2,4-difluorophenyl)quinazolin-4-yl]carbonyl]-5-hydroxy-6-methoxy-1,2,3,4-tetrahydroisoquinoline; 2-[[2-(2,4-difluorophenyl)quinazolin-4-yl]carbonyl]-5,6-dihydroxy-1,2,3,4-tetrahydroisoquinoline; 2-[[2-(2,4-difluorophenyl)quinazolin-4-yl]carbonyl]-5,6-dimethoxy-1,2,3,4-tetrahydroisoquinoline; 2-[[2-(2,4-difluorophenyl)quinazolin-4-yl]carbonyl]-5-hydroxy-6-dimethylamino-1,2, 3,4-tetrahydroisoquinoline; 2-[[2-(2,4-difluorophenyl)quinazolin-4-yl]carbonyl]-5-hydroxy-6-methyl-1,2,3,4-tetrahydroisoquinoline; 2-[[2-(4-acetamidophenyl)quinazolin-4-yl]carbonyl]-5-hydroxy-6-methoxy-1,2,3,4-tetrahydroisoquinoline; 2-[[2-(4-acetamidophenyl)quinazolin-4-yl]carbonyl]-5,6-dimethoxy-1,2,3,4-tetrahydroisoquinoline; 2-[[2-(4-acetamidophenyl)quinazolin-4-yl]carbonyl]-5-hydroxy-6-methyl-1,2,3,4-tetrahydroisoquinoline; 2-[[2-(4-(acetamidomethyl)phenyl)quinazolin-4-yl]carbonyl]-5-hydroxy-6-methoxy-1,2,3,4-tetrahydroisoquinoline; 2-[[2-(4-(acetamidomethyl)phenyl)quinazolin-4-yl]carbonyl]-5,6-dihydroxy-1,2,3,4-tetrahydroisoquinoline; 2-[[2-(4-(acetamidomethyl)phenyl)quinazolin-4-yl]carbonyl]-5,6-dimethoxy-1,2,3,4-tetrahydroisoquinoline; 2-[[2-(4-(acetamidomethyl)phenyl)quinazolin-4-yl]carbonyl]-5-hydroxy-6-dimethylamino-1,2,3,4-tetrahydroisoquinoline; 2-[[2-(4-(acetamidomethyl)phenyl)quinazolin-4-yl]carbonyl]-5-hydroxy-6-methyl-1,2,3,4-tetrahydroisoquinoline; 2-[[2-(4-pyrimidinyl)quinazolin-4-yl]carbonyl]-5-hydroxy-6-methoxy-1,2,3,4-tetrahydroisoquinoline; 2-[[2-(4-pyrimidinyl)quinazolin-4-yl]carbonyl]-5,6-dihydroxy-1,2,3,4-tetrahydroisoquinoline; 2-[[2-(4-pyrimidinyl)quinazolin-4-yl]carbonyl]-5,6-dimethoxy-1,2,3,4-tetrahydroisoquinoline; 2-[[2-(4-pyrimidinyl)quinazolin-4-yl]carbonyl]-5-hydroxy-6-methyl-1,2,3,4-tetrahydroisoquinoline; 2-[[2-(2-(acetamido)ethyl)quinazolin-4-yl]carbonyl]-5-hydroxy-6-methoxy-1,2,3,4-tetrahydroisoquinoline; 2-[[2-(2-(acetamido)ethyl)quinazolin-4-yl]carbonyl]-5,6-dihydroxy-1,2,3,4-tetrahydroisoquinoline; 2-[[2-(2-(acetamido)ethyl)quinazolin-4-yl]carbonyl]-5,6-dimethoxy-1,2,3,4-tetrahydroisoquinoline; 2-[[2-(2-(acetamido)ethyl)quinazolin-4-yl]carbonyl]-5-hydroxy-6-dimethylamino-1,2,3,4-tetrahydroisoquinoline; 2-[[2-(2-(acetamido)ethyl)quinazolin-4-yl]carbonyl]-5-hydroxy-6-methyl-1,2,3,4-tetrahydroisoquinoline; 2-[[2-(4-thiazolyl)quinazolin-4-yl]carbonyl]-5-hydroxy-6-methoxy-1,2,3,4-tetrahydroisoquinoline; 2-[[2-(4-thiazolyl)quinazolin-4-yl]carbonyl]-5,6-dihydroxy-1,2,3,4-tetrahydroisoquinoline; 2-[[2-(4-thiazolyl)quinazolin-4-yl]carbonyl]-5,6-dimethoxy-1,2,3,4-tetrahydroisoquinoline; 2-[[2-(4-thiazolyl)quinazolin-4-yl]carbonyl]-5-hydroxy-6-dimethylamino-1,2,3,4-tetrahydroisoquinoline; 2-[[2-(4-thiazolyl)quinazolin-4-yl]carbonyl]-5-hydroxy-6-methyl-1,2,3,4-tetrahydroisoquinoline; 2-[[2-(3-pyridinyl)quinazolin-4-yl]carbonyl]-5-hydroxy-6-methoxy-1,2,3,4-tetrahydroisoquinoline; 2-[[2-(3-pyridinyl)quinazolin-4-yl]carbonyl]-5,6-dihydroxy-1,2,3,4-tetrahydroisoquinoline; 2-[[2-(3-pyridinyl)quinazolin-4-yl]carbonyl]-5,6-dimethoxy-1,2,3,4-tetrahydroisoquinoline; 2-[[2-(3-pyridinyl)quinazolin-4-yl]carbonyl]-5-hydroxy-6-dimethylamino-1,2,3,4-tetrahydroisoquinoline; 2-[[2-(3-pyridinyl)quinazolin-4-yl]carbonyl]-5-hydroxy-6-methyl-1,2,3,4-tetrahydroisoquinoline; 2-[[2-(3,4,5-trimethoxyphenyl)quinazolin-4-yl]carbonyl]-5-hydroxy-6-methoxy-1,2,3,4-tetrahydroisoquinoline; 2-[[2-(3,4,5-trimethoxyphenyl)quinazolin-4-yl]carbonyl]-5-methoxy-1,2,3,4-tetrahydroisoquinoline; 2-[[2-(3,4,5-trimethoxyphenyl)quinazolin-4-yl]carbonyl]-6-methoxy-1,2,3,4-tetrahydroisoquinoline; 2-[[2-(3,4,5-trimethoxyphenyl)quinazolin-4-yl]carbonyl]-5,7-dimethoxy-1,2,3,4-tetrahydroisoquinoline; 2-[[2-(3,4,5-trimethoxyphenyl)quinazolin-4-yl]carbonyl]-5-hydroxy-1,2,3,4-tetrahydroisoquinoline; 2-[[2-(3,4,5-trimethoxyphenyl)quinazolin-4-yl]carbonyl]-6-fluoro-1,2,3,4-tetrahydroisoquinoline; 2-[[2-(4-nitrophenyl)quinazolin-4-yl]carbonyl]-5-hydroxy-6-methoxy-1,2,3,4-tetrahydroisoquinoline; 2-[[2-(4-aminophenyl)quinazolin-4-yl]carbonyl]-5-hydroxy-6-methoxy-1,2,3,4-tetrahydroisoquinoline; 2-[[6-fluoro-2-(4-fluorophenyl)quinazolin-4-yl]carbonyl]-5-hydroxy-6-methoxy-1,2,3,4-tetrahydroisoquinoline; 2-[[6-fluoro-2-(4-fluorophenyl)quinazolin-4-yl]carbonyl]-5-methoxy-1,2,3,4-tetrahydroisoquinoline; 2-[[6-fluoro-2-(4-fluorophenyl)quinazolin-4-yl]carbonyl]-6-methoxy-1,2,3,4-tetrahydroisoquinoline; 2-[[6-fluoro-2-(4-fluorophenyl)quinazolin-4-yl]carbonyl]-5,7-dimethoxy-1,2,3,4-tetrahydroisoquinoline; 2-[[6-fluoro-2-(4-fluorophenyl)quinazolin-4-yl]carbonyl]-5-hydroxy-1,2,3,4-tetrahydroisoquinoline; 2-[[6-fluoro-2-(4-fluorophenyl)quinazolin-4-yl]carbonyl]-6-fluoro-1,2,3,4-tetrahydroisoquinoline; 2-[[6-fluoro-2-(3,4,5-trimethoxyphenyl)quinazolin-4-yl]carbonyl]-5-hydroxy-6-methoxy-1,2,3,4-tetrahydroisoquinoline; 2-[[6-fluoro-2-(3,4,5-trimethoxyphenyl)quinazolin-4-yl]carbonyl]-5-methoxy-1,2,3,4-tetrahydroisoquinoline; 2-[[6-fluoro-2-(3,4,5-trimethoxyphenyl)quinazolin-4-yl]carbonyl]-6-methoxy-1,2,3,4-tetrahydroisoquinoline; 2-[[6-fluoro-2-(3,4,5-trimethoxyphenyl)quinazolin-4-yl]carbonyl]-5,7-dimethoxy-1,2,3,4-tetrahydroisoquinoline; 2-[[6-fluoro-2-(3,4,5-trimethoxyphenyl)quinazolin-4-yl]carbonyl]-5-hydroxy-1,2,3,4-tetrahydroisoquinoline; 2-[[6-fluoro-2-(3,4,5-trimethoxyphenyl)quinazolin-4-yl]carbonyl]-6-fluoro-1,2,3,4-tetrahydroisoquinoline; 2-[[6,7-dimethoxy-2-(4-fluorophenyl)quinazolin-4-yl]carbonyl]-5-hydroxy-6-methoxy-1,2,3,4-tetrahydroisoquinoline; 2-[[6,7-dimethoxy-2-(4-fluorophenyl)quinazolin-4-yl]carbonyl]-5-methoxy-1,2,3,4-tetrahydroisoquinoline; 2-[[6,7-dimethoxy-2-(4-fluorophenyl)quinazolin-4-yl]carbonyl]-6-methoxy-1,2,3,4-tetrahydroisoquinoline; 2-[[6,7-dimethoxy-2-(4-fluorophenyl)quinazolin-4-yl]carbonyl]-5,7-dimethoxy-1,2,3,4-tetrahydroisoquinoline; 2-[[6,7-dimethoxy-2-(4-fluorophenyl)quinazolin-4-yl]carbonyl]-5-hydroxy-1,2,3,4-tetrahydroisoquinoline; 2-[[6,7-dimethoxy-2-(4-fluorophenyl)quinazolin-4-yl]carbonyl]-6-fluoro-1,2,3,4-tetrahydroisoquinoline; 2-[[6,7-dimethoxy-2-(3,4,5-trimethoxyphenyl)quinazolin-4-yl]carbonyl]-5-hydroxy-6-methoxy-1,2,3,4-tetrahydroisoquinoline; 2-[[6,7-dimethoxy-2-(3,4,5-trimethoxyphenyl)quinazolin-4-yl]carbonyl]-5-methoxy-1,2,3,4-tetrahydroisoquinoline; 2-[[6,7-dimethoxy-2-(3,4,5-trimethoxyphenyl)quinazolin-4-yl]carbonyl]-6-methoxy-1,2,3,4-tetrahydroisoquinoline; 2-[[6,7-dimethoxy-2-(3,4,5-trimethoxyphenyl)quinazolin-4-yl]carbonyl]-5,7-dimethoxy-1,2,3,4-tetrahydroisoquinoline; 2-[[6,7-dimethoxy-2-(3,4,5-trimethoxyphenyl)quinazolin-4-yl]carbonyl]-5-hydroxy-1,2,3,4-tetrahydroisoquinoline; and 2-[[6,7-dimethoxy-2-(3,4,5-trimethoxyphenyl)quinazolin-4-yl]carbonyl]-6-fluoro-1,2,3,4-tetrahydroisoquinoline; or a pharmaceutically acceptable salt thereof.

In some embodiments the compound of formula (I) can be covalently bonded to a cell-specific targeting moiety, or a pharmaceutically acceptable salt thereof.

In another aspect, a method for treating a hyperproliferative disorder includes administering a compound of formula (I) to a subject in need thereof.

In some embodiments, the hyperproliferative disorder can include a tumor. The tumor can be selected from breast tumors, prostate tumors, colon tumors, ovary tumors, kidney tumors, pancreas tumors, glioblastoma, stomach tumors, lung tumors, liver tumors, cervix and melanoma.

In another aspect, a method of making a compound of formula (I), includes contacting a compound of formula (IV):

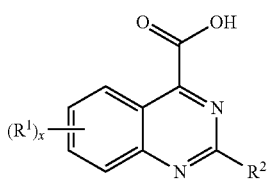

(IV)

with a compound of formula (IIIa), defined below.

In the compound of formula (IV), each $R^1$, independently, can be hydrogen, halogen, or —O—$R^4$. $R^2$ can be —$(CR^a R^b)_z$—$R^5$.

Each $R^a$, independently, can be hydrogen, halogen, hydroxy, alkyl, alkoxy, alkenyl, alkynyl, cycloalkyl, heterocyclyl, aryl, or heteroaryl. Each $R^b$, independently, can be hydrogen, halogen, hydroxy, alkyl, alkoxy, alkenyl, alkynyl, cycloalkyl, heterocyclyl, aryl, or heteroaryl.

Each $R^4$, independently, can be hydrogen or $C_1$-$C_6$ alkyl. $R^5$ can be hydrogen, halo, alkyl, hydroxy, alkyl, alkoxy, alkenyl, alkynyl, cycloalkyl, heterocyclyl, —N($R^4$)CO—$R^4$ or Ar.

Ar can be aryl or heteroaryl, wherein each of aryl and heteroaryl can be optionally substituted by one to five substituents independently selected from hydrogen, halogen, —$R^4$, —N($R^4$)$_2$, nitro, —$(CH_2)_n$—NHCO—$R^4$, —O—$R^4$, alkyl, alkenyl, alkynyl, cycloalkyl, heterocyclyl, aryl, or heteroaryl.

n can b 0, 1, 2, or 3. x can be 0, 1, 2, 3, or 4. z can be 0, 1, 2, 3, 4, 5, or 6.

$(R^1)_x$ and $R^2$ can correspond to the groups necessary to provide an embodiment of the compounds of Formula (I) or (II) as described herein.

The compound of formula (IV) can be contacted with a compound of formula (IIIa):

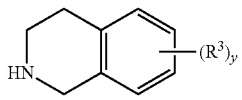

(IIIa)

Each $R^3$, independently, can be hydrogen, halogen, —N($R^4$)$_2$, —O—$R^4$, alkyl, alkoxy, alkenyl, alkynyl, cycloalkyl, heterocyclyl, aryl, or heteroaryl. Each $R^4$, independently, can be hydrogen or $C_1$-$C_6$ alkyl. y can be 0, 1, 2, 3, or 4.

In some embodiments, $R^2$ can be —$(CR^a R^b)_z$—N($R^4$)CO—$R^4$, or Ar.

$R^3$ can correspond to the groups necessary to provide an embodiment of the compounds of Formula (I) or (II) as described herein.

Other features, objects, and advantages will be apparent from the following description and the claims.

BRIEF DESCRIPTION OF THE DRAWINGS

FIG. 1 is a graph showing the inhibition of tumor growth by Compound 1 in nude mice that were subcutaneously injected with MDA-MB-231 human breast adenocarcinoma cells.

DETAILED DESCRIPTION

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. All references cited herein are incorporated by reference as if each had been individually incorporated.

DEFINITIONS

The terms "tetrahydroisoquinolin-2-yl-(quinazolin-4-yl) methanone", "5-tetrahydroisoquinolin-2-yl-(quinazolin-4-yl)methanone compound", and "tetrahydroisoquinolin-2-yl-(quinazolin-4-yl)methanone derivative" are used interchangeably to mean compounds of formula (I), as defined below. All scientific and technical terms used in this application have meanings commonly used in the art unless otherwise specified. As used herein, the following words or phrases have the meanings specified.

As used herein, "pharmaceutically acceptable carrier" means any solid or liquid material which, when combined with a compound of formula (I), allows the compound to retain biological activity, such as the ability to potentiate antibacterial activity of mast cells and macrophages. Examples include, but are not limited to, any of the standard pharmaceutical carriers such as a phosphate buffered saline solution, water, emulsions such as oil/water emulsions, and various types of wetting agents. Compositions comprising such carriers are formulated by well-known conventional methods (see, for example, Remington's Pharmaceutical Sciences, Chapter 43, 14th Ed., Mack Publishing Co., Easton, Pa.).

The term "conjugate" means a compound formed as a composite between two or more molecules. More specifically, the tetrahydroisoquinolin-2-yl-(quinazolin-4-yl) methanone derivative can be bonded, for example, covalently bonded, to cell-specific targeting moieties forming a conjugate compound for efficient and specific delivery of the agent to a cell of interest.

The phrase "targeting moiety" means a molecule which serves to deliver the compound of formula (I) to a specific site for the desired activity. Targeting moieties include, for example, molecules that specifically bind molecules on a specific cell surface. Such targeting moieties include anti-cell surface antigen antibodies. Cytokines, including interleukins and factors such as granulocyte/macrophage stimulating factor (GMCSF) are also specific targeting moieties, known to bind to specific cells expressing high levels of their receptors.

The term "prodrug moiety" is a substituent group which facilitates use of a compound, for example by facilitating entry of the drug into cells or administration of the compound. The prodrug moiety may be cleaved from the compound, for example by cleavage enzymes in vivo. Examples of prodrug moieties include phosphate groups, peptide linkers, and sugars, which moieties can be hydrolyzed in vivo.

The term "hyperproliferative disorder" refers to disorders characterized by an abnormal or pathological proliferation of cells, for example, tumors, cancers, neoplastic tissue and other premalignant and non-neoplastic or non-malignant hyperproliferative disorders.

Examples of tumors, cancers, and neoplastic tissue that can be treated by the compounds disclosed herein include but are not limited to malignant disorders such as breast cancers; osteosarcomas; angiosarcomas; fibrosarcomas and other sarcomas; leukemias; lymphomas; sinus tumors; ovarian, urethral, bladder, prostate and other genitourinary cancers; colon esophageal and stomach cancers and other gastrointestinal cancers; lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas. In some embodiments, the hyperproliferative disorder is a cancer. In some embodiments, the hyperproliferative disorder is a tumor.

Examples of premalignant and non-neoplastic or non-malignant hyperproliferative disorders include but are not limited to myelodysplastic disorders; cervical carcinoma-in-situ; familial intestinal polyposes such as Gardner syndrome; oral leukoplakias; histiocytoses; keloids; hemangiomas; hyperproliferative arterial stenosis, inflammatory arthritis; hyperkeratoses and papulosquamous eruptions including arthritis. Also included are viral induced hyperproliferative diseases such as warts and EBV induced disease (i.e., infectious mononucleosis), scar formation, and the like. The methods of treatment disclosed herein may be employed with any subject known or suspected of carrying or at risk of developing a hyperproliferative disorder as defined herein.

As used herein, "treatment" of a hyperproliferative disorder refers to methods of killing, inhibiting or slowing the growth or increase in size of a body or population of hyperproliferative cells or tumor or cancerous growth, reducing hyperproliferative cell numbers, or preventing spread to other anatomic sites, as well as reducing the size of a hyperproliferative growth or numbers of hyperproliferative cells. As used herein, "treatment" is not necessarily meant to imply cure or complete abolition of hyperproliferative growths. As used herein, a treatment effective amount is an amount effective to result in the killing, the slowing of the rate of growth of hyperproliferative cells, the decrease in size of a body of hyperproliferative cells, and/or the reduction in number of hyperproliferative cells. The potentiating agent (or agents) is included in an amount sufficient to enhance the activity of the first compound, such that the two (or more) compounds together have greater therapeutic efficacy than the individual compounds given alone (e.g., due to synergistic interaction; reduced combined toxicity, etc.).

Tetrahydroisoquinolin-2-yl-(quinazolin-4-yl)methanone Compounds

Tetrahydroisoquinolin-2-yl-(quinazolin-4-yl)methanones can have the structure of formula (I):

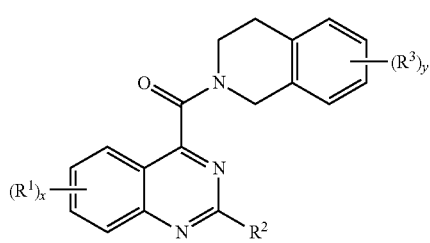

Each $R^1$, independently, can be hydrogen, halogen, or —O—$R^4$. $R^2$ can be —$(CR^aR^b)_z$—$R^5$. Each $R^3$, independently, can be hydrogen, halogen, —$N(R^4)_2$, —O—$R^4$, alkyl, alkoxy, alkenyl, alkynyl, cycloalkyl, heterocyclyl, aryl, or heteroaryl.

Each $R^a$, independently, can be hydrogen, halogen, hydroxy, alkyl, alkoxy, alkenyl, alkynyl, cycloalkyl, heterocyclyl, aryl, or heteroaryl. Each $R^b$, independently, can be hydrogen, halogen, hydroxy, alkyl, alkoxy, alkenyl, alkynyl, cycloalkyl, heterocyclyl, aryl, or heteroaryl.

Each $R^4$, independently, can be hydrogen or $C_1$-$C_6$ alkyl. $R^5$ can be hydrogen, halo, alkyl, hydroxy, alkyl, alkoxy, alkenyl, alkynyl, cycloalkyl, heterocyclyl, —N($R^4$)CO—$R^4$, or Ar.

Ar can be aryl or heteroaryl, wherein each of aryl and heteroaryl is optionally substituted by one to five substituents independently selected from hydrogen, halogen, —$R^4$, —N($R^4$)$_2$, nitro, —$(CH_2)_n$—NHCO—$R^4$, —O—$R^4$, alkyl, alkenyl, alkynyl, cycloalkyl, heterocyclyl, aryl, or heteroaryl.

n can be 0, 1, 2, or 3. x can be 0, 1, 2, 3, or 4. y can be 0, 1, 2, 3, or 4. z can be 0, 1, 2, 3, 4, 5, or 6.

A compound of formula (I) can be in the form of a pharmaceutically acceptable salt.

The term "halogen" or "halo" means F, Cl, Br, or I.

The term "alkyl" used alone or as part of a larger moiety (i.e. "alkoxy," "hydroxyalkyl," "alkoxyalkyl," and "alkoxycarbonyl") includes both straight and branched chains containing one to ten carbon atoms (i.e., 1, 2, 3, 4, 5, 6, 7, 8, 9, or 10 carbon atoms). Examples of alkyl groups include methyl (Me), ethyl (Et), propyl (Pr) (including n-propyl ("Pr or n-Pr), isopropyl ($^i$Pr or i-Pr), butyl (Bu) (including n-butyl ("Bu or n-Bu), isobutyl ($^i$Bu or i-Bu), and tert-butyl ($^t$Bu or t-Bu)), pentyl (Pe) (including n-pentyl) and so forth. An alkyl group may be optionally substituted by 1 to 6 substituents selected from halo, hydroxy, thiol, oxo, amino, alkylamino, dialkylamino, cyano, nitro, alkyl, alkoxy, alkenyl, alkynyl, cycloalkyl, heterocyclyl, aryl, or heteroaryl. In some embodiments, alkyl includes both straight and branched chains containing one to six carbon atoms.

The term "alkoxy" refers to an —O-alkyl radical, where alkyl is defined above. Examples of alkoxy groups include, such as, for example —O-Me, —O-Et, —O—Pr, and so on.

The term "alkenyl" used alone or as part of a larger moiety includes both straight and branched chains containing at least one double bond and two to ten carbon atoms (i.e., 2, 3, 4, 5, 6, 7, 8, 9, or 10 carbon atoms), as well as cyclic, non-aromatic alkenyl groups such as cyclopropenyl, cyclobutenyl, cyclopentenyl, cyclopentadienyl, cyclohexenyl, cyclohexadienyl, etc. As used herein, alkenyl groups also include mixed cyclic and linear alkyl groups, such as cyclopentenylmethyl, cyclopentenylethyl, cyclohexenylmethyl, etc., so long as the total number of carbon atoms is not exceeded. When the total number of carbons allows (i.e., more than 4 carbons), an alkenyl group may have multiple double bonds, whether conjugated or non-conjugated, but do not include aromatic structures. Examples of alkenyl groups include ethenyl, propenyl, butenyl, butadienyl, isoprenyl, dimethylallyl, geranyl and so forth. An alkenyl group may be optionally substituted by 1 to 6 substituents selected from halo, hydroxy, thiol, oxo, amino, alkylamino, dialkylamino, cyano, nitro, alkyl, alkoxy, alkenyl, alkynyl, cycloalkyl, heterocyclyl, aryl, or heteroaryl. In some embodiments, alkenyl includes both straight and branched chains containing at least one double bond and two to six carbon atoms.

The term "alkynyl" used alone or as part of a larger moiety includes straight and branched chains groups containing at least one triple bond and two to ten carbon atoms (i.e., 2, 3, 4, 5, 6, 7, 8, 9, or 10 carbon atoms). When the total number of carbon atoms allows (i.e., more than 4 carbons), an alkynyl group may have multiple triple bonds, whether conjugated or non-conjugated, but do not include aromatic structures. An alkynyl group can include more than one type of multiple bond, i.e., an alkynyl group can include one or more double bonds in addition to at least one triple bond. Examples of alkenyl groups include ethynyl, propynyl, but-2-yn-yl, but-3-ynyl, and so on. An alkynyl group may be optionally substituted by 1 to 6 substituents selected from halo, hydroxy, thiol, oxo, amino, alkylamino, dialkylamino, cyano, nitro, alkyl, alkoxy, alkenyl, alkynyl, cycloalkyl, heterocyclyl, aryl, or heteroaryl. In some embodiments, alkynyl includes both straight and branched chains containing at least one triple bond and two to six carbon atoms.

The term "cycloalkyl" includes mono-, bi-, or tricyclic non-aromatic carbocyclic ring systems having from 3 to 14 ring carbons, and optionally one or more double bonds. The ring systems may be fused, bridged, or spiro ring systems, or a combination of these. Examples of cycloalkyl groups include saturated monocyclic groups such as cyclopropyl, cyclobutyl, cyclopentyl, cyclohexyl, cycloheptyl, cyclohexyl, cycloheptyl, cyclooctyl, and the like; unsaturated monocyclic groups such as cyclopentenyl, cyclohexenyl, cycloheptenyl, cyclopentadienyl, cyclohexadienyl, cycloheptadienyl, cyclooctatetraenyl, and the like. Examples of cycloalkyl groups also include saturated bicyclic groups such as decahydronaphthalene, bicyclo[3.1.1]heptyl, norbornane, bicyclo[2.2.2]octyl, and the like; unsaturated bicyclic groups such as norbornenyl, bicyclo[2.2.2]oct-2-enyl, and the like. Examples of cycloalkyl groups also include saturated tricyclic groups such as tetradecahydroanthracene, tetradecahydrophenanthrene, dodecahydro-s-indacene, and the like, and unsaturated tricyclic groups. Also included within the scope of the term "cycloalkyl" are spiro ring systems, such as spiro[4.4]nonyl, spiro[4.5]decyl, spiro[5.5]undecyl, spiro[4.6]undecyl, and the like. Also included within the scope of the term "cycloalkyl" is a group in which a non-aromatic carbocyclic ring is fused to one or more aromatic or non-aromatic rings, such as in a tetrahydronaphthyl or indanyl group, where the radical or point of attachment is on the non-aromatic carbocyclic ring. A cycloalkyl group may be optionally substituted by 1 to 6 substituents selected from halo, hydroxy, thiol, oxo, amino, alkylamino, dialkylamino, cyano, nitro, alkyl, alkoxy, alkenyl, alkynyl, cycloalkyl, heterocyclyl, aryl, or heteroaryl. In some embodiments, cycloalkyl includes carbocyclic ring systems having from 5 to 6 ring carbons, and optionally one or more double bonds.

The term "heterocycle", "heterocyclyl", or "heterocyclic" unless otherwise indicated includes mono-, bi-, or tricyclic non-aromatic ring systems having five to fourteen members, preferably five to ten, in which one or more ring carbons, preferably one to four, are each replaced by a heteroatom such as N, O, or S. Examples of heterocyclic groups include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "aryl" used alone or as part of a larger moiety, refers to mono-, bi-, or tricyclic aromatic hydrocarbon ring systems having five to fourteen members, such as phenyl, 1-naphthyl, 2-naphthyl, 1-anthracyl and 2-anthracyl. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl or tetrahydronaphthyl, where the radical or point of attachment is on the aromatic ring. In some embodiments, aryl includes substituted phenyl and unsubstituted phenyl.

The term "heteroaryl", used alone or as part of a larger moiety, refers to heteroaromatic ring groups having five to fourteen members, preferably five to ten, in which one or more ring carbons, preferably one to four, are each replaced by a heteroatom such as N, O, or S. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroaromatic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" may be used interchangeably with the term "heteroaryl ring" or the term "heteroaromatic."

The term "amine" or "amino" used alone or as part of a larger moiety refers to unsubstituted (—NH$_2$). The term "alkylamine" refers to mono- (—NRH) or di-substituted (—NR$_2$) amine where at least one R group is an alkyl substituent, as defined above. Examples of alkylamino and dialkylamino groups include methylamino (—NHCH$_3$), and dimethylamino (—N(CH$_3$)$_2$), respectively.

The compounds can be in the form of pharmaceutically acceptable salts. Pharmaceutically acceptable salts of compounds of compounds having formula (I) include pharmaceutically acceptable salts of inorganic or organic acids, alkali metals, or ammonium; for example, salts with inorganic acids such as hydrochloric acid, bromic acid, sulfuric acid, sodium hydrogensulfate, phosphoric acid, nitric acid, or carbonic acid; salts with organic acids such as formic acid, acetic acid, propionic acid, oxalic acid, succinic acid, benzoic acid, citric acid, maleic acid, malonic acid, tartaric acid, gluconic acid, lactic acid, fumaric acid, lactobionic acid, salicylic acid, or acetylsalicylic acid; salts with amino acids such as glycine, alanine, valine, leucine, isoleucine, serine, cysteine, cystine, aspartic acid, glutamic acid, lysine, arginine, tyrosine, or proline; salts with sulfonic acids such as methane sulfonic acid, ethane sulfonic acid, benzene sulfonic acid, or toluene sulfonic acid; an alkali metal salt, for example, a lithium, sodium or potassium salt; an alkali earth metal salt, for example, a magnesium or calcium salt; an ammonium salt; or a salt with a physiologically acceptable organic base, for example a salt with methylamine, dimethylamine, trimethylamine, piperidine, morpholine or tris-(2-hydroxyethyl)amine, or the like.

Tetrahydroisoquinolin-2-yl-(quinazolin-4-yl)methanone compounds may provide potent therapeutic molecules for the treatment of disorders such as tumors.

Tetrahydroisoquinolin-2-yl-(quinazolin-4-yl)methanone compounds can have prominent antitumor activities and very low toxicities. Tetrahydroisoquinolin-2-yl-(quinazolin-4-yl) methanone derivatives, methods of preparation, and antitumor activities of such compounds are disclosed herein.

More particularly, tetrahydroisoquinolin-2-yl-(quinazolin-4-yl) methanone compounds and their use in the treatment of a hyperproliferative disorder, disease or condition in a subject (e.g., a human patient or other animal subject) are described. Methods for treatment can include administering to a subject an effective amount of a tetrahydroisoquinolin-2-yl-(quinazolin-4-yl)methanone compound. Such a treatment can, e.g., prevent, ameliorate, and/or inhibit symptoms of the hyperproliferative condition, and/or can prevent or inhibit cellular proliferation or growth, for instance in a tumor, such as a malignant neoplasm. A treatment strategy would decrease the tumor burden, at least to a measurable degree, and improve survival of patients suffering from the hyperproliferative condition. Among the diseases, disorders and conditions susceptible to treatment are neoplasms, and more specifically tumors of various origins (lung, colon, stomach, smooth muscle, esophagus, non-Hodgkin's lymphoma, non-small cell lung cancer, etc.).

Compounds of formula (I) can be very active against a wide range of hyperproliferative diseases, including tumors, and used as an anti-tumor agent. For example, compounds of formula (I) can be active against tumors of the ovary, tumors of the prostate, breast tumors, kidney tumors, colon tumors, pancreatic tumors, brain tumors and melanoma. By very active, it is meant that a compound can have an $IC_{50}$ of 5.0 μM or less, 2.0 μM or less, 1.0 μM or less, 0.5 μM or less, 0.2 μM or less, or 0.1 μM or less with respect to at least one cell line for a particular tumor.

Some embodiments of tetrahydroisoquinolin-2-yl-(quinazolin-4-yl) methanone compounds are listed above, and/or described below in the Examples.

1,2,3,4-Tetrahydroisoquinoline compounds 1,2,3,4-tetrahydroisoquinoline compounds, as described below, can be used in the preparation of tetrahydroisoquinolin-2-yl-(quinazolin-4-yl)methanone compounds. A 1,2,3,4-tetrahydroisoquinoline compound can have the structure of formula (IIIa):

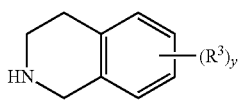

(IIIa)

Each $R^3$, independently, can be hydrogen, halogen, $-N(R^4)_2$, $-O-R^4$, alkyl, alkoxy, alkenyl, alkynyl, cycloalkyl, heterocyclyl, aryl, or heteroaryl. Each $R^4$, independently, can be hydrogen or $C_1$-$C_6$ alkyl. y can be 0, 1, 2, 3, or 4.

In some cases, a 1,2,3,4-tetrahydroisoquinoline compound can have the structure of formula (IIIb):

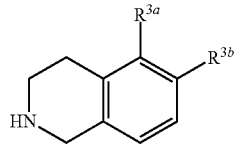

(IIIb)

In formula (IIIb), $R^{3a}$ can be $-OR^4$ or $-N(R^4)_2$; $R^{3b}$ can be $C_1$-$C_6$ alkyl, $-OR^4$ or $-N(R^4)_2$; and each $R^4$, independently, can be hydrogen or $C_1$-$C_6$ alkyl. In some embodiments, $R^{3b}$ is $-OH$ or $-OCH_3$.

As will be apparent to a person of ordinary skill in the art, compounds of formula (IIIa) or (IIIb) can be appropriately substituted with the groups necessary so as to provide an embodiment of the compounds of Formula (I) or (II) as described herein. Some examples of 1,2,3,4-tetrahydroisoquinoline compounds include: 5-hydroxy-6-methoxy-1,2,3,4-tetrahydroisoquinoline; 5,6-dihydroxy-1,2,3,4-tetrahydroisoquinoline; 5,6-dimethoxy-1,2,3,4-tetrahydroisoquinoline; 5-hydroxy-6-dimethylamino-1,2,3,4-tetrahydroisoquinoline; and 5-hydroxy-6-methyl-1,2,3,4-tetrahydroisoquinoline.

Synthesis of Tetrahydroisoquinolin-2-yl-(quinazolin-4-yl)methanone Compounds

In general, tetrahydroisoquinolin-2-yl-(quinazolin-4-yl) methanone compounds can be prepared by linking a compound of formula (IIIa) or (IIIb) to a compound of formula (IV):

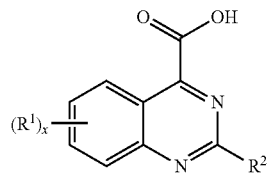

(IV)

Each $R^1$, independently, can be hydrogen, halogen, or $-O-R^4$. $R^2$ can be $-(CR^aR^b)_z-R^5$.

Each $R^a$, independently, can be hydrogen, halogen, hydroxy, alkyl, alkoxy, alkenyl, alkynyl, cycloalkyl, heterocyclyl, aryl, or heteroaryl. Each $R^b$, independently, can be hydrogen, halogen, hydroxy, alkyl, alkoxy, alkenyl, alkynyl, cycloalkyl, heterocyclyl, aryl, or heteroaryl.

Each $R^4$, independently, can be hydrogen or $C_1$-$C_6$ alkyl. $R^5$ can be hydrogen, halo, alkyl, hydroxy, alkyl, alkoxy, alkenyl, alkynyl, cycloalkyl, heterocyclyl, $-N(R^4)CO-R^4$, or Ar.

Ar can be aryl or heteroaryl, wherein each of aryl and heteroaryl is optionally substituted by one to five substituents independently selected from hydrogen, halogen, $-R^4$, $-N(R^4)_2$, nitro, $-(CH_2)_n-NHCO-R^4$, $-O-R^4$, alkyl, alkenyl, alkynyl, cycloalkyl, heterocyclyl, aryl, or heteroaryl.

n can be 0, 1, 2, or 3. x can be 0, 1, 2, 3, or 4. z can be 0, 1, 2, 3, 4, 5, or 6.

As will be apparent to a person of ordinary skill in the art, compounds of formula (IV) can be appropriately substituted with the groups necessary so as to provide an embodiment of the compounds of Formula (I) or (II) as described herein.

In some instances, a compound of formula (I) can be prepared from a different compound of formula (I), for example by adding, removing, or altering a substituent. In one example, a methoxy-substituted compound of formula (I) can be transformed into a hydroxy-substituted compound of formula (I):

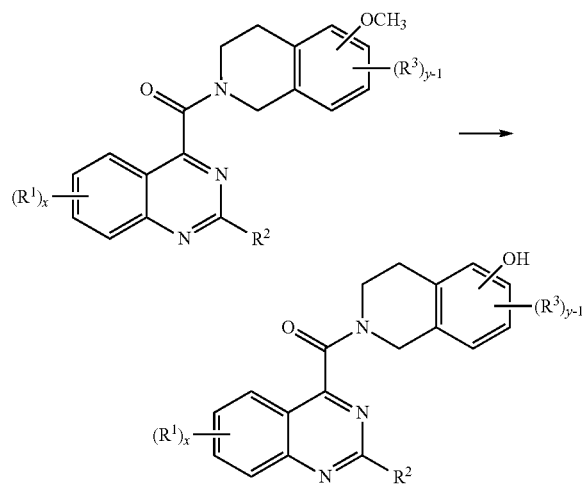

Other suitable transformations of a compound of formula (I) into a different compound of formula (I) will be apparent to those skilled in the art.

Pharmaceutical Compositions and Administration

The compounds of formula (I) and pharmaceutically acceptable salts thereof may be combined with a non-toxic pharmaceutically acceptable vehicle such as a carrier, adjuvant, and/or excipient, and then the mixture may be administered orally or parenterally in the form of tablets, capsules, troches, solutions, suspensions to prevent or treat various kinds of tumors of human beings or mammals.

The amount of a tetrahydroisoquinolin-2-yl-(quinazolin-4-yl)methanone compound required for use in treatment will vary depending on the particular salt selected and with the route of administration, the nature of the condition being treated and the age and condition of the patient, and will be ultimately at the discretion of the attendant physician or clinician.

Effective dosages and routes of administration of compounds of formula (I) are conventional. The exact amount (effective dose) of the tetrahydroisoquinolin-2-yl-(quinazolin-4-yl)methanone compound will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York, which is incorporated by reference in its entirety. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, 6 to 90 mg/kg/day, or in the range of 15 to 60 mg/kg/day. For example, suitable doses may be 0.5, 5, 10, 25, 50, 100, 250 or 500 mg/kg of body weight per day.

A tetrahydroisoquinolin-2-yl-(quinazolin-4-yl)methanone compound can be conveniently administered in unit dosage form; for example, containing 5 to 1000 mg, 10 to 750 mg, or 50 to 500 mg of active ingredient per unit dosage form.

A tetrahydroisoquinolin-2-yl-(quinazolin-4-yl) methanone compound can be administered to achieve peak plasma concentrations of from about 0.5 to about 75 µM, about 1 to 50 µM, or, about 2 to about 30 µM. Exemplary desirable plasma concentrations include at least or no more than 0.25, 0.5, 1, 5, 10, 25, 50, 75, 100 or 200 µM. This may be achieved, for example, by the intravenous injection of a 0.05 to 5% solution of a tetrahydroisoquinolin-2-yl-(quinazolin-4-yl) methanone compound, optionally in saline, or orally administered as a bolus containing about 1-100 mg of a tetrahydroisoquinolin-2-yl-(quinazolin-4-yl) methanone compound. Desirable blood levels may be maintained by continuous infusion to provide about 0.01-5.0 mg/kg/hr, for example at least or no more than 0.005, 0.01, 0.1, 2.5, 5.0 or 10.0 mg/kg/hr. Alternatively, such levels can be obtained by intermittent infusions containing about 0.4-15 mg/kg, for example at least or no more than 0.25, 0.5, 1.0, 5.0, 10.0, 15.0 or 25.0 mg/kg of a tetrahydroisoquinolin-2-yl-(quinazolin-4-yl)methanone compound.

Conjugates of Tetrahydroisoquinolin-2-yl-(quinazolin-4-yl)methanones and Targeting Tetrahydroisoquinolin-2-yl-(quinazolin-4-yl)methanones to Cells In an exemplary embodiment, the tetrahydroisoquinolin-2-yl-(quinazolin-4-yl) methanone compound can be targeted to cells where treatment is desired, for example, to human cancer cells. The compound is targeted to the desired cell by conjugation to a targeting moiety that specifically binds the desired cell, thereby directing administration of a conjugated molecule. Useful targeting moieties are ligands which specifically bind cell antigens or cell surface ligands, for example, antibodies against the B cell antigen, CD19 (such as B43) and the like.

To form the conjugates, targeting moieties are covalently bound to sites on the tetrahydroisoquinolin-2-yl-(quinazolin-4-yl) methanone compound. The targeting moiety, which can be a polypeptide, is bound to a tetrahydroisoquinolin-2-yl-(quinazolin-4-yl)methanone compound at a reactive site, including $NH_2$, SH, CHO, or COOH groups, and the like. Specific linking agents can be used to join the compounds. Linking agents can be chosen according to the reactive site to which the targeting moiety is to be attached.

Methods for selecting an appropriate linking agent and reactive site for attachment of the targeting moiety to the compound of formula (I) are known, and are described, for example, in Hermanson, et al., Bioconjugate Techniques, Academic Press, 1996; Hermanson, et al., Immobilized Affinity Ligand Techniques, Academic Press, 1992; and Pierce Catalog and Handbook, 1996, pp. T155-T201, each of which is incorporated by reference in its entirety.

EXAMPLES

General

All chemicals were reagent grade and were purchased from Aldrich Chemical Company (Milwaukee, Wis.) or Sigma Chemical Company (St. Louis, Mo.). Solvents were routinely distilled prior to use. Anhydrous tetrahydrofuran was distilled from sodium/benzophenone prior to use.

Nuclear magnetic resonance spectra were recorded on a Bruker 300 MHz AVANCE-II spectrometer with 120-BACS Autosampler, using tetramethylsilane (TMS) as the internal standard at zero ppm; chemical shifts were reported in parts per million (ppm) and the abbreviations s, d, t, b and m refer to singlet, doublet, triplet, broad and multiplet, respectively. LCMS were performed on a Shimadzu LCMS2010 or LCMS2020. Column chromatography was performed on Merck silica gel 60 (70~230 mesh). TLC was carried out using plates coated with silica gel 60F254 purchased from Merck Co Preparative HPLC was performed using Waters SunFire Prep C18 (5 um, 15×190 mm) with UV 254 nm detector.

Example I

Synthesis of quinazoline-4-carboxylic acid derivatives

I-1. Synthesis of 2-(4-fluorophenyl)quinazoline-4-carboxylic acid 2-(4-Fluorophenyl)quinazoline-4-carboxylic acid was prepared from 4-fluorobenzoyl chloride and aniline as outlined in Scheme 1:

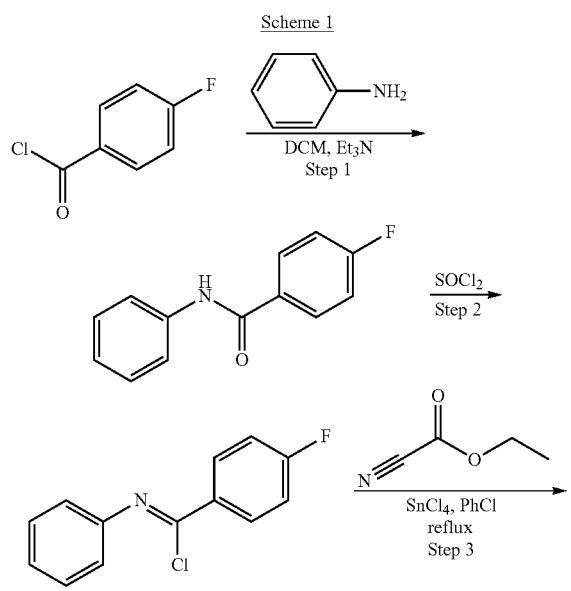

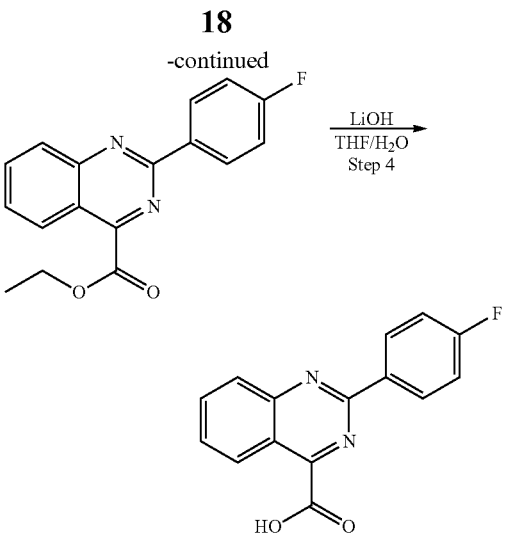

1. Synthesis of 4-fluoro-N-phenylbenzamide

Into a 5000-mL 4-necked round-bottom flask, was placed aniline (93 g, 1.0 mol, 1.0 equiv.), triethylamine (202 g, 2.0 mol, 2.0 equiv.) and dichloromethane (2,000 mL). This was followed by the addition of 4-fluorobenzoyl chloride (174 g, 1.1 mol, 1.1 equiv.) dropwise with stirring at 0° C. The mixture was stirred at room temperature for 3 hours. The resulting solution was concentrated under vacuum. The solid was filtered out. The filter cake was washed with 1×200 mL of dichloromethane and 3×500 mL of water. This resulted in 200 g (93%) of 4-fluoro-N-phenylbenzamide as white solid. MS (ESI) m/z 216 ([M+H]$^+$).

2. Synthesis of ethyl 2-(4-fluorophenyl) quinazoline-4-carboxylate (Step 2 & 3)

Into a 500-mL 3-necked round-bottom flask, was placed 4-fluoro-N-phenylbenzamide (50 g; 233 mmol) and thionyl chloride (200 mL). The mixture was stirred at refluxed for 3 h and then the solvent was evaporated to dryness to afford (Z)-4-fluoro-N-phenylbenzimidoyl chloride as white solid. The solid was dissolved into chlorobenzene and SnCl$_4$ (39.0 mmol) and ethyl cyanoformate (39.0 mmol) were added. The reaction mixture was heated at 140° C. for 1 hour and concentrated to get black oil. The black oil was added into water, made alkaline with 20% NaOH, and extracted with 2×300 mL of dichloromethane. The organic layer was washed with 1×100 mL of brine and dried over sodium sulphate and concentrated to get the crude product, which was purified by flash chromatography on silica gel, eluting with hexane/ethyl acetate (10:1) to afford ethyl 2-(4-fluorophenyl)quinazoline-4-carboxylate as white solid (8.1 g, 11.7%, 2 steps). MS (ESI) m/z 297 ([M+H]$^+$).

3. 2-(4-fluorophenyl)quinazoline-4-carboxylic acid (Step 4)

Into a 500-mL 3-necked round-bottom flask, was placed ethyl 2-(4-fluorophenyl)quinazoline-4-carboxylate (15 g, 50.63 mmol, 1.00 equiv), oxolane (150 mL), lithiumol (2.4 g, 100.22 mmol, 2.00 equiv) and water (50 mL). The resulting solution was stirred overnight at 26° C. The resulting mixture was concentrated under vacuum. The pH value of the solution was adjusted to 5 with hydrogen chloride (2 mol/L). The solids were collected by filtration and washed with water. This resulted in 10 g (74%) of 2-(4-fluorophenyl)quinazoline-4-carboxylic acid as a yellow solid. $^1$H NMR (400 MHz, DMSO-d$_6$) δ 7.37-7.41 (m, 2H), 7.65-7.69 (m, 1H), 7.96-8.03 (m, 2H), 8.20-8.22 (m, 1H), 8.56-8.61 (m, 2H); MS (ESI) m/z 269 ([M+H]$^+$).

I-2. Synthesis of 2-(4-methylphenyl)quinazoline-4-carboxylic acid 2-(4-Methylphenyl)quinazoline-4-carboxylic acid was prepared from 4-methyl benzoic acid and aniline as outlined in Scheme 2.

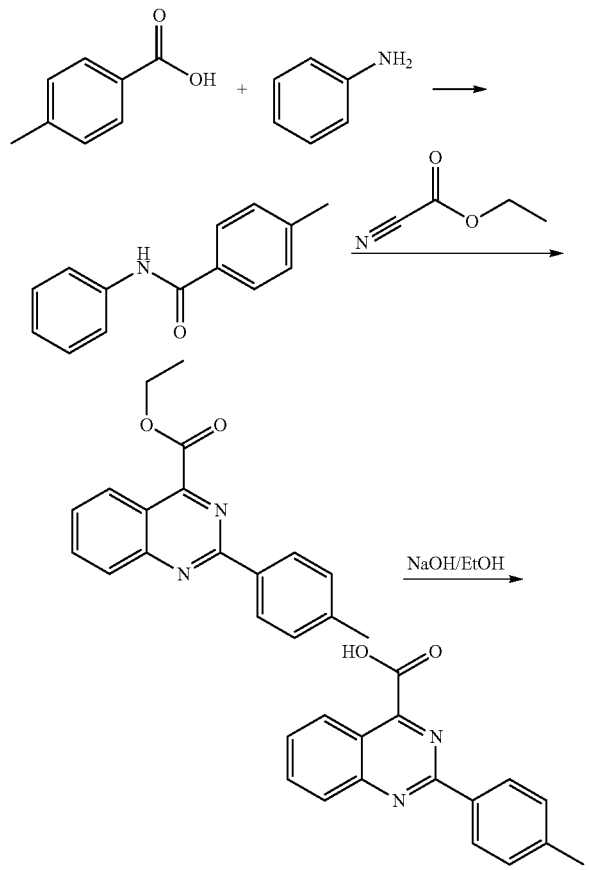

1. Synthesis of 4-methyl-N-phenylbenzamide

Into a 500-mL 3-necked round-bottom flask purged and maintained with an inert atmosphere of nitrogen, was placed a solution of 4-methylbenzoic acid (20 g, 146.90 mmol, 1.00 equiv) in thionyl chloride (60 g). The mixture was stirred for 2 h at 80° C. The mixture was concentrated under vacuum. The residue was dissolved in dichloromethane (200 mL). This was followed by the addition of triethylamine (29.7 g, 293.51 mmol, 2.00 equiv) dropwise with stirring at 0° C. To this was added aniline (13.6 g, 146.04 mmol, 1.00 equiv) dropwise with stirring at 0° C. The resulting solution was allowed to react, with stirring overnight at room temperature. The resulting mixture was washed with 3×100 mL of hydrogen chloride (5%) and 2×100 mL NaOH (5%). The mixture was washed with 3×100 mL of water. The mixture was dried over anhydrous sodium sulfate and concentrated under vacuum. This resulted in 19.37 g (62%) of 4-methyl-N-phenylbenzamide as a white solid. MS (ESI) m/z 212 ([M+H]$^+$).

2. Synthesis of ethyl 2-(4-methylphenyl)quinazoline-4-carboxylate

Into a 100-mL 3-necked round-bottom flask purged and maintained with an inert atmosphere of nitrogen, was placed a solution of 4-methyl-N-phenylbenzamide (6 g, 28.40 mmol, 1.00 equiv) in toluene (60 mL) and PCl$_5$ (7.13 g, 34.24 mmol, 1.20 equiv). The mixture was stirred for 2 h at 65° C. The mixture was concentrated under vacuum. The residue was diluted with 30 mL of PhCl. To the mixture was added 2-ethoxy-2-oxoacetonitrile (3.37 g, 34.01 mmol, 1.20 equiv), SnCl$_4$ (12.5 g, 1.70 equiv). The resulting solution was allowed to react, with stirring, overnight while the temperature was maintained at 125° C. in an oil bath. The resulting mixture was concentrated under vacuum. The residue was extracted with 3×100 mL of ethyl acetate and the organic layers combined. The resulting mixture was washed with 4×100 mL of water. The mixture was dried over anhydrous sodium sulfate and concentrated under vacuum. The residue was applied onto a silica gel column with ethyl acetate/petroleum ether (1:30). This resulted in 2.64 g (32%) of ethyl 2-(4-methylphenyl)quinazoline-4-carboxylate as a light green solid. MS (ESI) m/z 293 ([M+H]$^+$).

3. Synthesis of 2-(4-methylphenyl)quinazoline-4-carboxylic acid

Into a 150-mL 3-necked round-bottom flask, was placed a solution of ethyl 2-(4-methylphenyl)quinazoline-4-carboxylate (2.64 g, 9.03 mmol, 1.00 equiv) in ethanol (50 mL). This was followed by the addition of sodium hydroxide (1.8 g, 45.00 mmol, 5.00 equiv, 20%) dropwise with stirring at room temperature. The resulting solution was stirred overnight at room temperature. The resulting mixture was concentrated under vacuum. The residue was diluted with 50 mL of water. Hydrogen chloride (5%) was employed to adjust the pH to 3-4. The solids were collected by filtration. This resulted in 2.30 g (96%) of 2-(4-methylphenyl)quinazoline-4-carboxylic acid as a light green solid. MS (ESI) m/z 265 ([M+H]$^+$).

I-3. Synthesis of 2-phenylquinazoline-4-carboxylic acid

2-Phenylquinazoline-4-carboxylic acid was obtained by the same way with the preparation of 2-(4-methylphenyl)quinazoline-4-carboxylic acid (last step yield 65%) as a yellow solid. MS (ESI) m/z 251 ([M+H]$^+$).

I-4. Synthesis of 2-(4-methoxyphenyl)quinazoline-4-carboxylic acid 2-(4-Methoxyphenyl)quinazoline-4-carboxylic acid was obtained by the same way with the preparation of 2-(4-methylphenyl)quinazoline-4-carboxylic acid (last step yield 77%) as a light green solid. MS (ESI) m/z 281 ([M+H]$^+$).

I-5. Synthesis of 2-(4-chlorophenyl)quinazoline-4-carboxylic acid 2-(4-Chlorophenyl)quinazoline-4-carboxylic acid was obtained by the same way with the preparation of 2-(4-methylphenyl)quinazoline-4-carboxylic acid (last step yield 75%) as a white solid. MS (ESI) m/z 285 ([M+H]+).

I-6. Synthesis of 2-[4-(dimethylamino)phenyl]quinazoline-4-carboxylic acid

2-[4-(Dimethylamino)phenyl]quinazoline-4-carboxylic acid was prepared from 4-(dimethylamino)benzaldehyde and 2-aminobenzamide as outlined in Scheme 3.

Scheme 3

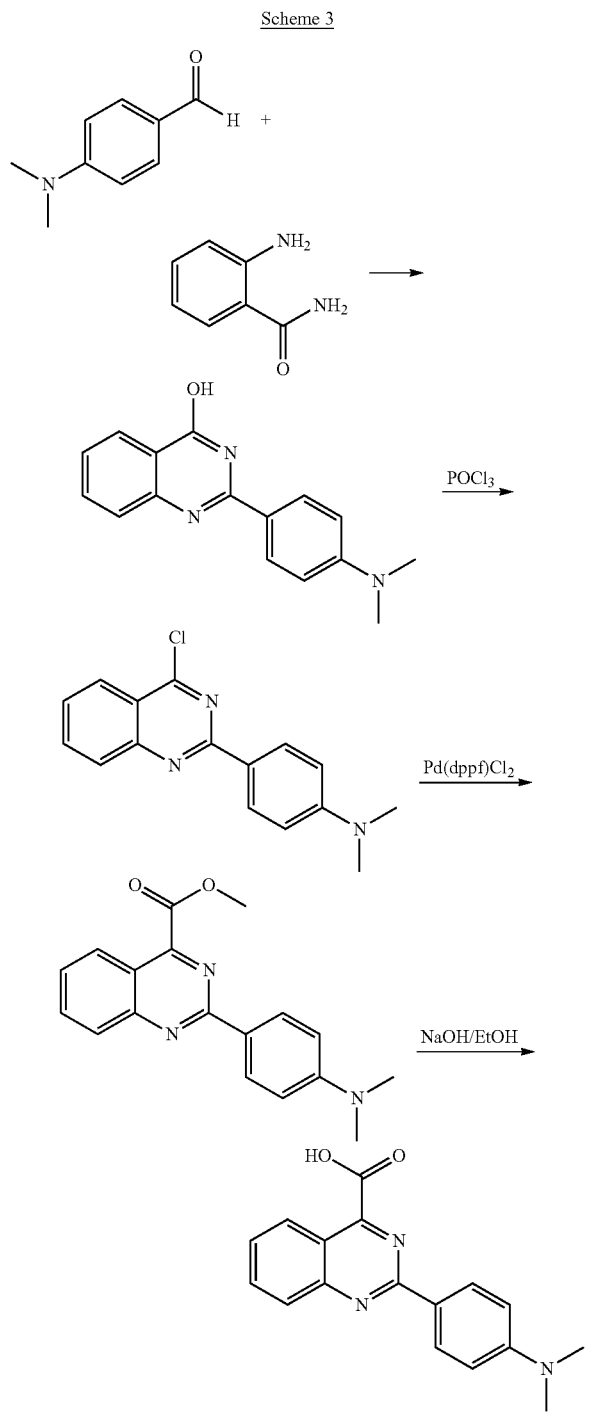

1. Synthesis of 2-[4-(dimethylamino)phenyl]quinazolin-4-ol

Into a 100-mL 3-necked round-bottom flask purged and maintained with an inert atmosphere of nitrogen, was placed a solution of 2-aminobenzamide (1.36 g, 9.99 mmol, 1.00 equiv) in dimethylacetamide (25 mL), 4-(dimethylamino) benzaldehyde (1.49 g, 9.99 mmol, 1.00 equiv) and sulfonylideneoxidane sodium (1.6 g, 15.53 mmol, 1.50 equiv). The resulting solution was stirred overnight at 150° C. in an oil bath. The reaction mixture was cooled to 25° C. The resulting solution was diluted with 100 mL of water. The solids were collected by filtration. The solid was washed with 2×20 mL of water and 1×20 mL of petroleum ether. This resulted in 2.1 g (79%) of 2-[4-(dimethylamino)phenyl]quinazolin-4-ol as a gray solid. MS (ESI) m/z 266 ([M+H]+).

2. Synthesis of 4-(4-chloroquinazolin-2-yl)-N,N-dimethylaniline

Into a 100-mL round-bottom flask purged and maintained with an inert atmosphere of nitrogen, was placed a solution of 2-[4-(dimethylamino)phenyl]quinazolin-4-ol (2 g, 7.54 mmol, 1.00 equiv) in POCl₃ (20 mL). The resulting solution was stirred for 5 h at 140° C. in an oil bath. The resulting mixture was concentrated under vacuum. The residue was dissolved in 50 mL of dichloromethane. The resulting mixture was washed with 2×20 mL of saturation sodium bicarbonate solution and 1×20 mL of brine. The mixture was dried over anhydrous sodium sulfate and concentrated under vacuum. This resulted in 2.0 g (93%) of 4-(4-chloroquinazolin-2-yl)-N,N-dimethylaniline as a red solid. MS (ESI) m/z 284 ([M+H]+).

3. Synthesis of 2-[4-(dimethylamino)phenyl]quinazoline-4-carboxylate

Into a 1-L pressure tank reactor, was placed a solution of 4-(4-chloroquinazolin-2-yl)-N,N-dimethylaniline (2.2 g, 7.75 mmol, 1.00 equiv) in methanol (300 mL), Pd(dppf)Cl₂ (440 mg, 0.10 equiv) and triethylamine (7 mL, 3.00 equiv). To the above CO (gas, 10 atm) was introduced in. The resulting solution was stirred for 8 h at 60° C. in an oil bath. The resulting mixture was concentrated under vacuum. The residue was applied onto a silica gel column with ethyl acetate/petroleum ether (1:9). This resulted in 1.8 g (76%) of methyl 2-[4-(dimethylamino)phenyl]quinazoline-4-carboxylate as a red solid. MS (ESI) m/z 308 ([M+H]+).

4. Synthesis of 2-[4-(dimethylamino)phenyl]quinazoline-4-carboxylic acid

Into a 250-mL round-bottom flask, was placed a solution of methyl 2-[4-(dimethylamino)phenyl]quinazoline-4-carboxylate (2.02 g, 6.57 mmol, 1.00 equiv) in ethanol (60 mL) and a solution of NaOH (1.32 g, 33.00 mmol, 5.00 equiv) in water (20 mL). The resulting solution was stirred for 6 h at 50° C. in an oil bath. The reaction mixture was cooled to room temperature. The mixture was concentrated under vacuum. The residue was dissolved in 20 mL of water. The pH value of the solution was adjusted to 5-6 with acetic acid. The solids were collected by filtration. This resulted in 800 mg (41%) of 2-[4-(dimethylamino)phenyl]quinazoline-4-carboxylic acid as a red solid. (ESI) m/z 294 ([M+H]+).

I-7. Synthesis of 2-[4-(trifluoromethyl)phenyl]quinazoline-4-carboxylic acid

2-[4-(Trifluoromethyl)phenyl]quinazoline-4-carboxylic acid was obtained by the same way with the preparation of 2-(4-methylphenyl)quinazoline-4-carboxylic acid (last step yield 65%) as a light yellow solid. (ESI) m/z 319 ([M+H]⁺).

I-8. Synthesis of 2-(3-fluorophenyl)quinazoline-4-carboxylic acid 2-(3-Fluorophenyl)quinazoline-4-carboxylic acid was obtained by the same way with the preparation of 2-[4-(dimethylamino)phenyl]quinazoline-4-carboxylic acid (last step yield 81%) as a white solid. MS (ESI) m/z 269 ([M+H]⁺).

I-9. Synthesis of 2-(3-methoxyphenyl)quinazoline-4-carboxylic acid 2-(3-Methoxyphenyl)quinazoline-4-carboxylic acid was obtained by the same way with the preparation of 2-(4-methylphenyl)quinazoline-4-carboxylic acid (last step yield 97%) as a light yellow solid. MS (ESI) m/z 281 ([M+H]⁺).

I-10. Synthesis of 2-[3-(trifluoromethyl)phenyl]quinazoline-4-carboxylic acid 2-[3-(trifluoromethyl)phenyl]quinazoline-4-carboxylic acid was obtained by the same way with the preparation of 2-(4-methylphenyl)quinazoline-4-carboxylic acid (last step yield 86%) as a white solid. MS (ESI) m/z 319 ([M+H]⁺).

I-11. Synthesis of 2-(2,4-difluorophenyl)quinazoline-4-carboxylic acid 2-(2,4-Difluorophenyl)quinazoline-4-carboxylic acid was obtained by the same way with the preparation of 2-(4-methylphenyl)quinazoline-4-carboxylic acid (last step yield 77%) as a light yellow solid. MS (ESI) m/z 287 ([M+H]⁺).

I-12. Synthesis of 2-(4-acetamidophenyl)quinazoline-4-carboxylic acid 2-(4-Acetamidophenyl)quinazoline-4-carboxylic acid was prepared from 4-nitrobenzoic acid and aniline as outlined in Scheme 4.

Scheme 4

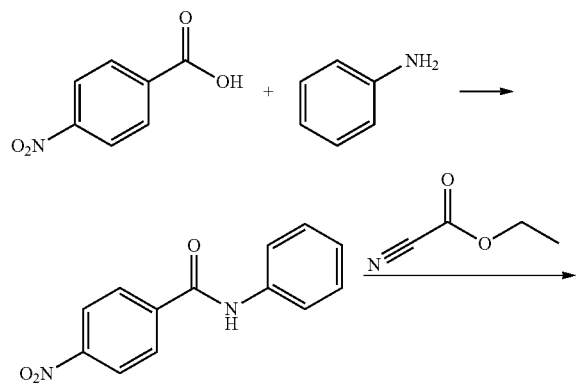

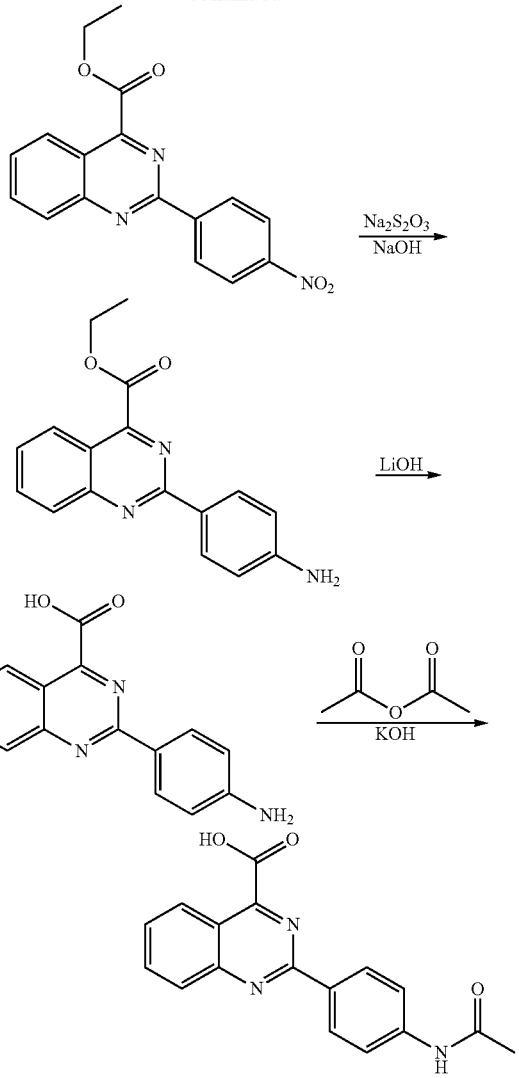

1. Synthesis of 4-nitro-N-phenylbenzamide

Into a 1-L 3-necked round-bottom flask purged and maintained with an inert atmosphere of nitrogen, was placed a solution of 4-nitrobenzoic acid (167 g, 999.29 mmol, 1.00 equiv) in dichloromethane (400 mL) and ClCOCOCl (317.5 g, 2.50 equiv). This was followed by the addition of N,N-dimethylformamide (1 mL) dropwise with stirring. The resulting solution was stirred for 4 h at room temperature. The mixture was concentrated under vacuum. To the residue was added a solution of PhNH₂ (93 g, 1.00 equiv) in dichloromethane (400 mL), triethylamine (415 mL, 3.00 equiv) dropwise with stirring at 0° C. The resulting solution was stirred overnight at room temperature. The resulting mixture was washed with 2×500 mL of HCl (10%) and 1×500 mL of brine. The mixture was dried over anhydrous sodium sulfate and concentrated under vacuum. The residue was diluted with 500 mL of petroleum ether/ethyl acetate=5:1. The solids were collected by filtration. This resulted in 205 g (85%) of 4-nitro-N-phenylbenzamide as light yellow solid. ¹H NMR (300 MHz, DMSO-d₆) δ 7.12-7.17 (m, 1H), 7.32-7.41 (m, 2H), 7.78-7.81 (m, 2H), 8.16-8.21 (m, 2H), 8.36-8.42 (m, 2H), 10.58 (s, 1H); MS (ESI) m/z 243 ([M+H]⁺).

2. Synthesis of 2-(4-nitrophenyl)quinazoline-4-carboxylate

Into a 2-L 3-necked round-bottom flask purged and maintained with an inert atmosphere of nitrogen, was placed a solution of 4-nitro-N-phenylbenzamide (200 g, 825.66 mmol, 1.00 equiv) in $PhCH_3$ (1 L) and $PCl_5$ (208 g, 1.20 equiv). The resulting solution was stirred for 4 h at 80° C. in an oil bath. The mixture was concentrated under vacuum. To this was added PhCl (1 L). To the mixture was added $CNCO_2Et$ (163 g, 2.00 equiv) and $SnCl_4$ (364 g, 1.70 equiv). The mixture was stirred overnight at 125° C. The resulting mixture was concentrated under vacuum. The resulting solution was diluted with 500 mL of dichloromethane. The resulting mixture was washed with 2×500 mL of $H_2O$, 2×500 mL of brine. The organic layer was dried over anhydrous sodium and concentrated under vacuum. The solids were collected by filtration. This resulted in 200 g (75%) of ethyl 2-(4-nitrophenyl)quinazoline-4-carboxylate as a light yellow solid. $^1H$ NMR (300 MHz, DMSO-$d_6$) δ 1.46 (t, 3H), 4.57-4.64 (q, 2H), 7.87-7.93 (m, 1H), 8.16-8.20 (m, 2H), 8.42-8.46 (m, 3H), 8.73-8.78 (m, 2H); MS (ESI) m/z 324 ([M+H]$^+$).

3. Synthesis of ethyl 2-(4-aminophenyl)quinazoline-4-carboxylate

Into a 100-mL 3-necked round-bottom flask purged and maintained with an inert atmosphere of nitrogen, was placed ethyl 2-(4-nitrophenyl)quinazoline-4-carboxylate (1.2 g, 3.71 mmol, 1.00 equiv), water (13 mL), sodium hydroxide (150 mg, 3.75 mmol, 2.00 equiv) and sodium hyposulfite (1.3 g, 2.00 equiv). The resulting solution was stirred for 12 h at 80° C. in an oil bath. The solids were filtered out. The filter cake was washed with 1×50 mL of ethanol. The resulting mixture was concentrated under vacuum. The residue was applied onto a silica gel column with ethyl acetate/petroleum ether (1:5). This resulted in 0.8 g (73%) of ethyl 2-(4-aminophenyl)quinazoline-4-carboxylate as a yellow solid. MS (ESI) m/z 294 ([M+H]$^+$).

4. Synthesis of 2-(4-aminophenyl)quinazoline-4-carboxylic acid

Into a 50-mL 3-necked round-bottom flask purged and maintained with an inert atmosphere of nitrogen, was placed ethyl 2-(4-aminophenyl)quinazoline-4-carboxylate (300 mg, 1.02 mmol, 1.00 equiv), LiOH (85 mg, 3.55 mmol, 2.00 equiv), tetrahydrofuran (5 mL) and water (5 mL). The resulting solution was stirred for 2 h at room temperature. To this was added 122.4 mg of acetic acid. The resulting solution was concentrated under vacuum. This resulted in 25.3 mg (9%) of 2-(4-aminophenyl)quinazoline-4-carboxylic acid as a yellow solid. MS (ESI) m/z 266 ([M+H]$^+$).

5. Synthesis of 2-(4-acetamidophenyl)quinazoline-4-carboxylic acid

Into a 50-mL 3-necked round-bottom flask purged and maintained with an inert atmosphere of nitrogen, was placed 2-(4-aminophenyl)quinazoline-4-carboxylic acid (25.3 mg, 0.95 mmol, 1.00 equiv), acetyl acetate (18.36 mg, 0.18 mmol, 2.00 equiv), potassium hydroxide (5.07 mg, 1.00 equiv) and tetrahydrofuran (10 mL). The resulting solution was stirred for 5 h at room temperature. The resulting mixture was concentrated under vacuum. The residue was applied onto a silica gel column with ethyl acetate/petroleum ether (1:3). This resulted in 20 mg (68%) of 2-(4-acetamidophenyl)quinazoline-4-carboxylic acid as a yellow solid. MS (ESI) m/z 308 ([M+H]$^+$).

I-13. Synthesis of 2-(4-nitrophenyl)quinazoline-4-carboxylic acid 2-(4-Nitrophenyl)quinazoline-4-carboxylic acid was prepared from ethyl 2-(4-nitrophenyl)quinazoline-4-carboxylate as outlined in Scheme 5.

Scheme 5

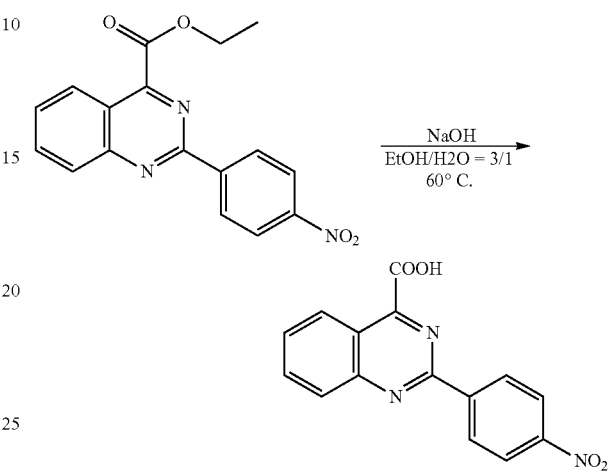

Into a 2-L 3-necked round-bottom flask, was placed a solution of ethyl 2-(4-nitrophenyl)quinazoline-4-carboxylate (100 g, 309.31 mmol, 1.00 equiv) in ethanol (1 L). This was followed by the addition of a solution of sodiumol (62 g, 1.55 mol, 5.00 equiv) in $H_2O$ (350 mL) dropwise with stirring at room temperature. The resulting solution was stirred overnight at 55° C. in an oil bath. The resulting mixture was concentrated under vacuum. The resulting solution was diluted with 300 mL of $H_2O$. The pH value of the solution was adjusted to 2 with hydrogen chloride (5 mol/L). The solids were collected by filtration. This resulted in 80 g (88%) of 2-(4-nitrophenyl)quinazoline-4-carboxylic acid as a light yellow solid. $^1H$ NMR (300 MHz, DMSO-$d_6$) δ 7.84-7.89 (m, 1H), 8.11-8.21 (m, 2H), 8.40-8.45 (m, 3H), 8.75-8.78 (m, 2H); MS (ESI) m/z 296 ([M+H]$^+$).

I-14. Synthesis of 2-[4-(acetamidomethyl)phenyl]quinazoline-4-carboxylic acid 2-[4-(Acetamidomethyl)phenyl]quinazoline-4-carboxylic acid was prepared from 4-(aminomethyl)benzoic acid as outlined in Scheme 6

Scheme 6

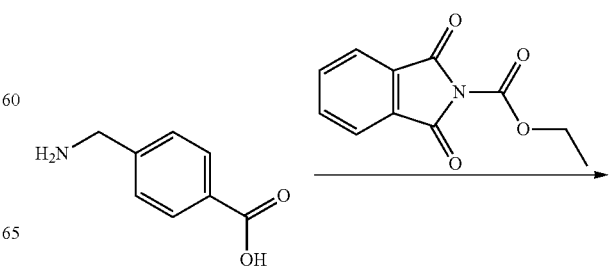

-continued

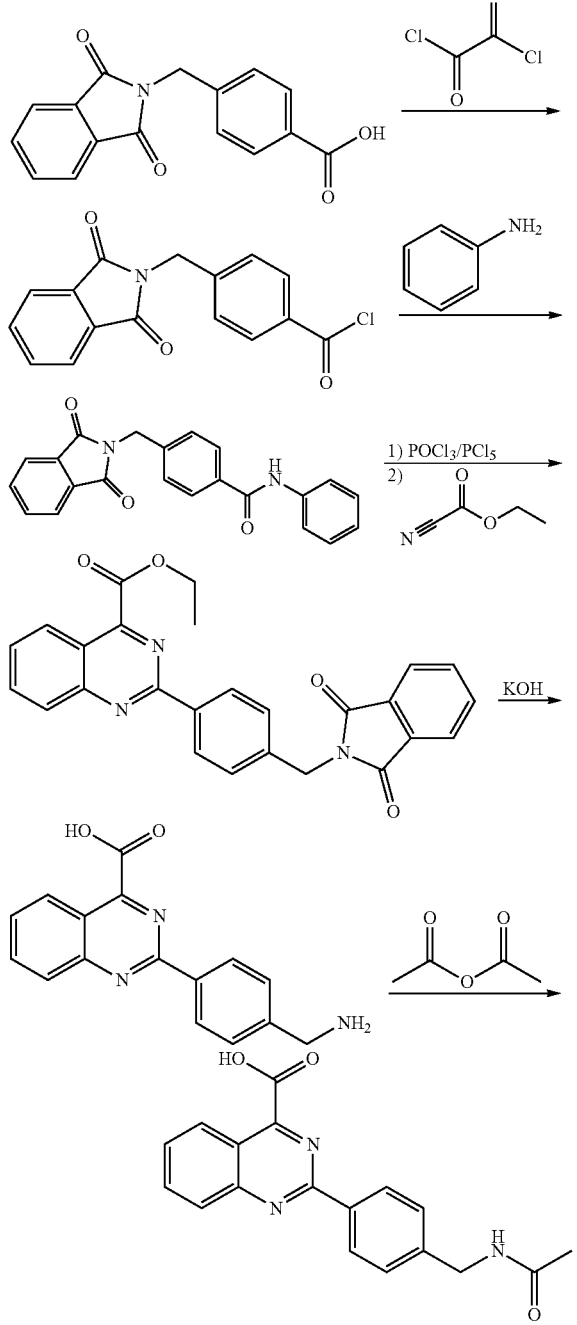

1. Synthesis of 4-[(1,3-dioxo-2,3-dihydro-1H-isoindol-2-yl)methyl]benzoic acid

Into a 250-mL 3-necked round-bottom flask, was placed sodium carbonate (3.7 g, 34.91 mmol, 0.54 equiv), water (66 mL), 4-(aminomethyl)benzoic acid (9.7 g, 64.17 mmol, 1.00 equiv) and ethyl 1,3-dioxo-2,3-dihydro-1H-isoindole-2-carboxylate (14.6 g, 66.61 mmol, 1.04 equiv). The resulting solution was stirred for 3 h at 25° C. The pH value of the solution was adjusted to 4 with hydrogen chloride (1 mol/L). The solids were collected by filtration. The filter cake was washed with 1×100 mL of water. This resulted in 15.7 g (87%) of 4-[(1,3-dioxo-2,3-dihydro-1H-isoindol-2-yl)methyl]benzoic acid as a white solid. MS (ESI) m/z 282 ([M+H]$^+$).

2. Synthesis of 4-[(1,3-dioxo-2,3-dihydro-1H-isoindol-2-yl)methyl]benzoyl chloride Into a 500-mL 3-necked round-bottom flask purged and maintained with an inert atmosphere of nitrogen, was placed 4-[(1,3-dioxo-2,3-dihydro-1H-isoindol-2-yl)methyl]benzoic acid (15.7 g, 55.82 mmol, 1.00 equiv), dichloromethane (200 mL), oxalic dichloride (10.56 g, 83.20 mmol, 1.49 equiv) and dimethylforamide (cat.). The resulting solution was stirred for 2 h at 25° C. The resulting mixture was concentrated under vacuum. This resulted in 16.7 g (crude) of 4-[(1,3-dioxo-2,3-dihydro-1H-isoindol-2-yl)methyl]benzoyl chloride as a white solid. R$_f$: 0.30 (in ethyl acetate:petroleum ether=1:5).

3. Synthesis of 4-[(1,3-dioxo-2,3-dihydro-1H-isoindol-2-yl)methyl]-N-phenylbenzamide Into a 500-mL 3-necked round-bottom flask purged and maintained with an inert atmosphere of nitrogen, was placed aniline (5.73 g, 61.53 mmol, 1.10 equiv), dichloromethane (100 mL) and triethylamine (11.3 g, 111.67 mmol, 2.00 equiv). This was followed by the addition of 4-[(1,3-dioxo-2,3-dihydro-1H-isoindol-2-yl)methyl]benzoyl chloride (16.7 g, 55.72 mmol, 1.00 equiv) in dichloromethane (100 mL) dropwise with stirring at 0° C. The resulting solution was stirred for 3 h at 25° C. The resulting solution was diluted with 100 mL of hexane. The solids were collected by filtration. The filter cake was washed with 2×50 mL of HCl (1 M), 2×50 mL of saturated aqueous Na$_2$CO$_3$ and 2×100 mL of water. This resulted in 14 g (71%) of 4-[(1,3-dioxo-2,3-dihydro-1H-isoindol-2-yl)methyl]-N-phenylbenzamide as a white solid. MS (ESI) m/z 357 ([M+H]$^+$).

4. Synthesis of ethyl 2-[4-[(1,3-dioxo-2,3-dihydro-1H-isoindol-2-yl)methyl]phenyl]quinazoline-4-carboxylate Into a 500-mL round-bottom flask purged and maintained with an inert atmosphere of nitrogen, was placed 4-[(1,3-dioxo-2,3-dihydro-1H-isoindol-2-yl)methyl]-N-phenylbenzamide (14 g, 39.28 mmol, 1.00 equiv), POCl$_3$ (140 mL) and PCl$_5$ (8.96 g, 43.03 mmol, 1.10 equiv). The resulting solution was stirred for 2 h at 65° C. in an oil bath. The resulting mixture was concentrated under vacuum. The residue was diluted with chlorobenzene (300 mL). To this was added 2-ethoxy-2-oxoacetonitrile (7.7 mL, 2.00 equiv), tetrachlorostannane (15 mL, 1.50 equiv). The resulting solution was allowed to react, with stirring, for an additional 2 h while the temperature was maintained at 120° C. in an oil bath. The resulting mixture was concentrated under vacuum. The residue was applied onto a silica gel column with ethyl acetate:petroleum ether:tetrahydrofuran (30:6:1). This resulted in 4 g (23%) of ethyl 2-[4-[(1,3-dioxo-2,3-dihydro-1H-isoindol-2-yl)methyl]phenyl]quinazoline-4-carboxylate as a light yellow solid. MS (ESI) m/z 438 ([M+H]$^+$).

5. Synthesis of 2-[4-(aminomethyl)phenyl]quinazoline-4-carboxylic acid

Into a 500-mL round-bottom flask, was placed ethyl 2-[4-[(1,3-dioxo-2,3-dihydro-1H-isoindol-2-yl)methyl]phenyl]quinazoline-4-carboxylate (4 g, 9.14 mmol, 1.00 equiv), ethanol (40 mL) and 1N KOH (70 mL). The resulting solution was stirred for 24 h at 100° C. in an oil bath. The pH value of the solution was adjusted to 7 with acetic acid. The resulting mixture was concentrated under vacuum. This resulted in 2.6 g (crude) of 2-[4-(aminomethyl)phenyl]quinazoline-4-carboxylic acid as a white solid. MS (ESI) m/z 280 ([M+H]$^+$).

6. Synthesis of 2-[4-(acetamidomethyl)phenyl]quinazoline-4-carboxylic acid

Into a 500-mL round-bottom flask purged and maintained with an inert atmosphere of nitrogen, was placed 2-[4-(aminomethyl)phenyl]quinazoline-4-carboxylic acid (2.6 g, 9.31 mmol, 1.00 equiv), oxolane (200 mL) and acetyl acetate (20 mL). The resulting solution was stirred for 3 h at 25° C. The resulting mixture was concentrated under vacuum. The residue was applied onto a silica gel column with dichloromethane/methanol (20:1-5:1). This resulted in 500 mg (17%) of 2-[4-(acetamidomethyl)phenyl]quinazoline-4-carboxylic acid as a light yellow solid. MS (ESI) m/z 322 ([M+H]$^+$).

I-15. Synthesis of 2-(pyrimidin-4-yl)quinazoline-4-carboxylic acid 2-(Pyrimidin-4-yl)quinazoline-4-carboxylic acid was prepared from (E)-N-(pyrimidin-4-ylmethylidene)hydroxylamine and 1-(2-bromophenyl)ethan-1-one as outlined in Scheme 7.

2. Synthesis of pyrimidine-4-carboximidamide

Into a 250-mL 3-necked round-bottom flask purged and maintained with an inert atmosphere of nitrogen, was placed a solution of Na (0.11 g) in methanol (100 mL). The mixture was stirred for 10 min. This was followed by the addition of pyrimidine-4-carbonitrile (10 g, 95.15 mmol, 1.00 equiv). The solution was stirred for 2 h at room temperature. To this was added NH$_4$Cl (11 g, 205.65 mmol, 2.16 equiv). The resulting solution was stirred for 4 h at 25° C. The resulting mixture was concentrated under vacuum. The residue was dissolved in 100 mL of ethanol. The mixture was stirred for 10 min under reflux. The solids were filtered out. The filtrate was concentrated under vacuum. The solids were collected by filtration. This resulted in 5 g (33%) of pyrimidine-4-carboximidamide hydrochloride as a white solid. MS (ESI) m/z 123 ([M+H]$^+$).

3. Synthesis of 2-(2-bromophenyl)-2-oxoacetic acid

Into a 250-mL 3-necked round-bottom flask purged and maintained with an inert atmosphere of nitrogen, was placed a solution of 1-(2-bromophenyl)ethan-1-one (10 g, 50.24 mmol, 1.00 equiv) in pyridine (80 mL). This was followed by the addition of SeO$_2$ (22 g, 198.27 mmol, 3.95 equiv). The resulting solution was stirred for 18 h at 120° C. in an oil bath. The reaction mixture was cooled to room temperature. The solids were filtered out. The resulting mixture was concen- Scheme 7

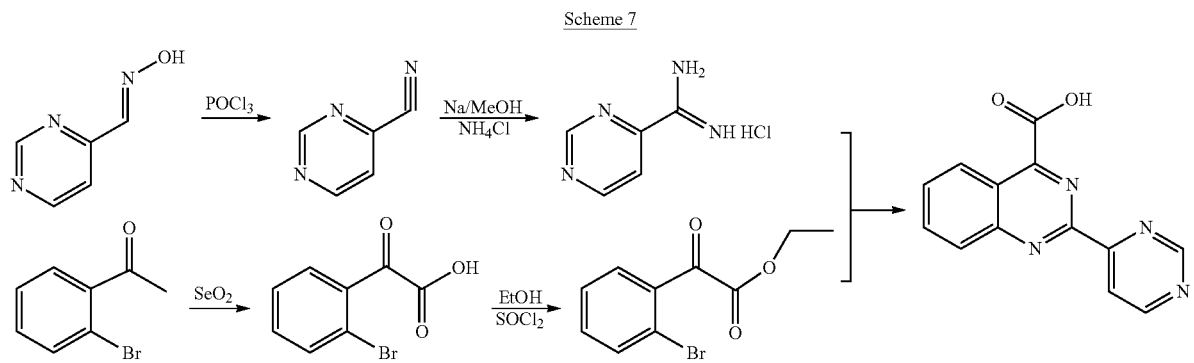

1. Synthesis of pyrimidine-4-carbonitrile

Into a 500-mL 3-necked round-bottom flask purged and maintained with an inert atmosphere of nitrogen, was placed a solution of (E)-N-(pyrimidin-4-ylmethylidene)hydroxylamine (26 g, 211.19 mmol, 1.00 equiv) in chloroform (200 mL). This was followed by the addition of POCl$_3$ (128 g, 834.80 mmol, 3.95 equiv). The resulting solution was stirred for 1 h at 120° C. in an oil bath. The reaction was then quenched by the addition of 100 mL of water/ice. The pH value of the solution was adjusted to 8 with saturated aqueous Na$_2$CO$_3$. The resulting solution was extracted with 3×300 mL of ethyl acetate and the organic layers combined and dried over anhydrous sodium sulfate. The solids were filtered out. The resulting mixture was concentrated under vacuum. The residue was applied onto a silica gel column with ethyl acetate/petroleum ether (1:5). This resulted in 10 g (45%) of pyrimidine-4-carbonitrile as yellow oil. R$_f$: 0.29 (in ethyl acetate:petroleum ether=1:1).

trated under vacuum. The residue was dissolved in 100 mL of water. The resulting mixture was washed with 2×50 mL of ethyl acetate. The pH value of the aqueous layer was adjusted to 1-2 with hydrogen chloride (4 mol/L). The resulting solution was extracted with 3×80 mL of ethyl acetate and the organic layers combined and dried over anhydrous sodium sulfate. The solids were filtered out. The resulting mixture was concentrated under vacuum. This resulted in 10 g (87%) of 2-(2-bromophenyl)-2-oxoacetic acid as yellow oil. MS (ESI) m/z 230 ([M+H]$^+$).

4. Synthesis of ethyl 2-(2-bromophenyl)-2-oxoacetate

Into a 250-mL 3-necked round-bottom flask, was placed a solution of 2-(2-bromophenyl)-2-oxoacetic acid (10 g, 43.66 mmol, 1.00 equiv) in ethanol (80 mL). This was followed by the addition of thionyl chloride (20 mL) dropwise with stirring. The resulting solution was stirred for 12 h at 80° C. in an oil bath. The resulting mixture was concentrated under vacuum. The residue was dissolved in 100 mL of ethyl acetate. The resulting mixture was washed with 2×50 mL of water. The mixture was dried over anhydrous sodium sulfate. The residue was applied onto a silica gel column with ethyl acetate/petroleum ether (1:5). This resulted in 9 g (80%) of ethyl 2-(2-bromophenyl)-2-oxoacetate as yellow oil. MS (ESI) m/z 258 ([M+H]$^+$).

5. Synthesis of 2-(pyrimidin-4-yl)quinazoline-4-carboxylic acid

Into a 250-mL 3-necked round-bottom flask purged and maintained with an inert atmosphere of nitrogen, was placed a solution of ethyl 2-(2-bromophenyl)-2-oxoacetate (9 g, 35.01 mmol, 1.00 equiv) in N,N-dimethylformamide (60 mL). This was followed by the addition of pyrimidine-4-carboximidamide hydrochloride (5.53 g, 45.03 mmol, 1.29 equiv) and Cs$_2$CO$_3$ (11.38 g, 34.93 mmol, 1.00 equiv). The mixture was stirred for 20 min. To this was added L-proline (850 mg, 7.39 mmol, 0.21 equiv) and CuI (670 mg, 3.53 mmol, 0.10 equiv). The resulting solution was stirred for 2.5 h at 95° C. The reaction mixture was cooled to room temperature. The resulting mixture was concentrated under vacuum. The residue was dissolved in 50 mL of water. The solids were filtered out. The filtrate was washed with 2×50 mL of ethyl acetate. The pH value of the aqueous layer was adjusted to 5 with hydrogen chloride (2 mol/L). The resulting mixture was concentrated under vacuum. The crude product was purified by Flash. This resulted in 0.5 g (6%) of 2-(pyrimidin-4-yl)quinazoline-4-carboxylic acid as dark brown oil. MS (ESI) m/z 253 ([M+H]$^+$).

I-16. Synthesis of 2-(2-aminoethyl)quinazoline-4-carboxylic acid 2-(2-Aminoethyl)quinazoline-4-carboxylic acid was prepared from 3-aminopropanoic acid and 1,3-dihydro-2-benzofuran-1,3-dione as outlined in Scheme 8.

Scheme 8

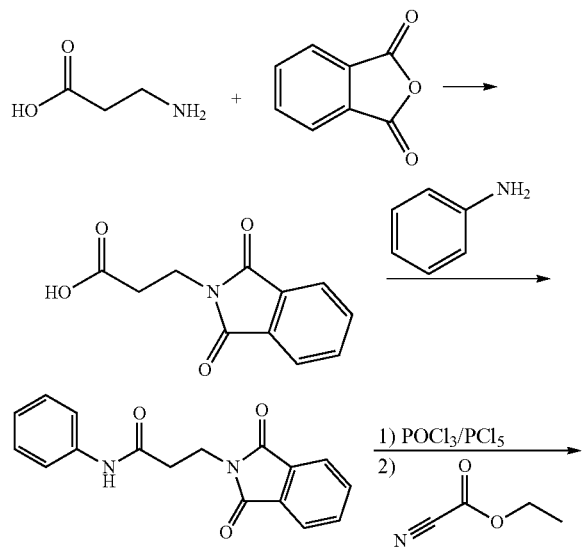

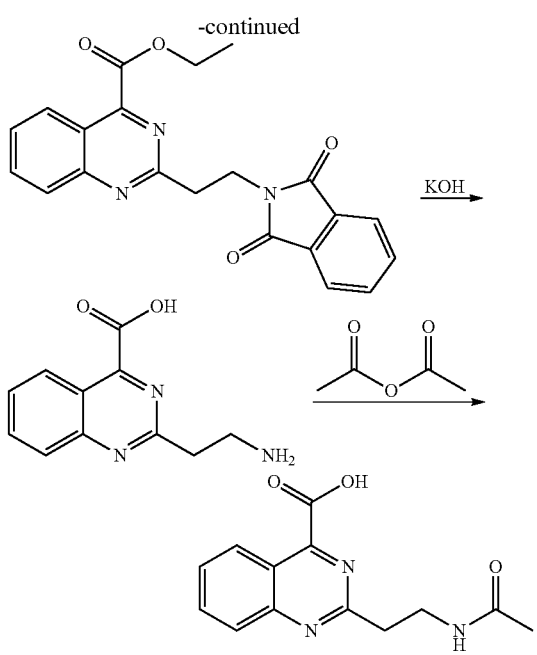

1. Synthesis of 3-(1,3-dioxo-2,3-dihydro-1H-isoindol-2-yl)propanoic acid

Into a 3-L 4-necked round-bottom flask purged and maintained with an inert atmosphere of nitrogen, was placed a solution of 3-aminopropanoic acid (20 g, 224.48 mmol, 1.00 equiv) and 1,3-dihydro-2-benzofuran-1,3-dione (33.28 g, 224.69 mmol, 1.00 equiv) in acetic acid (1,200 mL). This was followed by the addition of potassium acetate (66.0 g, 672.49 mmol, 3.00 equiv) in several batches at 0° C. The resulting solution was stirred for 3 h at 80° C. in an oil bath. The resulting mixture was concentrated under vacuum. The reaction was then quenched by the addition of 150 mL of water. The solids were collected by filtration. This resulted in 40 g (81%) of 3-(1,3-dioxo-2,3-dihydro-1H-isoindol-2-yl)propanoic acid as a white solid. R$_f$: 0.15 (in ethyl acetate:petroleum ether=1:1).

2. Synthesis of 3-(1,3-dioxo-2,3-dihydro-1H-isoindol-2-yl)-N-phenylpropanamide Into a 1000-mL 4-necked round-bottom flask purged and maintained with an inert atmosphere of nitrogen, was placed a solution of 3-(1,3-dioxo-2,3-dihydro-1H-isoindol-2-yl)propanoic acid (40 g, 182.49 mmol, 1.00 equiv) in water (250 mL). This was followed by the addition of aniline (17 g, 182.55 mmol, 1.00 equiv). To this was added sodium carbonate (9.6 g, 90.57 mmol, 0.50 equiv). The resulting solution was stirred for 3 h at 25° C. The pH value of the solution was adjusted to 5-6 with hydrochloric acid (1 mol/L). The solids were collected by filtration. The filter cake was washed with 1×200 mL of water. This resulted in 40 g (74%) of 3-(1,3-dioxo-2,3-dihydro-1H-isoindol-2-yl)-N-phenylpropanamide as a white solid. MS (ESI) m/z 295 ([M+H]$^+$).

3. Synthesis of ethyl 2-[2-(1,3-dioxo-2,3-dihydro-1H-isoindol-2-yl)ethyl]quinazoline-4-carboxylate Into a 2000-mL 4-necked round-bottom flask purged and maintained with an inert atmosphere of nitrogen, was placed a solution of 3-(1,3-dioxo-2,3-dihydro-1H-isoindol-2-yl)-N-phenylpropanamide (40 g, 135.91 mmol, 1.00 equiv) in POCl₃ (300 mL). This was followed by the addition of PCl₅ (30 g, 144.06 mmol, 1.06 equiv). The mixture was stirred for 2 h at 65° C. The resulting mixture was concentrated under vacuum. The residue was poured into chlorobenzene (500 mL). To this was added SnCl₄ (53 g) and 2-ethoxy-2-oxoacetonitrile (26 g, 262.39 mmol, 1.93 equiv) dropwise with stirring. The resulting solution was stirred for 2 h at 120° C. in an oil bath. The reaction mixture was cooled to room temperature. The resulting mixture was concentrated under vacuum. The residue was applied onto a silica gel column with ethyl acetate/petroleum ether (1:5). This resulted in 7.0 g (14%) of ethyl 2-[2-(1,3-dioxo-2,3-dihydro-1H-isoindol-2-yl)ethyl]quinazoline-4-carboxylate as a white solid. MS (ESI) m/z 376 ([M+H]⁺).

4. Synthesis of 2-(2-aminoethyl)quinazoline-4-carboxylic acid

Into a 250-mL 4-necked round-bottom flask, was placed ethyl 2-[2-(1,3-dioxo-2,3-dihydro-1H-isoindol-2-yl)ethyl]quinazoline-4-carboxylate (7 g, 18.65 mmol, 1.00 equiv). This was followed by the addition of KOH (20.9 g, 372.51 mmol, 19.98 equiv) in water (20 mL) dropwise with stirring. The resulting solution was stirred for 18 h at 100° C. The reaction was then poured into 250 mL of water. The pH value of the solution was adjusted to 7 with hydrogen chloride (2 mol/L). The resulting solution was extracted with 5×100 mL of ethyl acetate and the organic layers combined. The mixture was dried over anhydrous sodium sulfate and concentrated under vacuum. This resulted in 3.2 g (79%) of 2-(2-aminoethyl)quinazoline-4-carboxylic acid as a white solid. MS (ESI) m/z 218 ([M+H]⁺).

5. Synthesis of 2-(2-acetamidoethyl)quinazoline-4-carboxylic acid

Into a 500-mL 4-necked round-bottom flask purged and maintained with an inert atmosphere of nitrogen, was placed a solution of 2-(2-aminoethyl)quinazoline-4-carboxylic acid (3.2 g, 14.73 mmol, 1.00 equiv) in tetrahydrofuran (32 mL). This was followed by the addition of acetyl acetate (32 mL) dropwise with stirring at room temperature. The resulting solution was stirred for 18 h at room temperature. The reaction was then quenched by the addition of 50 mL of water. The mixture was concentrated under vacuum. The crude product was purified by Flash. This resulted in 900 mg (24%) of 2-(2-acetamidoethyl)quinazoline-4-carboxylic acid as a white solid. MS (ESI) m/z 260 ([M+H]⁺).

I-17. Synthesis of 2-(1,3-thiazol-4-yl)quinazoline-4-carboxylic acid 2-(1,3-Thiazol-4-yl)quinazoline-4-carboxylic acid was obtained by the same way with the preparation of 2-(4-(dimethylamino)phenyl)quinazoline-4-carboxylic acid (last step yield 40%) as a white solid. MS (ESI) m/z 258 ([M+H]⁺).

I-18. Synthesis of 2-(pyridin-3-yl)quinazoline-4-carboxylic acid 2-(Pyridin-3-yl)quinazoline-4-carboxylic acid was obtained by the same way with the preparation of 2-(4-fluorophenyl)quinazoline-4-carboxylic acid (last step yield 32%) as a light yellow solid. MS (ESI) m/z 252 ([M+H]⁺).

I-19. Synthesis of 2-(3,4,5-trimethoxyphenyl)quinazoline-4-carboxylic acid 2-(3,4,5-Trimethoxyphenyl)quinazoline-4-carboxylic acid was prepared from 2-aminobenzonitrile and 3,4,5-trimethoxybenzoyl chloride as outlined in Scheme 9.

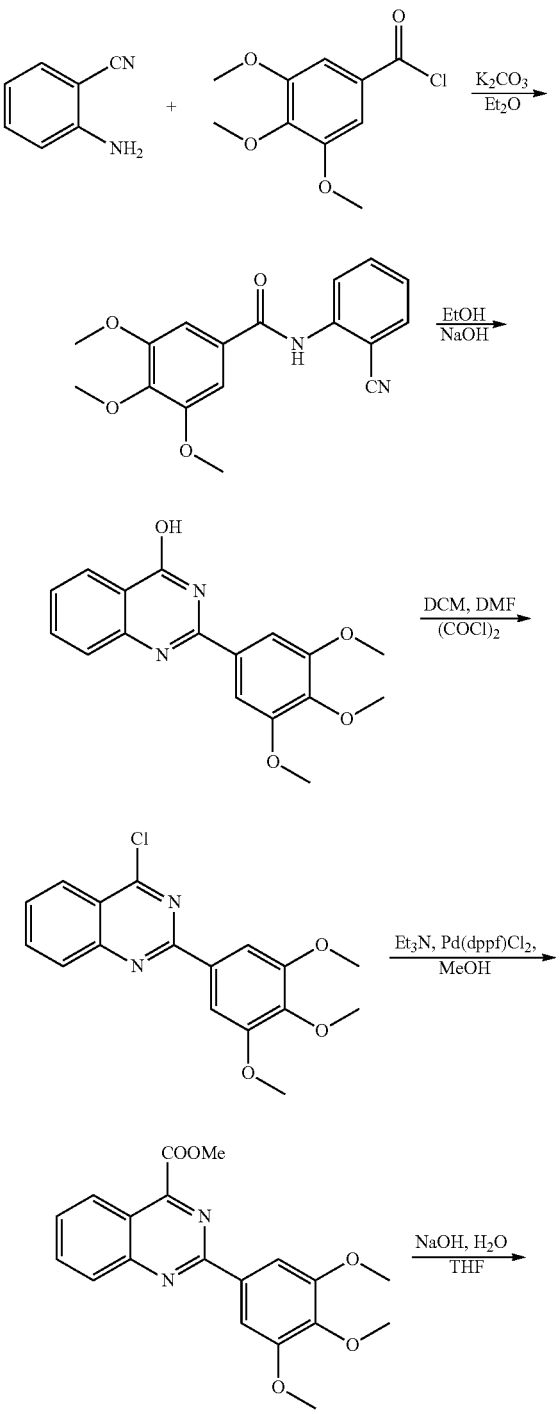

Scheme 9

-continued

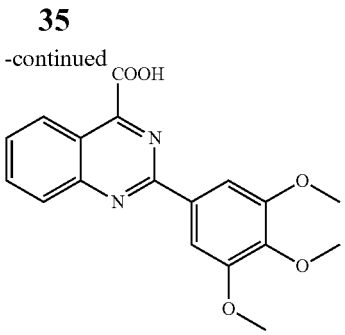

1. Synthesis of N-(2-cyanophenyl)-3,4,5-trimethoxybenzamide

Into a 1-L 3-necked round-bottom flask, was placed 2-aminobenzonitrile (20 g, 169.30 mmol, 1.00 equiv), ether (500 mL) and potassium carbonate (75 g, 542.65 mmol, 3.21 equiv). This was followed by the addition of 3,4,5-trimethoxybenzoyl chloride (40 g, 173.43 mmol, 1.02 equiv) in several batches at reflux. The mixture was stirred overnight at reflux. The resulting solution was cooled to room temperature. The reaction was then quenched by the addition of 500 mL of water. The solids were collected by filtration. This resulted in 22 g (42%) of N-(2-cyanophenyl)-3,4,5-trimethoxybenzamide as a yellow solid. MS (ESI) m/z 313 ([M+H]$^+$).

2. Synthesis of 2-(3,4,5-trimethoxyphenyl)quinazolin-4-ol

Into a 1-L 3-necked round-bottom flask, was placed a solution of N-(2-cyanophenyl)-3,4,5-trimethoxybenzamide (22 g, 70.44 mmol, 1.00 equiv) in ethanol (200 mL), $H_2O_2$ (200 mL) and sodium hydroxide (200 mL, 20%). The resulting solution was stirred for 16 h at room temperature. The resulting mixture was concentrated under vacuum. The reaction was then quenched by the addition of 500 mL of water. The solids were collected by filtration. This resulted in 12 g (55%) of 2-(3,4,5-trimethoxyphenyl)quinazolin-4-ol as a white solid. MS (ESI) m/z 313 ([M+H]$^+$).

3. Synthesis of 4-chloro-2-(3,4,5-trimethoxyphenyl)quinazoline

Into a 1-L 3-necked round-bottom flask, was placed 2-(3,4,5-trimethoxyphenyl)quinazolin-4-ol (12 g, 38.5 mmol, 1.00 equiv), dichloromethane (500 mL) and N,N-dimethylformamide (0.5 mL). This was followed by the addition of (COCl)$_2$ (15 g) dropwise with stirring at 0° C. The resulting solution was heated to reflux for 1 h in an oil bath. The reaction was then quenched by the addition of 50 mL of sodium bicarbonate (sat.). The resulting solution was extracted with 2×100 mL of dichloromethane and the organic layers combined. The mixture was dried over anhydrous sodium sulfate and concentrated under vacuum. The residue was applied onto a silica gel column with ethyl acetate:dichloromethane:petroleum ether (1:1:4). This resulted in 10 g (78.7%) of 4-chloro-2-(3,4,5-trimethoxyphenyl)quinazoline as a white solid. MS (ESI) m/z 332 ([M+H]$^+$).

4. Synthesis of methyl 2-(3,4,5-trimethoxyphenyl) quinazoline-4-carboxylate

Into a 250-mL pressure tank reactor (20 atm), was placed 4-chloro-2-(3,4,5-trimethoxyphenyl)quinazoline (1.7 g, 5.14 mmol, 1.00 equiv), methanol (200 ml), triethylamine (1 g, 9.88 mmol, 1.92 equiv) and Pd(dppf)Cl$_2$ (300 mg, 0.41 mmol, 0.08 equiv). To the above CO (20 atm) was introduced in. The resulting solution was stirred overnight at 100° C. The resulting mixture was concentrated under vacuum. The residue was diluted with 50 ml of water. The resulting solution was extracted with 3×50 mL of dichloromethane and the organic layers combined. The mixture was dried over anhydrous sodium sulfate and concentrated under vacuum. The residue was applied onto a silica gel column with ethyl acetate:dichloromethane:petroleum ether (1:1:3). This resulted in 1.0 g (55%) of methyl 2-(3,4,5-trimethoxyphenyl)quinazoline-4-carboxylate as a yellow solid. MS (ESI) m/z 355 ([M+H]$^+$).

5. Synthesis of 2-(3,4,5-trimethoxyphenyl)quinazoline-4-carboxylic acid

Into a 250-mL 3-necked round-bottom flask, was placed methyl 2-(3,4,5-trimethoxyphenyl)quinazoline-4-carboxylate (1.7 g, 4.80 mmol, 1.00 equiv), methanol (10 mL) and sodium hydroxide (20%, 10 mL). The resulting solution was stirred for 30 min at 75° C. The pH value of the solution was adjusted to 2 with hydrogen chloride (1 mol/L). The resulting solution was extracted with 2×50 mL of dichloromethane and the organic layers combined. The mixture was dried over anhydrous sodium sulfate and concentrated under vacuum. This resulted in 0.8 g (49%) of 2-(3,4,5-trimethoxyphenyl) quinazoline-4-carboxylic acid as a yellow solid. $^1$H NMR (400 MHz, CDCl$_3$) δ 3.99 (s, 3H), 4.06 (s, 6H), 7.77-7.81 (m, 1H), 7.84 (s, 2H), 8.03-8.07 (m, 1H), 8.22 (d, 1H), 9.41 (d, 1H); MS (ESI) m/z 341 ([M+H]$^+$).

I-20. Synthesis of 6-fluoro-2-(4-fluorophenyl) quinazoline-4-carboxylic acid 6-Fluoro-2-(4-fluorophenyl)quinazoline-4-carboxylic acid was obtained by the same way with the preparation of 2-(4-fluorophenyl)quinazoline-4-carboxylic acid (last step yield 90%) as a yellow solid. $^1$H NMR (400 MHz, DMSO-d$_6$) δ 7.38-7.44 (m, 1H), 7.59-7.66 (m, 1H), 7.92-8.04 (m, 2H), 8.13-8.25 (m, 2H), 8.36-8.39 (d, 1H); MS (ESI) m/z 287 ([M+H]$^+$).

I-21. Synthesis of 6-fluoro-2-(3,4,5-trimethoxyphenyl)quinazoline-4-carboxylic acid 6-Fluoro-2-(3,4,5-trimethoxyphenyl)quinazoline-4-carboxylic acid was prepared from 5-fluoro-2-nitrobenzoic acid as outlined in Scheme 10.

Scheme 10

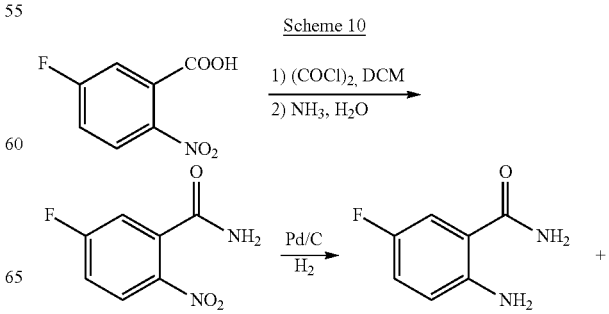

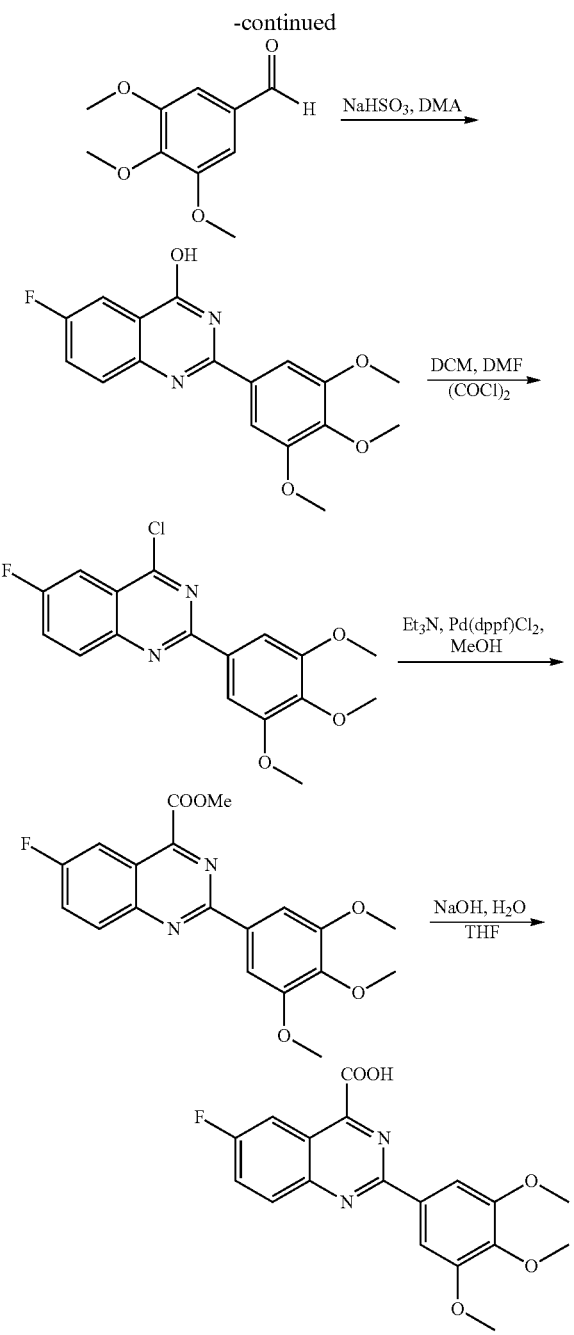

1. Synthesis of 5-fluoro-2-nitrobenzamide

Into a 1-L 3-necked round-bottom flask, was placed 5-fluoro-2-nitrobenzoic acid (25 g, 135.06 mmol, 1.00 equiv), dichloromethane (400 mL) and N,N-dimethylformamide (0.1 g). This was followed by the addition of (COCl)$_2$ (30 g) dropwise with stirring at 0-10° C. The resulting solution was stirred overnight at room temperature. The resulting mixture was concentrated under vacuum. The residue was dissolved in 200 mL of dichloromethane. To this was added ammonia (400 mL) dropwise with stirring at 0-10° C. The resulting solution was stirred for 2 h at room temperature. The solids were collected by filtration. This resulted in 20 g (80%) of 5-fluoro-2-nitrobenzamide as a yellow solid. $^1$H NMR (300 MHz, DMSO-d$_6$) δ 7.71 (s, 1H), 7.81 (s, 1H), 8.00 (s, 1H).

2. Synthesis of 2-amino-5-fluorobenzamide

Into a 500-mL round-bottom flask purged and maintained with an inert atmosphere of nitrogen, was placed a mixture of 5-fluoro-2-nitrobenzamide (17.5 g, 95.04 mmol, 1.00 equiv) and palladium carbon (10%) (1.75 g, 0.10 equiv) in methanol (150 mL). To the above H$_2$ (enough) was introduced. The resulting solution was stirred for 2 h at room temperature. The solids were filtered out. The resulting mixture was concentrated under vacuum. This resulted in 12.0 g (82%) of 2-amino-5-fluorobenzamide as a white solid. MS (ESI) m/z 155 ([M+H]$^+$).

3. Synthesis of 6-fluoro-2-(3,4,5-trimethoxyphenyl)quinazolin-4-ol

Into a 250-mL round-bottom flask, was placed a solution of 2-amino-5-fluorobenzamide (13.02 g, 84.47 mmol, 1.00 equiv) in dimethylacetamide (200 mL), 3,4,5-trimethoxybenzaldehyde (17.97 g, 91.59 mmol, 1.08 equiv) and NaHSO$_3$ (8.85 g). The resulting solution was stirred overnight at 140° C. in an oil bath. The reaction was then quenched by the addition of 400 mL of water/ice. The solids were collected by filtration. This resulted in 28 g (crude) of 6-fluoro-2-(3,4,5-trimethoxyphenyl)quinazolin-4-ol as a brown solid. MS (ESI) m/z 331 ([M+H]$^+$).

4. Synthesis of 4-chloro-6-fluoro-2-(3,4,5-trimethoxyphenyl)quinazoline

Into a 500-mL round-bottom flask, was placed 6-fluoro-2-(3,4,5-trimethoxyphenyl)quinazolin-4-ol (8.0 g, 24.22 mmol, 1.00 equiv), dichloromethane (200 mL) and N,N-dimethylformamide (0.5 mL). This was followed by the addition of (COCl)$_2$ (23.74 g) dropwise with stirring. The resulting solution was stirred for 1 h at 40° C. in an oil bath. The resulting mixture was concentrated under vacuum. The residue was dissolved in 100 mL of dichloromethane. The resulting mixture was washed with 2×100 mL of NaHCO$_3$ (sat.) and 1×100 mL of brine. The mixture was dried over anhydrous sodium sulfate and concentrated under vacuum. The residue was purified by ethyl acetate:petroleum ether in ratio of (1:5). This resulted in 5 g (59%) of 4-chloro-6-fluoro-2-(3,4,5-trimethoxyphenyl)quinazoline as a white solid. MS (ESI) m/z 349 ([M+H]$^+$).

5. Synthesis of methyl 6-fluoro-2-(3,4,5-trimethoxyphenyl)quinazoline-4-carboxylate Into a 250-mL pressure tank reactor (20 atm), was placed 4-chloro-6-fluoro-2-(3,4,5-trimethoxyphenyl)quinazoline (4.5 g, 12.90 mmol, 1.00 equiv), methanol (150 ml), triethylamine (3.3 g, 0.03 mmol, 1.52 equiv) and Pd(dppf)Cl$_2$ (0.4 g, 0.21 equiv). To the above CO (20 atm) was introduced in. The resulting solution was stirred overnight at 100° C. The solid was filtered out. The resulting mixture was concentrated under vacuum. This resulted in 2.0 g (42%) of methyl 6-fluoro-2-(3,4,5-trimethoxyphenyl)quinazoline-4-carboxylate as a yellow solid. MS (ESI) m/z 373 ([M+H]$^+$).

6. Synthesis of 6-fluoro-2-(3,4,5-trimethoxyphenyl)quinazoline-4-carboxylic acid Into a 100-mL round-bottom flask, was placed methyl 6-fluoro-2-(3,4,5-trimethoxyphenyl)quinazoline-4-carboxylate (1.0 g, 2.69 mmol, 1.00 equiv), tetrahydrofuran (10 mL) and sodium hydroxide (10 mL, 20%). The resulting solution was stirred for 0.5 h at room temperature. The resulting mixture was concentrated under vacuum. The resulting solution was diluted with 100 mL of dichloromethane. The pH value of the solution was adjusted to 2 with hydrogen chloride (20%). The solids were collected by filtration. This resulted in 0.6 g (62%) of 6-fluoro-2-(3,4,5-trimethoxyphenyl)quinazoline-4-carboxylic acid as a yellow solid. $^1$H NMR (400 MHz, DMSO-$d_6$) δ 3.75-3.80 (m, 3H), 3.91-3.96 (m, 6H), 7.89 (s, 2H), 8.02-8.07 (m, 1H), 8.22-8.27 (m, 2H); MS (ESI) m/z 359 ([M+H]$^+$).

I-22. Synthesis of 6,7-dimethoxy-2-(4-fluorophenyl) quinazoline-4-carboxylic acid 6,7-Dimethoxy-2-(4-fluorophenyl)quinazoline-4-carboxylic acid was obtained by the same way with the preparation of 2-(4-fluorophenyl)quinazoline-4-carboxylic acid (last step yield 90%). as a yellow solid. $^1$H NMR (300 MHz, DMSO-$d_6$) δ 3.95 (s, 3H), 4.04 (s, 3H), 7.35-7.41 (m, 2H), 7.49 (s, 1H), 7.80 (s, 1H), 8.55-8.60 (m, 2H); MS (ESI) m/z 329 ([M+H]$^+$).

I-23. Synthesis of 6,7-dimethoxy-2-(3,4,5-trimethoxyphenyl)quinazoline-4-carboxylic acid 6,7-Dimethoxy-2-(3,4,5-trimethoxyphenyl)quinazoline-4-carboxylic acid was prepared from 2-amino-4,5-dimethoxybenzoic acid as outlined in Scheme 11.

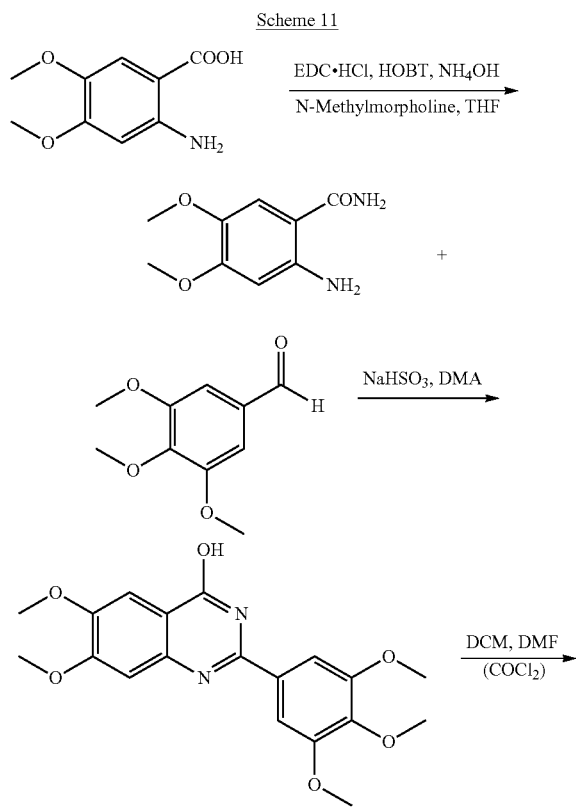

Scheme 11

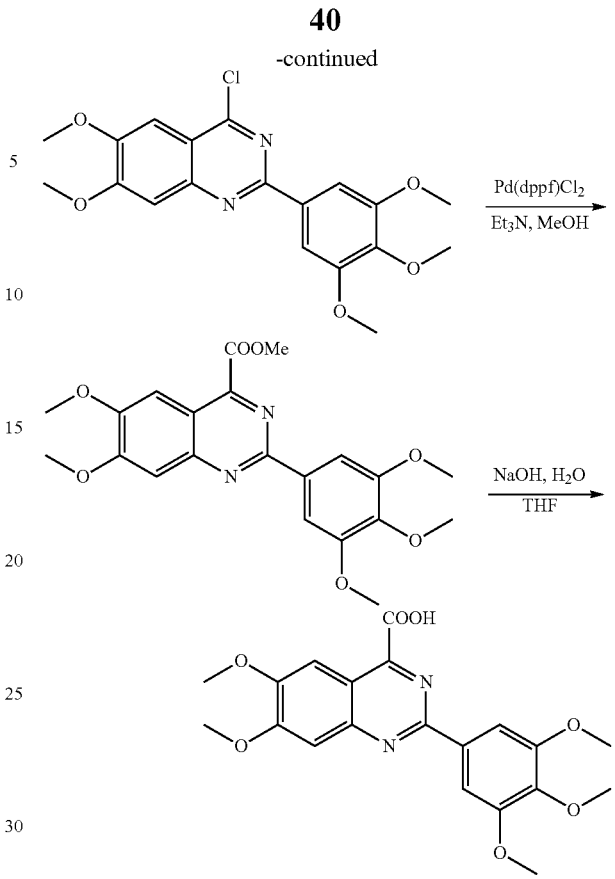

1. Synthesis of 2-amino-4,5-dimethoxybenzamide

Into a 1-L 3-necked round-bottom flask, was placed 2-amino-4,5-dimethoxybenzoic acid (20 g, 101.43 mmol, 1.00 equiv), tetrahydrofuran (400 mL), EDC.HCl (39 g, 203.44 mmol, 2.01 equiv) and HOBt (27.5 g, 203.52 mmol, 2.01 equiv). This was followed by the addition of 4-methylmorpholine (20.6 g, 203.96 mmol, 2.01 equiv) dropwise with stirring at 5-10° C. To this was added ammonia (30 mL) dropwise with stirring at 5-10° C. The resulting solution was stirred overnight at room temperature. The resulting mixture was concentrated under vacuum. The resulting solution was diluted with 300 mL of ethyl acetate. The resulting mixture was washed with 1×300 mL of brine. The aqueous layer was extracted with 5×100 mL of ethyl acetate and the organic layers combined. The mixture was dried over anhydrous sodium sulfate and concentrated under vacuum. This resulted in 12 g (crude, 61.2% yield) of 2-amino-4,5-dimethoxybenzamide as a yellow solid. MS (ESI) m/z 197 [M+H]$^+$ 2. Synthesis of 6,7-dimethoxy-2-(3,4,5-trimethoxyphenyl)quinazolin-4-ol Into a 500-mL 3-necked round-bottom flask, was placed 2-amino-4,5-dimethoxybenzamide (12 g, 61.16 mmol, 1.00 equiv), dimethylacetamide (200 mL), 3,4,5-trimethoxybenzaldehyde (12 g, 61.16 mmol, 1.00 equiv) and NaHSO$_3$ (9.55 g, 91.83 mmol, 1.50 equiv). The resulting solution was stirred overnight at 139° C. The mixture was cooled to room temperature. The resulting solution was diluted with 800 mL of water. The solids were collected by filtration. The filter cake was washed with 1×100 ml of water, 100 ml of diethyl ether and 100 mL of methanol. This resulted in 12 g (53%) of 6,7-dimethoxy-2-(3,4,5-trimethoxyphenyl)quinazolin-4-ol as a brown solid. MS (ESI) m/z 373 [M+h]+

3. Synthesis of 4-chloro-6,7-dimethoxy-2-(3,4,5-trimethoxyphenyl)quinazoline Into a 1-L 3-necked round-bottom flask, was placed 6,7-dimethoxy-2-(3,4,5-trimethoxyphenyl)quinazolin-4-ol (12 g, 32.23 mmol, 1.00 equiv), dichloromethane (400 mL) and DMF (cat.) (0.1 g). This was followed by the addition of (COCl)$_2$ (40 g, 315.21 mmol, 9.78 equiv) dropwise with stirring at 0-10° C. The resulting solution was heated to reflux for 5 h. The mixture was cooled to room temperature. The solids were filtered out. The resulting mixture was concentrated under vacuum. The residue was dissolved in 400 mL of dichloromethane. The resulting mixture was washed with 2×200 mL of NaHCO$_3$ (sat.) and 1×200 mL of brine. The mixture was dried over anhydrous sodium sulfate and concentrated under vacuum. The residue was applied onto a silica gel column with dichloromethane/ethyl acetate (2:1). This resulted in 5 g (40%) of 4-chloro-6,7-dimethoxy-2-(3,4,5-trimethoxyphenyl)quinazoline as a yellow solid. MS (ESI) m/z 391 [M+H]+

4. Synthesis of methyl 6,7-dimethoxy-2-(3,4,5-trimethoxyphenyl)quinazoline-4-carboxylate Into a 250-mL pressure tank reactor (20 atm) purged and maintained with an inert atmosphere of nitrogen gas, was placed 4-chloro-6,7-dimethoxy-2-(3,4,5-trimethoxyphenyl)quinazoline (5 g, 12.79 mmol, 1.00 equiv), methanol (150 mL), triethylamine (2.5 g, 24.71 mmol, 1.93 equiv) and Pd(dppf)Cl$_2$ (500 mg, 0.68 mmol, 0.05 equiv). To the above CO (gas) was introduced in. The resulting solution was stirred overnight at 100° C. The resulting mixture was concentrated under vacuum. The residue was applied onto a silica gel column with dichloromethane/ethyl acetate (5:1). This resulted in 2 g (38%) of methyl 6,7-dimethoxy-2-(3,4,5-trimethoxyphenyl)quinazoline-4-carboxylate as a yellow solid. MS (ESI) m/z 415 [M+H]+

5. Synthesis of 6,7-dimethoxy-2-(3,4,5-trimethoxyphenyl)quinazoline-4-carboxylic acid Into a 100-mL round-bottom flask, was placed methyl 6,7-dimethoxy-2-(3,4,5-trimethoxyphenyl)quinazoline-4-carboxylate (2 g, 4.83 mmol, 1.00 equiv) and tetrahydrofuran (30 mL). This was followed by the addition of a solution of sodium hydroxide (1 g, 25.00 mmol, 5.18 equiv) in water (20 mL) dropwise with stirring. The resulting solution was stirred for 2 h at room temperature. The resulting mixture was concentrated under vacuum. The resulting solution was diluted with 100 mL of water. The resulting solution was extracted with 2×50 mL of dichloromethane and the organic layers combined. The pH value of the solution was adjusted to 5 with hydrogen chloride (1 M). The resulting solution was extracted with 3×100 mL of dichloromethane. The solids were filtered out. The mixture was concentrated under vacuum. This resulted in 1 g (52%) of 6,7-dimethoxy-2-(3,4,5-trimethoxyphenyl)quinazoline-4-carboxylic acid as a yellow solid. $^1$H NMR (300 MHz, DMSO-d$_6$) δ 3.77 (s, 3H), 3.93-3.95 (d, 9H), 4.04 (d, 3H), 7.49 (s, 1H), 7.78 (s, 1H), 7.89 (s, 2H); MS (ESI) m/z 401 ([M+H]+).

Example II

Synthesis of 1,2,3,4-tetrahydroisoquinoline derivatives

II-1. Synthesis of 5-hydroxy-6-methoxy-1,2,3,4-tetrahydroisoquinoline

5-Hydroxy-6-methoxy-1,2,3,4-tetrahydroisoquinoline was prepared from 2-(2-aminoethyl)-6-methoxyphenol hydrochloride as outlined in Scheme 12.

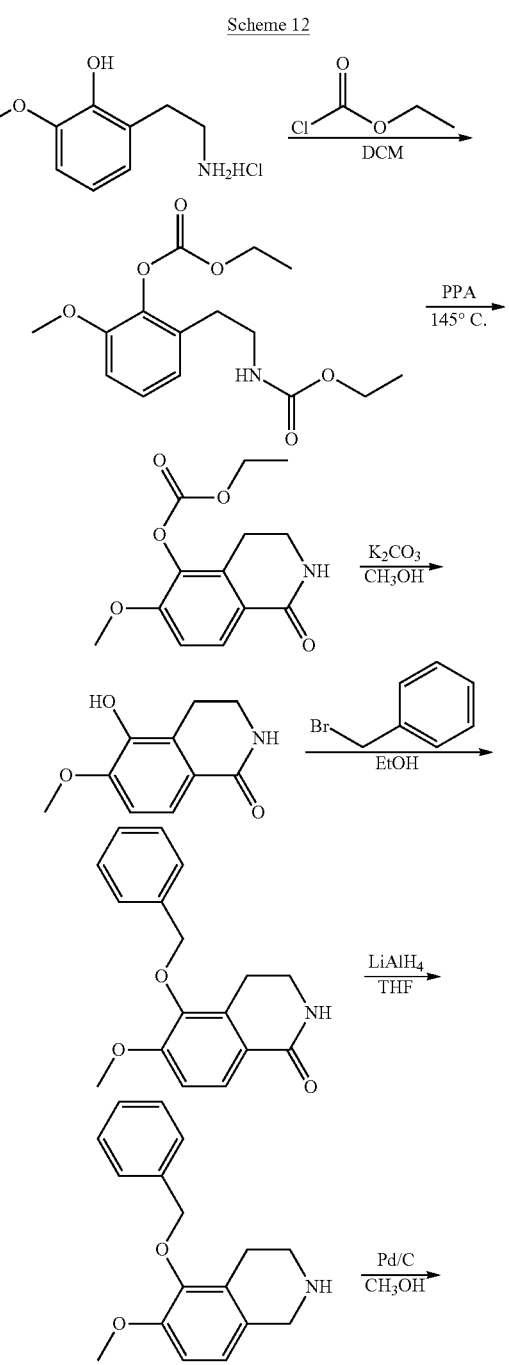

Scheme 12

-continued

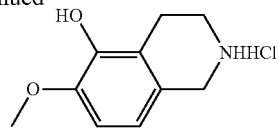

1. Synthesis of 2-[2-[(ethoxycarbonyl)amino]ethyl]-6-methoxyphenyl ethyl carbonate Into a 1000-mL 3-necked round-bottom flask purged and maintained with an inert atmosphere of nitrogen, was placed 2-(2-aminoethyl)-6-methoxyphenol hydrochloride (20 g, 98.20 mmol, 1.00 equiv), dichloromethane (500 g, 5.89 mol, 59.95 equiv) and triethylamine (49.5 g, 489.18 mmol, 5.00 equiv). This was followed by the addition of ethyl chloroformate (30 g, 276.44 mmol, 2.50 equiv) dropwise with stirring at 0° C. in 10 min. The resulting solution was stirred for 1 h at room temperature. The resulting mixture was washed with 3×300 mL of water. The mixture was dried over anhydrous sodium sulfate and concentrated under vacuum. The residue was applied onto a silica gel column with ethyl acetate/petroleum ether (1:3) to yield 20 g (65%) of 2-[2-[(ethoxycarbonyl)amino]ethyl]-6-methoxyphenyl ethyl carbonate as brown oil. MS (ESI) m/z 312 ([M+H]$^+$).

2. Synthesis of ethyl 6-methoxy-1-oxo-1,2,3,4-tetrahydroisoquinolin-5-yl carbonate Into a 500-mL 3-necked round-bottom flask purged and maintained with an inert atmosphere of nitrogen, was placed polyphosphoric acid (PPA, 150 g). This was followed by the addition of 2-[2-[(ethoxycarbonyl)amino]ethyl]-6-methoxyphenyl ethyl carbonate (20 g, 64.24 mmol, 1.00 equiv) at 145° C. The resulting solution was stirred for 20 min at 140-145° C. The reaction mixture was cooled to room temperature with a water/ice bath. The resulting solution was diluted with 500 mL of ethyl acetate and 500 mL of water. The resulting mixture was washed with 3×300 mL of water. The mixture was dried over anhydrous sodium sulfate and concentrated under vacuum. The residue was applied onto a silica gel column with ethyl acetate/petroleum ether (1:1). This resulted in 1.5 g (9%) of ethyl 6-methoxy-1-oxo-1,2,3,4-tetrahydroisoquinolin-5-yl carbonate as a gray solid. MS (ESI) m/z 266 ([M+H]$^+$).

3. Synthesis of 5-hydroxy-6-methoxy-1,2,3,4-tetrahydroisoquinolin-1-one

Into a 50-mL 3-necked round-bottom flask, was placed ethyl 6-methoxy-1-oxo-1,2,3,4-tetrahydroisoquinolin-5-yl carbonate (1.5 g, 5.65 mmol, 1.00 equiv), methanol (20 mL) and K$_2$CO$_3$ (2.34 g, 16.81 mmol, 3.00 equiv). The resulting solution was stirred for 3 h at room temperature. The solids were filtered out. The resulting mixture was concentrated under vacuum. The residue was applied onto a silica gel column with ethyl acetate (100%). This resulted in 0.7 g (64%) of 5-hydroxy-6-methoxy-1,2,3,4-tetrahydroisoquinolin-1-one as a off-white solid. $^1$H NMR (300 MHz, DMSO-d$_6$) δ: 2.83 (m, 2H), 3.78 (s, 3H), 4.14 (s, 2H), 6.63-6.66 (2s, 1H), 6.88-6.91 (2s, 1H); MS (ESI) m/z 194 ([M+H]$^+$).

4. Synthesis of 5-(benzyloxy)-6-methoxy-1,2,3,4-tetrahydroisoquinolin-1-one

Into a 50-mL 3-necked round-bottom flask purged and maintained with an inert atmosphere of nitrogen, was placed 5-hydroxy-6-methoxy-1,2,3,4-tetrahydroisoquinolin-1-one (700 mg, 3.62 mmol, 1.00 equiv), Cs$_2$CO$_3$ (2.36 g, 7.22 mmol, 2.00 equiv), ethanol (20 mL) and (bromomethyl)benzene (740 mg, 4.35 mmol, 1.20 equiv). The resulting solution was heated to reflux for 1 hr. The solids were filtered out. The resulting mixture was concentrated under vacuum. The residue was applied onto a silica gel column with ethyl acetate/petroleum ether (1:1). This resulted in 1 g (97%) of 5-(benzyloxy)-6-methoxy-1,2,3,4-tetrahydroisoquinolin-1-one as a gray solid. $^1$H NMR (300 MHz, DMSO-d$_6$) δ: 2.70-2.75 (t, 2H), 3.19-3.23 (t, 2H), 3.90 (s, 3H), 4.95 (s, 2H), 7.05-7.08 (m, 1H), 7.33-7.42 (m, 5H), 7.62-7.64 (m, 1H), 7.70 (S, 1H); MS (ESI) m/z 284 ([M+H]$^+$).

5. Synthesis of 5-(benzyloxy)-6-methoxy-1,2,3,4-tetrahydroisoquinoline

Into a 50-mL 3-necked round-bottom flask purged and maintained with an inert atmosphere of nitrogen, was placed 5-(benzyloxy)-6-methoxy-1,2,3,4-tetrahydroisoquinolin-1-one (1 g, 3.53 mmol, 1.00 equiv), oxolane (20 mL) and LiAlH$_4$ (400 mg, 11.79 mmol, 3.00 equiv). The resulting solution was heated to reflux for 2 hr. The reaction mixture was cooled to 0° C. with a water/ice bath. The reaction was then quenched by the addition of 0.4 mL of water. The solids were filtered out. The resulting mixture was concentrated under vacuum. This resulted in 0.8 g (crude) of 5-(benzyloxy)-6-methoxy-1,2,3,4-tetrahydroisoquinoline as light yellow oil. MS (ESI) m/z 270 ([M+H]$^+$).

6. Synthesis of 5-hydroxy-6-methoxy-1,2,3,4-tetrahydroisoquinoline

Into a 50-mL 3-necked round-bottom flask purged and maintained with an inert atmosphere of nitrogen, was placed Palladium carbon (10%) (200 mg), methanol (10 mL) and 5-(benzyloxy)-6-methoxy-1,2,3,4-tetrahydroisoquinoline (800 mg, 2.97 mmol, 1.00 equiv). To the above H$_2$ (enough, amount) was introduced in. The resulting solution was stirred for 2 h at room temperature. The solids were filtered out. The resulting solution was diluted with 12 mL of tetrahydrofuran. To this was HCl (gas) (enough amount) was introduced in. The resulting mixture was concentrated under vacuum. The solids were collected by filtration. The filter cake was washed with 2×20 mL of dichloromethane. This resulted in 0.5 g (crude) of 5-hydroxy-6-methoxy-1,2,3,4-tetrahydroisoquinoline hydrochloride as a off-white solid. $^1$H NMR (300 MHz, DMSO-d$_6$) δ 2.88-3.92 (t, 2H), 3.40-3.44 (t, 2H), 3.77 (s, 3H), 4.20 (s, 2H), 6.68-6.70 (d, 1H), 6.88-6.91 (d, 1H); MS (ESI) m/z 180 ([M+H]$^+$).

II-2. Synthesis of 5,6-dihydroxy-1,2,3,4-tetrahydroisoquinoline

Into a 100-mL 3-necked round-bottom flask purged and maintained with an inert atmosphere of nitrogen, was placed tert-butyl 5-hydroxy-6-methoxy-1,2,3,4-tetrahydroisoquinoline-2-carboxylate (70 mg, 0.25 mmol, 1.00 equiv) and dichloromethane (30 mL). This was followed by the addition of BBr$_3$ (187 mg) dropwise with stirring at 0° C. The resulting solution was stirred for 1 h at 0° C. in a water/ice bath. The resulting mixture was concentrated under vacuum. This resulted in 100 mg (crude) of 5,6-dihydroxy-1,2,3,4-tetrahydroisoquinoline hydrobromide as a light yellow solid. MS (ESI) m/z 166 ([M+H-HBr]$^+$).

II-3. Synthesis of 5,6-dimethoxy-1,2,3,4-tetrahydroisoquinoline 5,6-Dimethoxy-1,2,3,4-tetrahydroisoquinoline was prepared from 5-(benzyloxy)-6-methoxy-1,2,3,4-tetrahydroisoquinoline as outlined in Scheme 13.

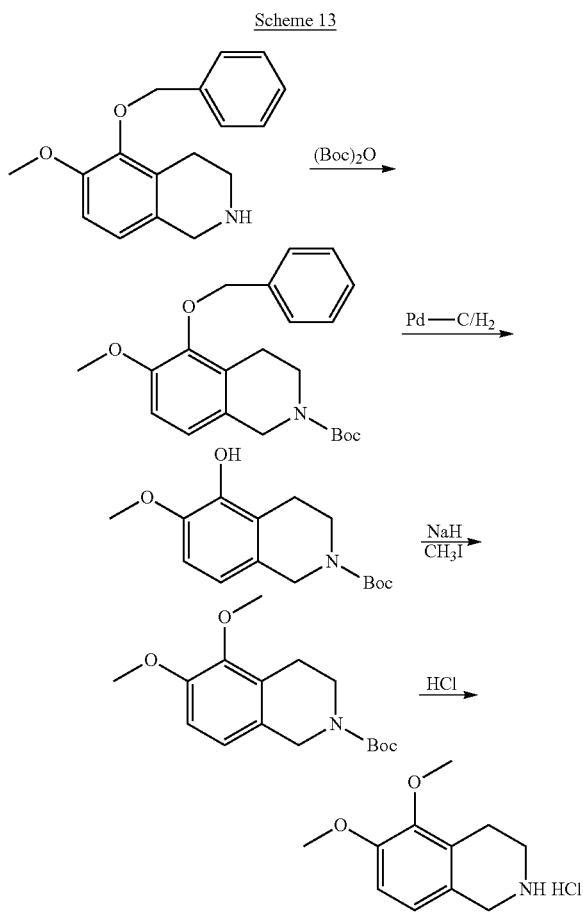

Scheme 13

1. Synthesis of tert-butyl 5-(benzyloxy)-6-methoxy-3,4-dihydroisoquinoline-2(1H)-carboxylate Into a 50-mL 3-necked round-bottom flask purged and maintained with an inert atmosphere of nitrogen, was placed a solution of 5-(benzyloxy)-6-methoxy-1,2,3,4-tetrahydroisoquinoline (3.8 g, 14.11 mmol, 1.00 equiv) in dichloromethane (30 mL) and TEA (6.38 g, 55.96 mmol, 4.00 equiv). This was followed by the addition of (Boc)$_2$O (6.10 g, 27.95 mmol, 2.00 equiv) at 0° C. The resulting solution was stirred overnight at room temperature. The resulting mixture was concentrated under vacuum. The resulting solution was diluted with 30 mL of ethyl acetate. The resulting mixture was washed with 3×30 mL of water. The mixture was dried over anhydrous sodium sulfate and concentrated under vacuum. This resulted in 4.5 g (86%) of tert-butyl 5-(benzyloxy)-6-methoxy-1,2,3,4-tetrahydroisoquinoline-2-carboxylate as light brown oil. MS (ESI) m/z 270 ([M+H-t-Boc]$^+$); R$_f$ 0.11 (starting material) and 0.52 (product) in ethyl acetate:petroleum ether=1:1.

2. Synthesis of tert-butyl 5-hydroxy-6-methoxy-3,4-dihydroisoquinoline-2(1H)-carboxylate Into a 50-mL 3-necked round-bottom flask, was placed a solution of tert-butyl 5-(benzyloxy)-6-methoxy-1,2,3,4-tetrahydroisoquinoline-2-carboxylate (5.5 g, 14.89 mmol, 1.00 equiv) in MeOH (20 mL) and Pd/C (0.55 g). To the above H$_2$ (enough, gas) was introduced in. The resulting solution was stirred overnight at room temperature. The solids were filtered out. The resulting mixture was concentrated under vacuum. This resulted in 3.6 g (87%) of tert-butyl 5-hydroxy-6-methoxy-1,2,3,4-tetrahydroisoquinoline-2-carboxylate as a light yellow solid. MS (ESI) m/z 224 ([M+H-t-butyl]$^+$); R$_f$ 0.15 (starting material) and 0.32 (product) in ethyl acetate:petroleum ether=1:5.

3. Synthesis of tert-butyl 5,6-dimethoxy-3,4-dihydroisoquinoline-2(1H)-carboxylate Into a 50-mL 3-necked round-bottom flask purged and maintained with an inert atmosphere of nitrogen, was placed a solution of tert-butyl 5-hydroxy-6-methoxy-1,2,3,4-tetrahydroisoquinoline-2-carboxylate (100 mg, 0.36 mmol, 1.00 equiv) in N,N-dimethylformamide (10 mL) and sodium hydride (12.9 mg, 1.50 equiv). This was followed by the addition of CH$_3$I (254.2 mg, 5.00 equiv). The resulting solution was stirred overnight at room temperature. The resulting solution was diluted with 100 mL of water. The resulting solution was extracted with 3×30 mL of ethyl acetate and the organic layers combined and dried over anhydrous sodium sulfate and concentrated under vacuum. This resulted in 85 mg (81%) of tert-butyl 5,6-dimethoxy-1,2,3,4-tetrahydroisoquinoline-2-carboxylate as a light yellow solid. MS (ESI) m/z 194 ([M+H-t-Boc]$^+$); R$_f$ 0.28 (starting material) and 0.43 (product) in ethyl acetate:petroleum ether=1:3.

4. Synthesis of 5,6-dimethoxy-1,2,3,4-tetrahydroisoquinoline hydrochloride

Into a 50-mL round-bottom flask, was placed a solution of tert-butyl 5,6-dimethoxy-1,2,3,4-tetrahydroisoquinoline-2-carboxylate (800 mg, 2.73 mmol, 1.00 equiv) in methanol (15 mL) and hydrogen chloride (4 mL). The resulting solution was stirred for 5 h at room temperature. The resulting mixture was concentrated under vacuum. The residue was diluted with 5 mL of water. The resulting mixture was extracted with 3×30 mL of ethyl acetate and the aqueous layer combined. The mixture was concentrated under vacuum. This resulted in 500 mg (80%) of 5,6-dimethoxy-1,2,3,4-tetrahydroisoquinoline hydrochloride as a white solid. MS (ESI) m/z 194 ([M+H]$^+$).

II-4. Synthesis of 5-hydroxy-6-dimethylamino-1,2,3,4-tetrahydroisoquinoline

5-Hydroxy-6-dimethylamino-1,2,3,4-tetrahydroisoquinoline was prepared from methyl 2-fluoro-3-nitrobenzoate as outlined in Scheme 14.

Scheme 14

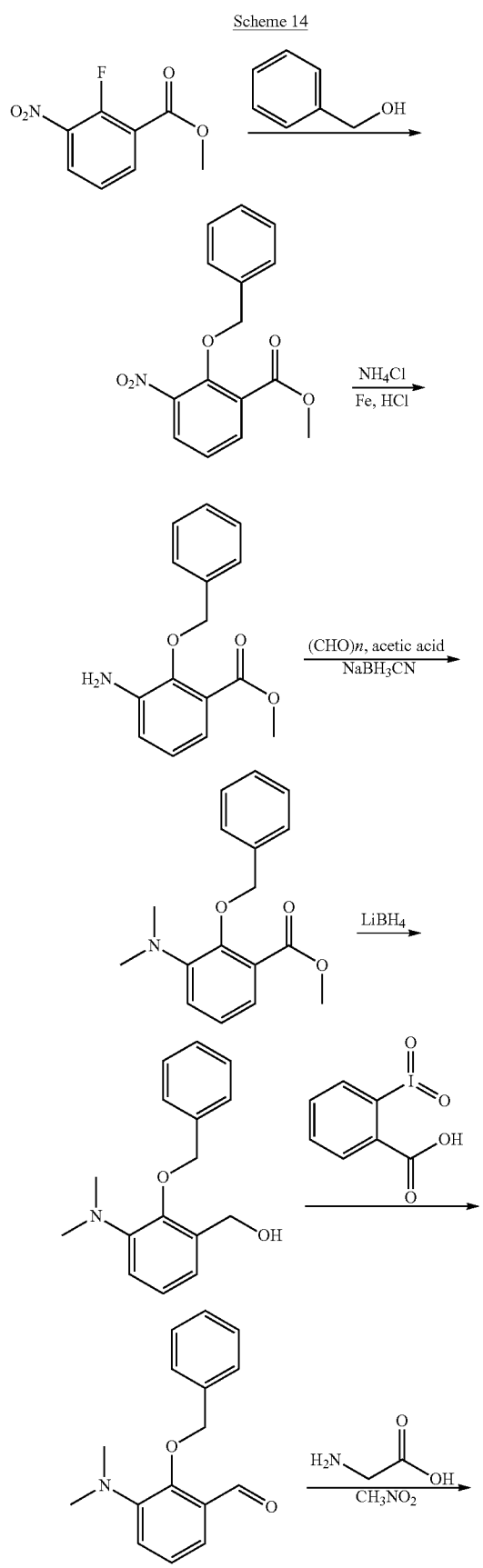

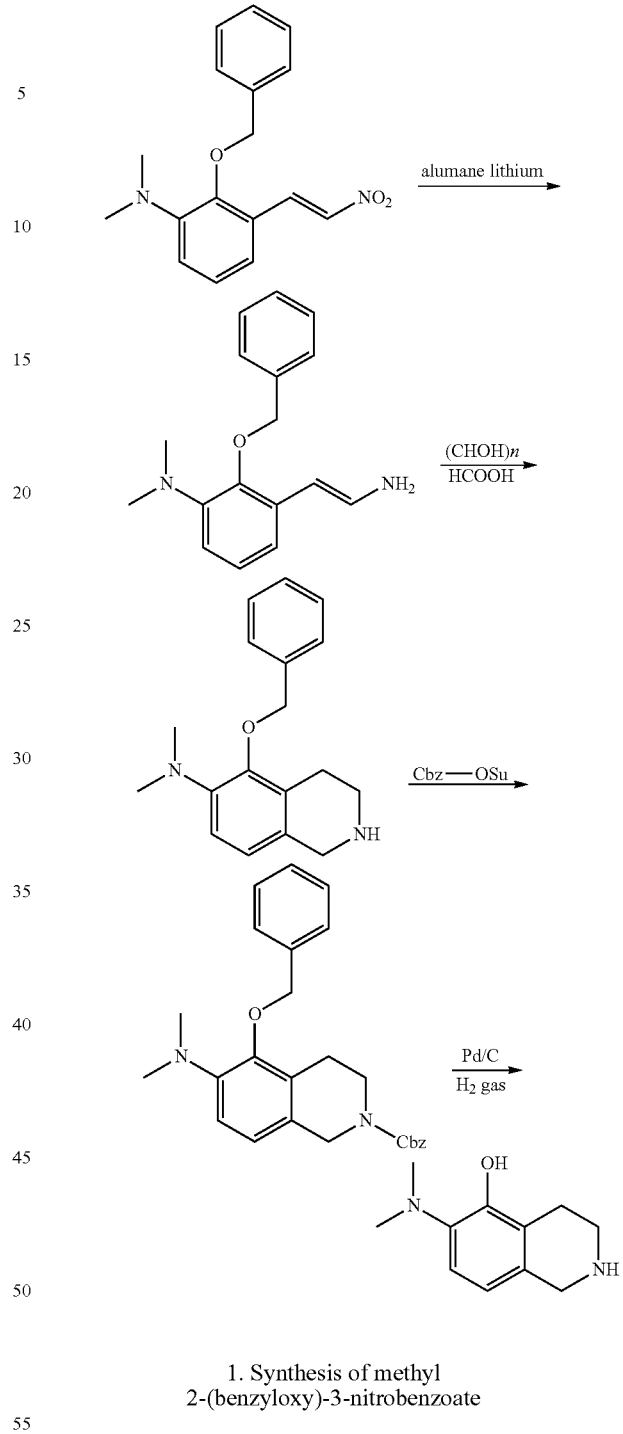

1. Synthesis of methyl 2-(benzyloxy)-3-nitrobenzoate

Into a 500-mL 4-necked round-bottom flask purged and maintained with an inert atmosphere of nitrogen, was placed a solution of phenylmethanol (10.7 g, 98.95 mmol, 1.05 equiv) in N,N-dimethylformamide (100 mL). This was followed by the addition of sodium hydride (3.9 g, 162.50 mmol, 1.20 equiv, 70%) in several batches at 0° C. The mixture was stirred for 25 min at 0° C. To this was added a solution of methyl 2-fluoro-3-nitrobenzoate (18.8 g, 94.41 mmol, 1.00 equiv) in N,N-dimethylformamide (150 mL) dropwise with stirring at 0° C. The resulting solution was stirred overnight at room temperature. The mixture was diluted with 700 mL of ethyl acetate. The resulting mixture was washed with 3×800 mL of water. The mixture was dried over anhydrous sodium sulfate and concentrated under vacuum. The residue was applied onto a silica gel column with ethyl acetate/petroleum ether (1:40). This resulted in 20 g (74%) of methyl 2-(benzyloxy)-3-nitrobenzoate as yellow oil. MS (ESI) m/z 288 ([M+H]$^+$).

2. Synthesis of methyl 3-amino-2-(benzyloxy)benzoate

Into a 500-mL 4-necked round-bottom flask, was placed methyl 2-(benzyloxy)-3-nitrobenzoate (20 g, 69.62 mmol, 1.00 equiv), ethanol (200 mL), water (100 mL) and NH$_4$Cl (11.1 g, 207.52 mmol, 2.98 equiv). This was followed by the addition of Fe (19.5 g) in portions. To the mixture was added hydrogen chloride (5 mL). The resulting solution was stirred for 5 h at 85° C. in an oil bath. The solids were filtered out. The filter cake was washed with 3×50 mL of ethanol. The resulting mixture was concentrated under vacuum. The residue was dissolved in 1000 mL of ethyl acetate. The resulting mixture was washed with 3×800 mL of water. The resulting mixture was dried over anhydrous sodium sulfate and concentrated under vacuum. This resulted in 17 g (95%) of methyl 3-amino-2-(benzyloxy)benzoate as yellow oil. MS (ESI) m/z 258 ([M+H]$^+$).

3. Synthesis of methyl 2-(benzyloxy)-3-(dimethylamino)benzoate

Into a 2000-mL 3-necked round-bottom flask purged and maintained with an inert atmosphere of nitrogen, was placed methyl 3-amino-2-(benzyloxy)benzoate (17 g, 66.07 mmol, 1.00 equiv), acetic acid (360 mL) and (CHO)n (11.91 g, 6.00 equiv). This was followed by the addition of NaBH$_3$CN (25 g, 6.00 equiv) in several batches at 0° C. The resulting solution was stirred overnight at 25° C. The pH value of the solution was adjusted to 7 with sodium hydroxide (cooled) (1 mol/L). The resulting solution was extracted with 3×100 mL of ethyl acetate and the organic layers combined. The mixture was dried over anhydrous sodium sulfate and concentrated under vacuum. The residue was applied onto a silica gel column with ethyl acetate/petroleum ether (1:15). This resulted in 16 g (85%) of methyl 2-(benzyloxy)-3-(dimethylamino)benzoate as yellow oil. MS (ESI) m/z 286 ([M+H]$^+$).

4. Synthesis of (2-(benzyloxy)-3-(dimethylamino)phenyl)methanol

Into a 500-mL 3-necked round-bottom flask purged and maintained with an inert atmosphere of nitrogen, was placed methyl 2-(benzyloxy)-3-(dimethylamino)benzoate (9.1 g, 31.89 mmol, 1.00 equiv) and oxolane (180 mL). This was followed by the addition of LiBH$_4$ (3.31 g, 152.10 mmol, 4.77 equiv) in several batches. The resulting solution was stirred for 8 h at 57° C. in an oil bath. The reaction was poured into 400 mL of water/ice. The resulting solution was extracted with 2×500 mL of ethyl acetate and the organic layers combined. The mixture was dried over anhydrous sodium sulfate and concentrated under vacuum. The residue was applied onto a silica gel column with ethyl acetate/petroleum ether (1:20). This resulted in 4.5 g (55%) of [2-(benzyloxy)-3-(dimethylamino)phenyl]methanol as yellow oil. MS (ESI) m/z 258 ([M+H]$^+$).

5. Synthesis of 2-(benzyloxy)-3-(dimethylamino)benzaldehyde

Into a 250-mL 3-necked round-bottom flask purged and maintained with an inert atmosphere of nitrogen, was placed [2-(benzyloxy)-3-(dimethylamino)phenyl]methanol (3.6 g, 13.99 mmol, 1.00 equiv) and DMSO (50 mL). This was followed by the addition of 2-iodoxybenzoic acid (4.31 g, 15.39 mmol, 1.10 equiv) in several batches. The resulting solution was stirred for 2 h at 25° C. The resulting solution was diluted with 200 mL of ethyl acetate. The resulting mixture was washed with 4×50 mL of water. The solids were filtered out. The mixture was dried over anhydrous sodium sulfate and concentrated under vacuum. This resulted in 3.4 g (95%) of 2-(benzyloxy)-3-(dimethylamino)benzaldehyde as yellow oil. MS (ESI) m/z 256 ([M+H]$^+$).

6. Synthesis of 2-(benzyloxy)-N,N-dimethyl-3-[(Z)-2-nitroethenyl]aniline

Into a 100-mL 3-necked round-bottom flask purged and maintained with an inert atmosphere of nitrogen, was placed 2-(benzyloxy)-3-(dimethylamino)benzaldehyde (5 g, 19.58 mmol, 1.00 equiv), acetic acid (40 mL), acetic acid amine (750 mg, 9.73 mmol, 0.50 equiv) and nitromethane (11.96 g, 195.94 mmol, 10.01 equiv). The resulting solution was stirred overnight at 105° C. in an oil bath. The resulting solution was diluted with 200 mL of ethyl acetate. The mixture was washed with NaOH (5 mol/L) until pH=7. The mixture was dried over anhydrous sodium sulfate and concentrated under vacuum. The residue was applied onto a silica gel column with ethyl acetate/petroleum ether (1:20). This resulted in 3.5 g (60%) of 2-(benzyloxy)-N,N-dimethyl-3-[(Z)-2-nitroethenyl]aniline as a dark red solid. MS (ESI) m/z 299 ([M+H]$^+$).

7. Synthesis of 3-(2-aminoethyl)-2-(benzyloxy)-N,N-dimethylaniline

Into a 1000-mL 3-necked round-bottom flask purged and maintained with an inert atmosphere of nitrogen, was placed oxolane (150 mL). This was followed by the addition of alumane lithium (5.6 g, 165.08 mmol, 3.35 equiv) in several batches at 0° C. To the mixture was added a solution of 2-(benzyloxy)-N,N-dimethyl-3-[(Z)-2-nitroethenyl]aniline (14.7 g, 49.27 mmol, 1.00 equiv) in tetrahtdrofuran (150 mL) dropwise with stirring at 0-10° C. The resulting solution was stirred overnight at 25° C. The mixture was cooled to 0-5° C. The reaction was then quenched by the addition of 6 mL of water, 18 mL of NaOH (10%) and 6 mL of water. The resulting solution was extracted with 2×500 mL of ethyl acetate and the organic layers combined. The mixture was dried over anhydrous sodium sulfate and concentrated under vacuum. The residue was applied onto a silica gel column with dichloromethane/methanol (1:50-1:20). This resulted in 6.4 g (48%) of 3-(2-aminoethyl)-2-(benzyloxy)-N,N-dimethylaniline as light yellow oil. MS (ESI) m/z 271 ([M+H]$^+$).

8. Synthesis of 5-(benzyloxy)-N,N-dimethyl-1,2,3,4-tetrahydroisoquinolin-6-amine Into a 100-mL round-bottom flask purged and maintained with an inert atmosphere of nitrogen, was placed 3-(2-aminoethyl)-2-(benzyloxy)-N,N-dimethylaniline (1 g, 3.70 mmol, 1.00 equiv), formic acid (10 mL) and (CHOH)n (89 mg). The resulting solution was stirred overnight at 55° C. in an oil bath. The resulting mixture was concentrated under vacuum. The resulting solution was diluted with 10 mL of water. The pH value of the solution was adjusted to 10 with sodium hydroxide (10 mol/L). The resulting solution was extracted with 1×50 mL of ethyl acetate and the organic layers combined. The resulting mixture was washed with 2×20 mL of water. The mixture was dried over anhydrous sodium sulfate and concentrated under vacuum. This resulted in 1 g (96%) of 5-(benzyloxy)-N,N-dimethyl-1,2,3,4-tetrahydroisoquinolin-6-amine as brown oil. MS (ESI) m/z 283 ([M+H]$^+$).

9. Synthesis of benzyl 5-(benzyloxy)-6-(dimethylamino)-1,2,3,4-tetrahydroisoquinoline-2-carboxylate Into a 100-mL 3-necked round-bottom flask purged and maintained with an inert atmosphere of nitrogen, was placed N,N-dimethyl-5-phenoxy-1,2,3,4-tetrahydroisoquinolin-6-amine (1 g, 3.73 mmol, 1.00 equiv), tetrahydrofuran (30 mL) and benzyloxycarbonyl N-succinimide (0.893 g). The resulting solution was stirred overnight at 25° C. The resulting solution was diluted with 100 mL of ethyl acetate. The resulting mixture was washed with 2×50 mL of water. The mixture was dried over anhydrous sodium sulfate and concentrated under vacuum. The crude product was purified by Flash-Prep-HPLC. This resulted in 1 g (64%) of benzyl 5-(benzyloxy)-6-(dimethylamino)-1,2,3,4-tetrahydroisoquinoline-2-carboxylate as yellow oil. MS (ESI) m/z 417 ([M+H]$^+$).

10. Synthesis of 5-hydroxy-6-dimethylamino-1,2,3,4-tetrahydroisoquinoline

Into a 100-mL 3-necked round-bottom flask purged and maintained with an inert atmosphere of nitrogen, was placed methanol (40 mL), Palladium carbon (400 mg) and benzyl 5-(benzyloxy)-6-(dimethylamino)-1,2,3,4-tetrahydroisoquinoline-2-carboxylate (1.6 g, 3.84 mmol, 1.00 equiv). To the above H$_2$ gas was introduced in. The resulting solution was stirred overnight at 25° C. The solids were filtered out. The resulting mixture was concentrated under vacuum. This resulted in 1 g (crude) of 5-hydroxy-6-dimethylamino-1,2,3,4-tetrahydroisoquinoline as brown oil. MS (ESI) m/z 193 ([M+H]$^+$).

II-5. Synthesis of 5-hydroxy-6-methyl-1,2,3,4-tetrahydroisoquinoline

5-Hydroxy-6-methyl-1,2,3,4-tetrahydroisoquinoline was prepared from 2-hydroxy-3-methylbenzoic acid as outlined in Scheme 15.

Scheme 15

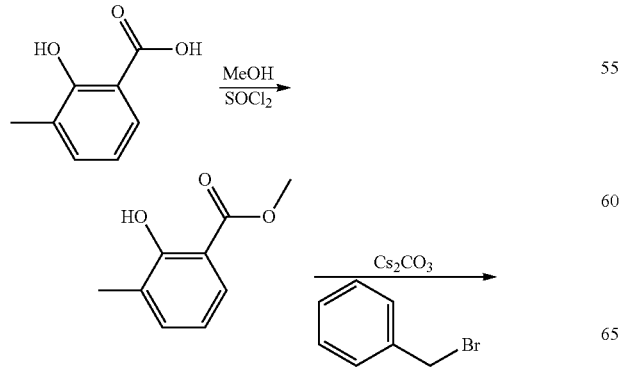

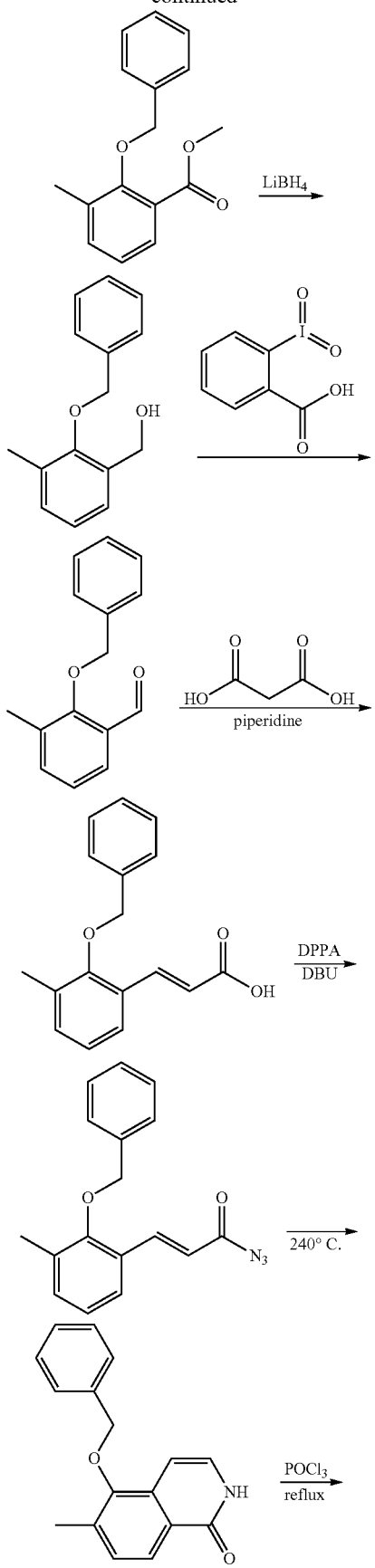

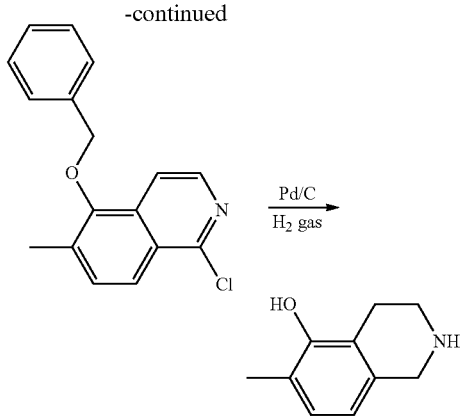

1. Synthesis of methyl 2-hydroxy-3-methylbenzoate

Into a 3-L 4-necked round-bottom flask purged and maintained with an inert atmosphere of nitrogen, was placed 2-hydroxy-3-methylbenzoic acid (50 g, 328.63 mmol, 1.00 equiv) and methanol (800 mL). This was followed by the addition of thionyl chloride (20 mL) dropwise with stirring. The resulting solution was stirred overnight at 80° C. The resulting mixture was concentrated under vacuum. The residue was diluted with 1000 mL of ethyl acetate. The resulting mixture was washed with 2×800 mL of NaOH (cold). The resulting mixture was washed with 2×500 mL of water. The mixture was dried over anhydrous sodium sulfate and concentrated under vacuum. This resulted in 25 g (46%) of methyl 2-hydroxy-3-methylbenzoate as brown oil. $^1$H NMR (300 MHz, DMSO-$d_6$) δ 2.19 (s, 3H), 3.90 (s, 3H), 6.83-6.88 (m, 1H), 7.41-7.44 (m, 1H), 7.64-7.66 (m, 1H), 10.87 (b, 1H).

2. Synthesis of methyl 2-(benzyloxy)-3-methylbenzoate

Into a 500-mL 3-necked round-bottom flask purged and maintained with an inert atmosphere of nitrogen, was placed methyl 2-hydroxy-3-methylbenzoate (25 g, 150.44 mmol, 1.00 equiv), N,N-dimethylformamide (250 mL) and Cs$_2$CO$_3$ (103 g, 316.13 mmol, 2.10 equiv). This was followed by the addition of (bromomethyl)benzene (31 g, 181.25 mmol, 1.20 equiv). The resulting solution was stirred for 2 h at room temperature. The resulting solution was diluted with 1.2 L of ethyl acetate. The resulting mixture was washed with 3×800 mL of water. The mixture was dried over anhydrous sodium sulfate and concentrated under vacuum. This resulted in 40 g (crude) of methyl 2-(benzyloxy)-3-methylbenzoate as brown oil. MS (ESI) m/z 257 ([M+H]$^+$).

3. Synthesis of (2-(benzyloxy)-3-methylphenyl)methanol

Into a 500-mL 3-necked round-bottom flask purged and maintained with an inert atmosphere of nitrogen, was placed methyl 2-(benzyloxy)-3-methylbenzoate (40 g, 156.07 mmol, 1.00 equiv) and tetrahydrofuran (300 mL). This was followed by the addition of LiBH$_4$ (15.6 g, 5.00 equiv) in several batches with stirring. The resulting solution was stirred overnight at 60° C. The reaction was then quenched by the addition of 1.5 L of water/ice. The resulting solution was extracted with 2×800 mL of ethyl acetate and the organic layers combined. The resulting mixture was washed with 2×1000 mL of H$_2$O. The mixture was dried over anhydrous sodium sulfate and concentrated under vacuum. This resulted in 30 g (84%) of [2-(benzyloxy)-3-methylphenyl]methanol as light brown oil. $^1$H NMR (300 MHz, DMSO-$d_6$) δ 2.21 (s, 3H), 4.55-4.57 (m, 2H), 4.83 (s, 2H), 5.05-5.09 (m, 1H), 7.02-7.51 (m, 8H).

4. Synthesis of 2-(benzyloxy)-3-methylbenzaldehyde

Into a 500-mL 3-necked round-bottom flask purged and maintained with an inert atmosphere of nitrogen, was placed [2-(benzyloxy)-3-methylphenyl]methanol (30 g, 131.41 mmol, 1.00 equiv) and DMSO (300 mL). This was followed by the addition of 2-iodoxybenzoic acid (41 g, 146.42 mmol, 1.10 equiv) in several batches. The resulting solution was stirred for 2 h at room temperature. The resulting solution was diluted with 1.5 L of ethyl acetate. The resulting mixture was washed with 3×800 mL of brine. The mixture was dried over anhydrous sodium sulfate. This resulted in 30 g (crude) of 2-(benzyloxy)-3-methylbenzaldehyde as orange oil. MS (ESI) m/z 227 ([M+H]).

5. Synthesis of (2Z)-3-[2-(benzyloxy)-3-methylphenyl]prop-2-enoic acid

Into a 500-mL 3-necked round-bottom flask purged and maintained with an inert atmosphere of nitrogen, was placed 2-(benzyloxy)-3-methylbenzaldehyde (20 g, 88.39 mmol, 1.00 equiv), propanedioic acid (27.6 g, 265.23 mmol, 3.00 equiv), piperidine (1.5 g, 17.62 mmol, 0.20 equiv) and pyridine (200 mL). The resulting solution was heated to reflux for 2 h in an oil bath. The reaction was then quenched by the addition of 1.5 L of water/ice. The pH value of the solution was adjusted to 2-3 with hydrogen chloride. The solids were collected by filtration. The filter cake was washed with 2×500 mL of water and 2×500 mL of hexane. This resulted in 21 g (89%) of (2Z)-3-[2-(benzyloxy)-3-methylphenyl]prop-2-enoic acid as a white solid. MS (ESI) m/z 269 ([M+H]$^+$).

6. Synthesis of (2Z)-3-[2-(benzyloxy)-3-methylphenyl]prop-2-enoyl azide

Into a 500-mL 3-necked round-bottom flask purged and maintained with an inert atmosphere of nitrogen, was placed (2Z)-3-[2-(benzyloxy)-3-methylphenyl]prop-2-enoic acid (20 g, 74.54 mmol, 1.00 equiv), toluene (300 mL) and diphenylphosphoryl azide (25 g, 90.84 mmol, 1.20 equiv). This was followed by the addition of DBU (14 g, 91.96 mmol, 1.20 equiv) dropwise with stirring at 0-10° C. The resulting solution was stirred for 1 h at 0-10° C. in a water/ice bath. The resulting solution was diluted with 1 L of ethyl acetate. The resulting mixture was washed with 2×800 mL of water. The mixture was dried over anhydrous sodium sulfate and concentrated under vacuum. The residue was applied onto a silica gel column with ethyl acetate/petroleum ether (1:40). This resulted in 13 g (59%) of (2Z)-3-[2-(benzyloxy)-3-methylphenyl]prop-2-enoyl azide as a white solid. R$_f$: 0.44 (in ethyl acetate:petroleum ether=1:5).

7. Synthesis of 5-(benzyloxy)-6-methyl-1,2-dihydroisoquinolin-1-one

Into a 250-mL 3-necked round-bottom flask purged and maintained with an inert atmosphere of nitrogen, was placed phenoxybenzene (80 mL), tributylamine (10 mL). This was followed by the addition of (2Z)-3-[2-(benzyloxy)-3-methylphenyl]prop-2-enoyl azide (2.5 g, 8.52 mmol, 1.00 equiv), in portions at 240° C. The resulting solution was stirred for 20 min at 240° C. The mixture was cooled to room temperature. The residue was applied onto a silica gel column with ethyl acetate/petroleum ether (1:30-1:1)). This resulted in 600 mg (27%) of 5-(benzyloxy)-6-methyl-1,2-dihydroisoquinolin-1-one as a white solid. $^1$H NMR (300 MHz, DMSO-$d_6$) δ 2.37 (s, 3H), 4.91 (s, 2H), 6.60-7.91 (m, 9H), 11.21 (b, 1H).

8. Synthesis of 5-(benzyloxy)-1-chloro-6-methylisoquinoline

Into a 50-mL 3-necked round-bottom flask purged and maintained with an inert atmosphere of nitrogen, was placed 5-(benzyloxy)-6-methyl-1,2-dihydroisoquinolin-1-one (100 mg, 0.38 mmol, 1.00 equiv) and $POCl_3$ (10 mL). The resulting solution was heated to reflux for 3 h in an oil bath. The resulting mixture was concentrated under vacuum. The resulting solution was diluted with 250 mL of ethyl acetate. The resulting mixture was washed with 2×150 mL of water and 2×150 mL of brine. The mixture was dried over anhydrous sodium sulfate and concentrated under vacuum. The residue was applied onto a silica gel column with ethyl acetate/petroleum ether (1:20). This resulted in 70 mg (96%) of 5-(benzyloxy)-1-chloro-6-methylisoquinoline as an off-white solid. MS (ESI) m/z 284 ([M+H]$^+$).

9. Synthesis of 5-hydroxy-6-methyl-1,2,3,4-tetrahydroisoquinoline

Into a 50-mL 3-necked round-bottom flask purged and maintained with an inert atmosphere of nitrogen, was placed ethanol (20 mL). To the above hydrogen chloride (enough, gas) was introduced in. This was followed by the addition of 1-chloro-6-methylisoquinolin-5-ol (70 mg, 0.36 mmol, 1.00 equiv), Pd/C (30 mg). To the above hydrogen (enough, gas) was introduced in. The resulting solution was stirred overnight at room temperature with an inert atmosphere of $H_2$ (gas). The resulting mixture was concentrated under vacuum. The resulting mixture was washed with 1×10 mL of ether. This resulted in 50 mg (69%) of 5-hydroxy-6-methyl-1,2,3,4-tetrahydroisoquinoline hydrochloride as an off-white solid. $^1$H NMR (300 MHz, $D_2O$) δ 2.72 and 2.16 (s, 3H), 2.93 (t, 2H), 3.45 (t, 2H), 4.25 (s, 2H), 6.69 (d, 1H), 7.06 (d, 1H); MS (ESI) m/z 164 ([M+H]$^+$).

Example III

Synthesis of tetrahydroisoquinolin-2-yl-(quinazolin-4-yl)methanone compounds

Compounds 1 to 120 in Table 1 were synthesized as illustrated in Scheme 16, and characterized, except that compounds 2, 13, 18, 28, 33, 38, 43, 53, 58, 66, 71, 75, 80 and 85 were synthesized by the method used for the preparation of compound 2 (described below).

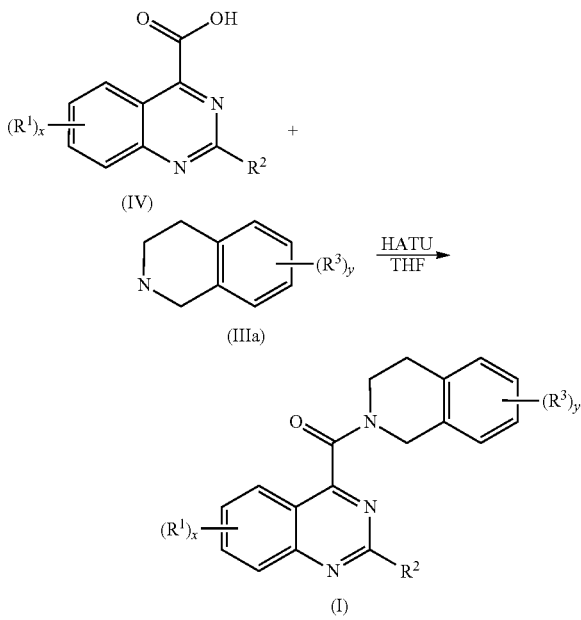

Scheme 16

Table 1

| Compound # | $R^1$ | $R^2$ | $R^3$ |
|---|---|---|---|
| 1 | H | 4-fluorophenyl | 5-OH-6-OMe |
| 2 | H | 4-fluorophenyl | 5,6-diOH |
| 3 | H | 4-fluorophenyl | 5,6-diOMe |
| 4 | H | 4-fluorophenyl | 5-OH-6-N(Me)$_2$ |
| 5 | H | 4-fluorophenyl | 5-OH-6-Me |
| 6 | H | 4-fluorophenyl | 5-OMe |
| 7 | H | 4-fluorophenyl | 6-OMe |
| 8 | H | 4-fluorophenyl | 5,7-diOMe |
| 9 | H | 4-fluorophenyl | 5-OH |
| 10 | H | 4-fluorophenyl | 5-F |
| 11 | H | 4-fluorophenyl | 6-F |
| 12 | H | 4-methylphenyl | 5-OH-6-OMe |
| 13 | H | 4-methylphenyl | 5,6-diOH |
| 14 | H | 4-methylphenyl | 5,6-diOMe |
| 15 | H | 4-methylphenyl | 5-OH-6-N(Me)$_2$ |
| 16 | H | 4-methylphenyl | 5-OH-6-Me |
| 17 | H | phenyl | 5-OH-6-OMe |
| 18 | H | phenyl | 5,6-diOH |
| 19 | H | phenyl | 5,6-diOMe |
| 20 | H | phenyl | 5-OH-6-N(Me)$_2$ |
| 21 | H | phenyl | 5-OH-6-Me |
| 22 | H | 4-methoxyphenyl | 5-OH-6-OMe |
| 23 | H | 4-methoxyphenyl | 5,6-diOH |
| 24 | H | 4-methoxyphenyl | 5,6-diOMe |
| 25 | H | 4-methoxyphenyl | 5-OH-6-N(Me)$_2$ |
| 26 | H | 4-methoxyphenyl | 5-OH-6-Me |
| 27 | H | 4-chlorophenyl | 5-OH-6-OMe |
| 28 | H | 4-chlorophenyl | 5,6-diOH |
| 29 | H | 4-chlorophenyl | 5,6-diOMe |
| 30 | H | 4-chlorophenyl | 5-OH-6-N(Me)$_2$ |
| 31 | H | 4-chlorophenyl | 5-OH-6-Me |
| 32 | H | 4-(dimethylamino)phenyl | 5-OH-6-OMe |
| 33 | H | 4-(dimethylamino)phenyl | 5,6-diOH |
| 34 | H | 4-(dimethylamino)phenyl | 5,6-diOMe |
| 35 | H | 4-(dimethylamino)phenyl | 5-OH-6-N(Me)$_2$ |
| 36 | H | 4-(dimethylamino)phenyl | 5-OH-6-Me |
| 37 | H | 4-(trifluoromethyl)phenyl | 5-OH-6-OMe |
| 38 | H | 4-(trifluoromethyl)phenyl | 5,6-diOH |
| 39 | H | 4-(trifluoromethyl)phenyl | 5,6-diOMe |
| 40 | H | 4-(trifluoromethyl)phenyl | 5-OH-6-N(Me)$_2$ |
| 41 | H | 4-(trifluoromethyl)phenyl | 5-OH-6-Me |
| 42 | H | 3-fluorophenyl | 5-OH-6-OMe |
| 43 | H | 3-fluorophenyl | 5,6-diOH |

Table 1-continued

| Compound # | R¹ | R² | R³ |
|---|---|---|---|
| 44 | H | 3-fluorophenyl | 5,6-diOMe |
| 45 | H | 3-fluorophenyl | 5-OH-6-N(Me)₂ |
| 46 | H | 3-fluorophenyl | 5-OH-6-Me |
| 47 | H | 3-methoxyphenyl | 5-OH-6-OMe |
| 48 | H | 3-methoxyphenyl | 5,6-diOH |
| 49 | H | 3-methoxyphenyl | 5,6-diOMe |
| 50 | H | 3-methoxyphenyl | 5-OH-6-N(Me)₂ |
| 51 | H | 3-methoxyphenyl | 5-OH-6-Me |
| 52 | H | 3-(trifluoromethyl)phenyl | 5-OH-6-OMe |
| 53 | H | 3-(trifluoromethyl)phenyl | 5,6-diOH |
| 54 | H | 3-(trifluoromethyl)phenyl | 5,6-diOMe |
| 55 | H | 3-(trifluoromethyl)phenyl | 5-OH-6-N(Me)₂ |
| 56 | H | 3-(trifluoromethyl)phenyl | 5-OH-6-Me |
| 57 | H | 2,4-difluorophenyl | 5-OH-6-OMe |
| 58 | H | 2,4-difluorophenyl | 5,6-diOH |
| 59 | H | 2,4-difluorophenyl | 5,6-diOMe |
| 60 | H | 2,4-difluorophenyl | 5-OH-6-N(Me)₂ |
| 61 | H | 2,4-difluorophenyl | 5-OH-6-Me |
| 62 | H | 4-acetamidophenyl | 5-OH-6-OMe |
| 63 | H | 4-acetamidophenyl | 5,6-diOMe |
| 64 | H | 4-acetamidophenyl | 5-OH-6-Me |
| 65 | H | 4-(acetamidomethyl)phenyl | 5-OH-6-OMe |
| 66 | H | 4-(acetamidomethyl)phenyl | 5,6-diOH |
| 67 | H | 4-(acetamidomethyl)phenyl | 5,6-diOMe |
| 68 | H | 4-(acetamidomethyl)phenyl | 5-OH-6-N(Me)₂ |
| 69 | H | 4-(acetamidomethyl)phenyl | 5-OH-6-Me |
| 70 | H | 4-pyrimidinyl | 5-OH-6-OMe |
| 71 | H | 4-pyrimidinyl | 5,6-diOH |
| 72 | H | 4-pyrimidinyl | 5,6-diOMe |
| 73 | H | 4-pyrimidinyl | 5-OH-6-Me |
| 74 | H | 2-(acetamido)ethyl | 5-OH-6-OMe |
| 75 | H | 2-(acetamido)ethyl | 5,6-diOH |
| 76 | H | 2-(acetamido)ethyl | 5,6-diOMe |
| 77 | H | 2-(acetamido)ethyl | 5-OH-6-N(Me)₂ |
| 78 | H | 2-(acetamido)ethyl | 5-OH-6-Me |
| 79 | H | 4-thiazolyl | 5-OH-6-OMe |
| 80 | H | 4-thiazolyl | 5,6-diOH |
| 81 | H | 4-thiazolyl | 5,6-diOMe |
| 82 | H | 4-thiazolyl | 5-OH-6-N(Me)₂ |
| 83 | H | 4-thiazolyl | 5-OH-6-Me |
| 84 | H | 3-pyridinyl | 5-OH-6-OMe |
| 85 | H | 3-pyridinyl | 5,6-diOH |
| 86 | H | 3-pyridinyl | 5,6-diOMe |
| 87 | H | 3-pyridinyl | 5-OH-6-N(Me)2 |
| 88 | H | 3-pyridinyl | 5-OH-6-Me |
| 89 | H | 3,4,5-trimethoxyphenyl | 5-OH-6-OMe |
| 90 | H | 3,4,5-trimethoxyphenyl | 5-OMe |
| 91 | H | 3,4,5-trimethoxyphenyl | 6-OMe |
| 92 | H | 3,4,5-trimethoxyphenyl | 5,7-diOMe |
| 93 | H | 3,4,5-trimethoxyphenyl | 5-OH |
| 94 | H | 3,4,5-trimethoxyphenyl | 6-F |
| 95 | H | 4-nitrophenyl | 5-OH-6-OMe |
| 96 | H | 4-aminophenyl | 5-OH-6-OMe |
| 97 | 6-F | 4-fluorophenyl | 5-OH-6-OMe |
| 98 | 6-F | 4-fluorophenyl | 5-OMe |
| 99 | 6-F | 4-fluorophenyl | 6-OMe |
| 100 | 6-F | 4-fluorophenyl | 5,7-diOMe |
| 101 | 6-F | 4-fluorophenyl | 5-OH |
| 102 | 6-F | 4-fluorophenyl | 6-F |
| 103 | 6-F | 3,4,5-trimethoxyphenyl | 5-OH-6-OMe |
| 104 | 6-F | 3,4,5-trimethoxyphenyl | 5-OMe |
| 105 | 6-F | 3,4,5-trimethoxyphenyl | 6-OMe |
| 106 | 6-F | 3,4,5-trimethoxyphenyl | 5,7-diOMe |
| 107 | 6-F | 3,4,5-trimethoxyphenyl | 5-OH |
| 108 | 6-F | 3,4,5-trimethoxyphenyl | 6-F |
| 109 | 6,7-diOMe | 4-fluorophenyl | 5-OH-6-OMe |
| 110 | 6,7-diOMe | 4-fluorophenyl | 5-OMe |
| 111 | 6,7-diOMe | 4-fluorophenyl | 6-OMe |
| 112 | 6,7-diOMe | 4-fluorophenyl | 5,7-diOMe |
| 113 | 6,7-diOMe | 4-fluorophenyl | 5-OH |
| 114 | 6,7-diOMe | 4-fluorophenyl | 6-F |
| 115 | 6,7-diOMe | 3,4,5-trimethoxyphenyl | 5-OH-6-OMe |
| 116 | 6,7-diOMe | 3,4,5-trimethoxyphenyl | 5-OMe |
| 117 | 6,7-diOMe | 3,4,5-trimethoxyphenyl | 6-OMe |
| 118 | 6,7-diOMe | 3,4,5-trimethoxyphenyl | 5,7-diOMe |
| 119 | 6,7-diOMe | 3,4,5-trimethoxyphenyl | 5-OH |
| 120 | 6,7-diOMe | 3,4,5-trimethoxyphenyl | 6-F |

Preparation of 2-[[2-(4-fluorophenyl)quinazolin-4-yl]carbonyl]-5-hydroxy-6-methoxy-1,2,3,4-tetrahydroisoquinoline (compound 1)

Into a 50-mL 3-necked round-bottom flask purged and maintained with an inert atmosphere of nitrogen, was placed 2-(4-fluorophenyl)quinazoline-4-carboxylic acid (100 mg, 0.37 mmol, 1.00 equiv), 5-hydroxy-6-methoxy-1,2,3,4-tetrahydroisoquinoline hydrochloride (88 mg, 0.41 mmol, 1.10 equiv), oxolane (10 mL), O-(7-Azabenzotriazol-1-yl)-N,N,N',N'-tetramethyluronium hexafluorophosphate (HATU, 170 mg, 0.45 mmol, 1.20 equiv) and DIEA (241 mg, 1.87 mmol, 5.00 equiv). The resulting solution was stirred overnight at room temperature. The resulting solution was diluted with 100 mL of ethyl acetate. The resulting mixture was washed with 1×100 mL of saturated aqueous sodium bicarbonate, 1×100 mL of ammonia (5%) and 1×100 mL of brine. The mixture was dried over anhydrous sodium sulfate and concentrated under vacuum. The residue was applied onto a silica gel column with ethyl acetate/petroleum ether (1:5-1:1) or purified by Prep-HPLC with the following conditions (Sunfire Prep): Column, C18 Sum 15*190 mm; mobile phase, A: HCOOH B: CH₃CN; Detector, UV 254 nm. This resulted in 30 mg (19%) of 2-[[2-(4-fluorophenyl)quinazolin-4-yl]carbonyl]-5-hydroxy-6-methoxy-1,2,3,4-tetrahydroisoquinoline as a yellow solid. ¹H NMR (300 MHz, DMSO-d₆) δ 2.62 and 2.90 (2t, 2H), 3.48 and 4.03 (2t, 2H), 3.74 and 3.80 (2s, 3H), 4.39 and 4.92 (2s, 2H), 6.30-6.33 (m, 0.4H), 6.69-6.78 (m, 1H), 6.90-6.92 (m, 0.6H), 7.36-7.44 (m, 2.7H), 7.69-7.79 (m, 1H), 7.86-7.97 (m, 1H), 8.06-8.17 (m, 2H), 8.53-8.61 (m, 2H), 8.69 and 8.73 (2s, 1H); ¹⁹F (282 MHz, DMSO-d₆) δ −110.2; MS (ESI) m/z 430 ([M+H]⁺).

Preparation of 2-[[2-(4-fluorophenyl)quinazolin-4-yl]carbonyl]-5,6-dihydroxy-1,2,3,4-tetrahydroisoquinoline (compound 2)

Into a 50-mL round-bottom flask purged and maintained with an inert atmosphere of nitrogen, was placed Compound 1 (2-[[2-(4-fluorophenyl)quinazolin-4-yl]carbonyl]-5-hydroxy-6-methoxy-1,2,3,4-tetrahydroisoquinoline, 35 mg, 0.08 mmol, 1.00 equiv) and dichloromethane (5 mL). This was followed by the addition of BBr₃ (0.15 mL) at 0° C. The resulting solution was stirred for 1 h at room temperature. The reaction was then quenched by the addition of 1.5 mL of methanol/water=1:1. The resulting mixture was concentrated under vacuum. The resulting solution was diluted with 10 mL of dichloromethane. The pH value of the solution was adjusted to 8-9 with triethylamine. The resulting mixture was concentrated under vacuum. The crude product was purified by Prep-HPLC with the following conditions (Sunfire Prep): Column, C18 5 μm 15*190 mm; mobile phase, A: HCOOH B: CH₃CN; Detector, UV 254 nm. This resulted in 11.3 mg of compound 2 (33% yield) as a brown solid. ¹H NMR (300 MHz, DMSO-d₆) δ 2.61 and 2.89 (2t, 2H), 3.47 and 4.02 (2t, 2H), 4.34 and 4.87 (2s, 2H), 6.16 and 6.62 (2d, 1H), 6.51 and 6.72 (2d, 1H), 7.36-7.44 (m, 2H), 7.69-7.79 (m, 1H), 7.86-7.97 (2d, 1H), 8.06-8.17 (m, 2H), 8.39 (b, 1H), 8.53-8.62 (m, 2H), 9.12 (m, 1H); MS (ESI) m/z 416 ([M+H]⁺).

Preparation of 2-[[2-(4-fluorophenyl)quinazolin-4-yl]carbonyl]-5,6-dimethoxy-1,2,3,4-tetrahydroisoquinoline (compound 3)

Reaction of 2-(4-fluorophenyl)quinazoline-4-carboxylic acid with 5,6-dimethoxy-1,2,3,4-tetrahydroisoquinoline hydrochloride gave compound 3 (10% yield) as a white solid.

¹H NMR (300 MHz, DMSO-d₆) δ 2.72 and 2.98 (2t, 2H), 3.49 and 4.03 (2t, 2H), 3.68 and 3.75 (2s, 3H), 3.76 and 3.81 (2s, 3H), 4.42 and 4.93 (2s, 2H), 6.63 and 7.01 (2d, 1H), 6.81 and 7.08 (2d, 1H), 7.37-7.44 (m, 2H), 7.76-7.79 (m, 1H), 7.89-7.99 (2d, 1H), 8.07-8.15 (m, 2H), 8.53-8.62 (m, 2H); MS (ESI) m/z 444 ([M+H]⁺).

Preparation of 2-[[2-(4-fluorophenyl)quinazolin-4-yl]carbonyl]-5-hydroxy-6-dimethylamino-1,2,3,4-tetrahydroisoquinoline (compound 4)

Reaction of 2-(4-fluorophenyl)quinazoline-4-carboxylic acid with 5-hydroxy-6-dimethylamino-1,2,3,4-tetrahydroisoquinoline hydrochloride gave compound 4 (5% yield) as a brown solid. ¹H NMR (300 MHz, CDCl₃) δ 2.71 and 3.17 (2d, 6H), 2.85 and 3.09 (2t, 2H), 3.58 and 4.21 (2t, 2H), 4.48 and 5.09 (2s, 2H), 6.36 and 6.84 (2d, 1H), 6.96-7.25 (m, 3H), 7.57-8.15 (m, 5H), 8.62-8.69 (m, 2H); MS (ESI) m/z 443 ([M+H]⁺).

Preparation of 2-[[2-(4-fluorophenyl)quinazolin-4-yl]carbonyl]-5-hydroxy-6-methyl-1,2,3,4-tetrahydroisoquinoline (compound 5)

Reaction of 2-(4-fluorophenyl)quinazoline-4-carboxylic acid with 5-hydroxy-6-methyl-1,2,3,4-tetrahydroisoquinoline hydrochloride gave compound 5 (9% yield) as a white solid. ¹H NMR (300 MHz, DMSO-d₆) δ 2.13 and 2.17 (2s, 3H), 2.65 and 2.92 (2t, 2H), 3.50 and 4.05 (2t, 2H), 4.41 and 4.93 (2s, 2H), 6.29-7.00 (4d, 2H), 7.36-7.44 (m, 2H), 7.69-7.79 (m, 1H), 7.86-7.98 (2d, 1H), 8.06-8.18 (m, 2H), 8.37 and 8.44 (2s, 1H), 8.52-8.59 (m, 2H); MS (ESI) m/z 414 ([M+H]⁺).

Preparation of 2-[[2-(4-fluorophenyl)quinazolin-4-yl]carbonyl]-5-methoxy-1,2,3,4-tetrahydroisoquinoline (compound 6)

Reaction of 2-(4-fluorophenyl)quinazoline-4-carboxylic acid with 5-methoxy-1,2,3,4-tetrahydroisoquinoline hydrochloride gave compound 6 (23.7% yield). ¹H NMR (400 MHz, CDCl₃) δ 2.79 and 3.05 (2t, 2H), 3.56 and 4.21 (2t, 2H), 3.84 and 3.89 (2s, 3H), 4.52 and 5.13 (2s, 2H), 6.41-6.43 (m, 0.3H), 6.77-6.80 (m, 1H), 6.91-6.93 (m, 0.7H), 7.10 (m, 0.3H), 7.19-7.30 (m, 2.7H), 7.58-7.65 (m, 1H), 7.93-7.98 (m, 1.3H), 8.02-8.04 (m, 0.7H), 8.15-8.19 (m, 1H), 8.63-8.71 (m, 2H); ¹⁹F (376 MHz, CDCl₃) δ −110.0; MS (ESI) m/z 414 ([M+H]⁺).

Preparation of 2-[[2-(4-fluorophenyl)quinazolin-4-yl]carbonyl]-6-methoxy-1,2,3,4-tetrahydroisoquinoline (compound 7)

Reaction of 2-(4-fluorophenyl)quinazoline-4-carboxylic acid with 6-methoxy-1,2,3,4-tetrahydroisoquinoline hydrochloride gave compound 7 (23.5% yield): ¹H NMR (400 MHz, CDCl₃) δ 2.87 and 3.11 (2t, 2H), 3.58 and 4.19 (2t, 2H), 3.81 and 3.84 (2s, 3H), 4.47 and 5.08 (2s, 2H), 6.68-6.90 (m, 2H), 7.20-7.25 (m, 3H), 7.57-7.66 (m, 1H), 7.93-8.06 (m, 2H), 8.19-8.21 (d, 8.65-8.71 (m, 2H); ¹⁹F (282 MHz, CDCl₃) δ −109.5; MS (ESI) m/z 414 ([M+H]⁺).

Preparation of 2-[[2-(4-fluorophenyl)quinazolin-4-yl]carbonyl]-5,7-dimethoxy-1,2,3,4-tetrahydroisoquinoline (compound 8)

Reaction of 2-(4-fluorophenyl)quinazoline-4-carboxylic acid with 5,7-dimethoxy-1,2,3,4-tetrahydroisoquinoline hydrochloride gave compound 8 (23.5% yield): ¹H NMR (300 MHz, DMSO-d₆) δ 2.70 and 3.00 (2m, 2H), 3.48 and 4.03 (2m, 2H), 3.74 and 3.75 (m, 3H), 3.46 and 3.87 (s, 3H), 4.24 and 4.78 (2s, 2H), 6.33-6.51 (m, 2H), 7.38-7.44 (m, 2H), 7.72-7.78 (m, 1H), 7.91-7.99 (m, 1H), 8.07-8.17 (m, 2H), 8.52-8.62 (m, 2H); MS (ESI) m/z 444 ([M+H]⁺).

Preparation of 2-[[2-(4-fluorophenyl)quinazolin-4-yl]carbonyl]-5-hydroxy-1,2,3,4-tetrahydroisoquinoline (compound 9)

Reaction of 2-(4-fluorophenyl)quinazoline-4-carboxylic acid with 5-hydroxy-1,2,3,4-tetrahydroisoquinoline hydrochloride gave compound 9 (24.2% yield): ¹H NMR (300 MHz, DMSO-d₆) δ 2.60 and 2.87 (2t, 2H), 3.51 and 4.07 (2t, 2H), 4.45 and 4.96 (2s, 2H), 6.32-6.79 (m, 2H), 6.88 and 7.08 (2t, 1H), 7.37-7.44 (m, 2H), 7.70-7.79 (m, 1H), 7.88-7.99 (2d, 1H), 8.07-8.18 (m, 2H), 8.53-8.62 (m, 2H), 9.50 and 9.55 (2s, 1H); ¹⁹F (282 MHz, DMSO-d₆) δ −110.0; MS (ESI) m/z 400 ([M+H]⁺).

Preparation of 2-[[2-(4-fluorophenyl)quinazolin-4-yl]carbonyl]-5-fluoro-1,2,3,4-tetrahydroisoquinoline (compound 10)

Reaction of 2-(4-fluorophenyl)quinazoline-4-carboxylic acid with 5-fluoro-1,2,3,4-tetrahydroisoquinoline hydrochloride gave compound 10 (27.0% yield) as a white solid. ¹H NMR (400 MHz, CDCl₃) δ 2.88 and 3.13 (2t, 2H), 3.64 and 4.24 (2t, 2H), 4.58 and 5.14 (2s, 2H), 6.68-7.33 (m, 5H), 7.65-7.77 (m, 1H), 7.94-8.10 (m, 2H), 8.15-8.20 (m, 1H), 8.57-8.67 (m, 2H); ¹⁹F (282 MHz, DMSO-d₆) δ −112.0, −121.0; MS (ESI) m/z 402 ([M+H]⁺).

Preparation of 2-[[2-(4-fluorophenyl)quinazolin-4-yl]carbonyl]-6-fluoro-1,2,3,4-tetrahydroisoquinoline (compound 11)

Reaction of 2-(4-fluorophenyl)quinazoline-4-carboxylic acid with 6-fluoro-1,2,3,4-tetrahydroisoquinoline hydrochloride gave compound 11 (24.0% yield) as a white solid. ¹H NMR (400 MHz, CDCl₃) δ 2.90 and 3.13 (2t, 2H), 3.59 and 4.20 (2t, 2H), 4.51 and 5.10 (2s, 2H), 6.79-7.27 (m, 5H), 7.59-7.66 (m, 1H), 7.95-8.05 (m, 2H), 8.16-8.18 (m, 1H), 8.63-8.69 (m, 2H); ¹⁹F (282 MHz, DMSO-d₆) δ −109.7, −115.1, −115.6; MS (ESI) m/z 402 ([M+H]⁺).

Preparation of 2-[[2-(4-methylphenyl)quinazolin-4-yl]carbonyl]-5-hydroxy-6-methoxy-1,2,3,4-tetrahydroisoquinoline (compound 12)

Reaction of 2-(4-methylphenyl)quinazoline-4-carboxylic acid with 5-hydroxy-6-methoxy-1,2,3,4-tetrahydroisoquinoline hydrochloride gave compound 12 (36% yield) as a white solid. ¹H NMR (300 MHz, DMSO-d₆) δ 2.41 (s, 3H), 2.63 and 2.90 (2t, 2H), 3.47 and 4.03 (2t, 2H), 3.74 and 3.80 (2s, 3H), 4.38 and 4.92 (2s, 2H), 6.32 and 6.77 (2d, 1H), 6.70 and 6.91 (2d, 1H), 7.36-7.41 (m, 2H), 7.67-7.77 (m, 1H), 7.84-7.95 (2d, 1H), 8.04-8.15 (m, 2H), 8.39-8.45 (m, 2H), 8.68 and 8.72 (2s, 1H); MS (ESI) m/z 426 ([M+H]⁺).

Preparation of 2-[[2-(4-methylphenyl)quinazolin-4-yl]carbonyl]-5,6-dihydroxy-1,2,3,4-tetrahydroisoquinoline (compound 13)

2-[[2-(4-methylphenyl)quinazolin-4-yl]carbonyl]-5,6-dihydroxy-1,2,3,4-tetrahydroisoquinoline was obtained from compound 12 (43% yield, white solid) by the same way with the preparation of compound 2. $^1$H NMR (300 MHz, CDCl$_3$) δ 2.46 (s, 3H), 2.79 and 3.02 (2t, 2H), 3.55 and 4.16 (2t, 2H), 4.41 and 5.01 (2s, 2H), 5.58 (b, 1H), 5.90 (b, 1H), 6.17 and 6.63 (2d, 1H), 6.57 and 6.77 (2d, 1H), 7.28-7.36 (m, 2H), 7.51-7.62 (m, 1H), 7.88-8.00 (m, 2H), 8.14-8.16 (m, 1H), 8.48-8.54 (m, 2H); MS (ESI) m/z 412 ([M+H]$^+$).

Preparation of 2-[[2-(4-methylphenyl)quinazolin-4-yl]carbonyl]-5,6-dimethoxy-1,2,3,4-tetrahydroisoquinoline (compound 14)

Reaction of 2-(4-methylphenyl)quinazoline-4-carboxylic acid with 5,6-dimethoxy-1,2,3,4-tetrahydroisoquinoline hydrochloride gave compound 14 (17% yield) as a white solid. $^1$H NMR (300 MHz, DMSO-d$_6$) δ 2.41 (s, 3H), 2.73 and 2.98 (2t, 2H), 3.48 and 4.03 (2t, 2H), 3.69 and 3.75 (2s, 3H), 3.76 and 3.82 (2s, 3H), 4.41 and 4.93 (2s, 2H), 6.62 and 7.01 (2d, 1H), 6.80 and 7.08 (2d, 1H), 7.37-7.41 (m, 2H), 7.67-7.77 (m, 1H), 7.86-7.98 (2d, 1H), 8.04-8.16 (m, 2H), 8.40-8.43 (m, 2H); MS (ESI) m/z 440 ([M+H]$^+$).

Preparation of 2-[[2-(4-methylphenyl)quinazolin-4-yl]carbonyl]-5-hydroxy-6-dimethylamino-1,2,3,4-tetrahydroisoquinoline (compound 15)

Reaction of 2-(4-methylphenyl)quinazoline-4-carboxylic acid with 5-hydroxy-6-dimethylamino-1,2,3,4-tetrahydroisoquinoline hydrochloride gave compound 15 (13% yield) as a brown solid. $^1$H NMR (300 MHz, CDCl$_3$) δ 2.41 (s, 3H), 2.67 and 3.18 (2d, 6H), 2.84 and 3.08 (2t, 2H), 3.59 and 4.21 (2t, 2H), 4.49 and 5.09 (2s, 2H), 6.33 and 6.82 (2d, 1H), 6.96 and 7.15 (2d, 1H), 7.33-7.37 (m, 2H), 7.55-8.15 (m, 5H), 8.51-8.56 (m, 2H); MS (ESI) m/z 439 ([M+H]$^+$).

Preparation of 2-[[2-(4-methylphenyl)quinazolin-4-yl]carbonyl]-5-hydroxy-6-methyl-1,2,3,4-tetrahydroisoquinoline (compound 16)

Reaction of 2-(4-methylphenyl)quinazoline-4-carboxylic acid with 5-hydroxy-6-methyl-1,2,3,4-tetrahydroisoquinoline hydrochloride gave compound 16 (30% yield) as a white solid. $^1$H NMR (300 MHz, CDCl$_3$) δ 2.25 and 2.28 (2s, 3H), 2.48 (s, 3H), 2.81 and 3.05 (2t, 2H), 3.60 and 4.23 (2t, 2H), 4.50 and 5.09 (2s, 2H), 6.36-6.92 (m, 2H), 7.08 (2d, 1H), 7.37-7.64 (m, 3H), 7.97-8.06 (m, 2H), 8.37 (m, 1H), 8.60 (m, 2H); MS (ESI) m/z 410 ([M+H]$^+$).

Preparation of 2-[[2-phenylquinazolin-4-yl]carbonyl]-5-hydroxy-6-methoxy-1,2,3,4-tetrahydroisoquinoline (compound 17)

Reaction of 2-phenylquinazoline-4-carboxylic acid with 5-hydroxy-6-methoxy-1,2,3,4-tetrahydroisoquinoline hydrochloride gave compound 17 (18. % yield) as a white solid. $^1$H NMR (300 MHz, DMSO-d$_6$) δ 2.63 and 2.90 (2t, 2H), 3.49 and 4.04 (2t, 2H), 3.74 and 3.80 (2s, 3H), 4.39 and 4.92 (2s, 2H), 6.32 and 6.77 (2d, 1H), 6.70 and 6.91 (2d, 1H), 7.57-7.60 (m, 3H), 7.69-7.79 (m, 1H), 7.86-7.98 (2d, 1H), 8.06-8.18 (m, 2H), 8.50-8.56 (m, 2H), 8.68 and 8.72 (2s, 1H); MS (ESI) m/z 412 ([M+H]$^+$).

Preparation of 2-[[2-phenylquinazolin-4-yl]carbonyl]-5,6-dihydroxy-1,2,3,4-tetrahydroisoquinoline (compound 18)

2-[[2-phenylquinazolin-4-yl]carbonyl]-5,6-dihydroxy-1,2,3,4-tetrahydroisoquinoline was obtained from compound 17 (15% yield, light yellow solid) by the same way with the preparation of compound 2. $^1$H NMR (300 MHz, CDCl$_3$) δ 2.82 and 3.06 (2t, 2H), 3.57 and 4.19 (2t, 2H), 4.43 and 5.03 (2s, 2H), 5.58 (b, 1H), 5.90 (b, 1H), 6.21 and 6.69 (2d, 1H), 6.62 and 6.82 (2d, 1H), 7.55-7.80 (m, 4H), 8.01-8.11 (m, 2H), 8.70-8.85 (m, 3H); MS (ESI) m/z 398 ([M+H]$^+$).

Preparation of 2-[[2-phenylquinazolin-4-yl]carbonyl]-5,6-dimethoxy-1,2,3,4-tetrahydroisoquinoline (compound 19)

Reaction of 2-phenylquinazolin-4-carboxylic acid with 5,6-dimethoxy-1,2,3,4-tetrahydroisoquinoline hydrochloride gave compound 19 (11% yield) as a white solid. $^1$H NMR (300 MHz, DMSO-d$_6$) δ 2.73 and 2.99 (2t, 2H), 3.49 and 4.04 (2t, 2H), 3.69 and 3.75 (2s, 3H), 3.76 and 3.81 (2s, 3H), 4.42 and 4.94 (2s, 2H), 6.63 and 7.01 (2d, 1H), 6.80 and 7.08 (2d, 1H), 7.57-7.60 (m, 3H), 7.77-7.79 (m, 1H), 7.89-8.00 (2d, 1H), 8.07-8.19 (m, 2H), 8.50-8.57 (m, 2H); MS (ESI) m/z 426 ([M+H]$^+$).

Preparation of 2-[[2-phenylquinazolin-4-yl]carbonyl]-5-hydroxy-6-dimethylamino-1,2,3,4-tetrahydroisoquinoline (compound 20)

Reaction of 2-phenylquinazolin-4-carboxylic acid with 5-hydroxy-6-dimethylamino-1,2,3,4-tetrahydroisoquinoline hydrochloride gave compound 20 (9% yield) as a brown solid. $^1$H NMR (300 MHz, CDCl$_3$) δ 2.66 and 3.18 (2d, 6H), 2.85 and 3.09 (2t, 2H), 3.60 and 4.21 (2t, 2H), 4.50 and 5.09 (2s, 2H), 6.35 and 6.82 (2d, 1H), 6.96 and 7.15 (2d, 1H), 7.53-7.64 (m, 4H), 7.92-8.18 (m, 3H), 8.62-8.68 (m, 2H); MS (ESI) m/z 425 ([M+H]$^+$).

Preparation of 2-[[2-phenylquinazolin-4-yl]carbonyl]-5-hydroxy-6-methyl-1,2,3,4-tetrahydroisoquinoline (compound 21)

Reaction of 2-phenylquinazolin-4-carboxylic acid with 5-hydroxy-6-methyl-1,2,3,4-tetrahydroisoquinoline hydrochloride gave compound 21 (14% yield) as a white solid. $^1$H NMR (300 MHz, CDCl$_3$) δ 2.13 and 2.17 (2s, 3H), 2.66 and 2.92 (2t, 2H), 3.50 and 4.05 (2t, 2H), 4.41 and 4.93 (2s, 2H), 6.29-7.00 (4d, 2H), 7.56-7.80 (m, 4H), 7.86-7.98 (2d, 1H), 8.10-8.19 (m, 2H), 8.37 and 8.44 (2s, 1H), 8.49-8.57 (m, 2H); MS (ESI) m/z 396 ([M+H]$^+$).

Preparation of 2-[[2-(4-methoxyphenyl)quinazolin-4-yl]carbonyl]-5-hydroxy-6-methoxy-1,2,3,4-tetrahydroisoquinoline (compound 22)

Reaction of 2-(4-methoxyphenyl)quinazoline-4-carboxylic acid with 5-hydroxy-6-methoxy-1,2,3,4-tetrahydroisoquinoline hydrochloride gave compound 22 (16% yield) as a yellow solid. $^1$H NMR (300 MHz, DMSO-d$_6$) δ 2.65 and 2.89 (2t, 2H), 3.47 and 4.03 (2t, 2H), 3.74-3.87 (3s, 6H), 4.38 and 4.91 (2s, 2H), 6.32 and 6.77 (2d, 1H), 6.70 and 6.91 (2d, 1H), 7.09-7.15 (m, 2H), 7.63-7.73 (m, 1H), 7.81-7.93 (2d, 1H), 8.02-8.12 (m, 2H), 8.44-8.51 (m, 2H), 8.68 and 8.73 (2s, 1H); MS (ESI) m/z 442 ([M+H]$^+$).

Preparation of 2-[[2-(4-methoxyphenyl)quinazolin-4-yl]carbonyl]-5,6-dihydroxy-1,2,3,4-tetrahydroisoquinoline (compound 23)

Reaction of 2-(4-methoxyphenyl)quinazoline-4-carboxylic acid with 5,6-dihydroxy-1,2,3,4-tetrahydroisoquinoline hydrobromide gave compound 23 (9% yield) as brown oil. $^1$H NMR (300 MHz, DMSO-d$_6$) δ 2.62 and 2.88 (2t, 2H), 3.46 and 4.01 (2t, 2H), 3.87 (s, 3H), 4.33 and 4.87 (2s, 2H), 6.16 and 6.62 (2d, 1H), 6.51 and 6.72 (2d, 1H), 7.09-7.15 (m, 2H), 7.63-7.74 (m, 1H), 7.80-7.92 (2d, 1H), 8.02-8.12 (m, 2H), 8.44-8.51 (m, 2H); MS (ESI) m/z 428 ([M+H]$^+$).

Preparation of 2-[[2-(4-methoxylphenyl)quinazolin-4-yl]carbonyl]-5,6-dimethoxy-1,2,3,4-tetrahydroisoquinoline (compound 24)

Reaction of 2-(4-methoxylphenyl)quinazoline-4-carboxylic acid with 5,6-dimethoxy-1,2,3,4-tetrahydroisoquinoline hydrochloride gave compound 24 (13% yield) as a light yellow solid. $^1$H NMR (300 MHz, DMSO-d$_6$) δ 2.72 and 2.98 (2t, 2H), 3.48 and 4.03 (2t, 2H), 3.69-3.87 (5s, 9H), 4.41 and 4.93 (2s, 2H), 6.63 and 7.01 (2d, 1H), 6.80 and 7.08 (2d, 1H), 7.11-7.14 (m, 2H), 7.71-7.74 (m, 1H), 7.83-7.95 (2d, 1H), 8.03-8.10 (m, 2H), 8.45-8.51 (m, 2H); MS (ESI) m/z 456 ([M+H]$^+$).

Preparation of 2-[[2-(4-methoxylphenyl)quinazolin-4-yl]carbonyl]-5-hydroxy-6-dimethylamino-1,2,3,4-tetrahydroisoquinoline (compound 25)

Reaction of 2-(4-methoxylphenyl)quinazoline-4-carboxylic acid with 5-hydroxy-6-dimethylamino-1,2,3,4-tetrahydroisoquinoline hydrochloride gave compound 25 (14% yield) as a brown solid. $^1$H NMR (300 MHz, CDCl$_3$) δ 2.64 and 2.69 (d, 6H), 2.85 and 3.09 (2t, 2H), 3.59 and 4.20 (2t, 2H), 3.92 (s, 3H), 4.49 and 5.09 (2s, 2H), 6.33 and 6.82 (2d, 1H), 6.96 and 7.15 (2d, 1H), 7.03-7.07 (m, 2H), 7.50-7.60 (m, 1H), 7.86-8.01 (m, 2H), 8.08-8.12 (m, 1H), 8.57-8.63 (m, 2H); MS (ESI) m/z 455 ([M+H]$^+$).

Preparation of 2-[[2-(4-methoxylphenyl)quinazolin-4-yl]carbonyl]-5-hydroxy-6-methyl-1,2,3,4-tetrahydroisoquinoline (compound 26)

Reaction of 2-(4-methoxylphenyl)quinazoline-4-carboxylic acid with 5-hydroxy-6-methyl-1,2,3,4-tetrahydroisoquinoline hydrochloride gave compound 26 (22% yield) as a yellow solid. $^1$H NMR (300 MHz, CDCl$_3$) δ 2.25 and 2.28 (2s, 3H), 2.81 and 3.04 (2t, 2H), 3.60 and 4.22 (2t, 2H), 3.93 (s, 3H), 4.49 and 5.09 (2s, 2H), 6.34-6.93 (m, 2H), 7.05-7.09 (m, 3H), 7.56-7.64 (m, 1H), 7.94-8.04 (m, 2H), 8.32-8.33 (m, 1H), 8.64-8.70 (m, 2H); MS (ESI) m/z 426 ([M+H]$^+$).

Preparation of 2-[[2-(4-chlorophenyl)quinazolin-4-yl]carbonyl]-5-hydroxy-6-methoxy-1,2,3,4-tetrahydroisoquinoline (compound 27)

Reaction of 2-(4-chlorophenyl)quinazoline-4-carboxylic acid with 5-hydroxy-6-methoxy-1,2,3,4-tetrahydroisoquinoline hydrochloride gave compound 27 (11% yield) as off-white oil. $^1$H NMR (300 MHz, DMSO-d$_6$) δ 2.62 and 2.90 (2t, 2H), 3.48 and 4.03 (2t, 2H), 3.74-3.80 (2s, 3H), 4.39 and 4.92 (2s, 2H), 6.31 and 6.77 (2d, 1H), 6.71 and 6.91 (2d, 1H), 7.62-7.81 (m, 3H), 7.87-7.98 (2d, 1H), 8.07-8.19 (m, 2H), 8.50-8.56 (m, 2H), 8.67 and 8.72 (2s, 1H); MS (ESI) m/z 446 ([M+H]$^+$).

Preparation of 2-[[2-(4-chlorophenyl)quinazolin-4-yl]carbonyl]-5,6-dihydroxy-1,2,3,4-tetrahydroisoquinoline (compound 28)

2-[[2-(4-chlorophenyl)quinazolin-4-yl]carbonyl]-5,6-dihydroxy-1,2,3,4-tetrahydroisoquinoline was obtained from compound 27 (18% yield, white solid) by the same way with the preparation of compound 2. $^1$H NMR (300 MHz, CDCl$_3$) δ 2.82 and 3.06 (2t, 2H), 3.57 and 4.20 (2t, 2H), 4.43 and 5.05 (2s, 2H), 5.43 (b, 1H), 6.23 and 6.71 (2d, 1H), 6.63 and 6.81 (2d, 1H), 7.48-7.56 (m, 2H), 7.59-7.67 (m, 1H), 7.95-8.04 (m, 2H), 8.18-8.20 (m, 1H), 8.57-8.63 (m, 2H); MS (ESI) m/z 432 ([M+H]$^+$).

Preparation of 2-[[2-(4-chlorophenyl)quinazolin-4-yl]carbonyl]-5,6-dimethoxy-1,2,3,4-tetrahydroisoquinoline (compound 29)

Reaction of 2-(4-chlorophenyl)quinazoline-4-carboxylic acid with 5,6-dimethoxy-1,2,3,4-tetrahydroisoquinoline hydrochloride gave compound 29 (10% yield) as a white solid. $^1$H NMR (300 MHz, DMSO-d$_6$) δ 2.71 and 2.98 (2t, 2H), 3.49 and 4.03 (2t, 2H), 3.68-3.81 (4s, 6H), 4.42 and 4.93 (2s, 2H), 6.62 and 7.01 (2d, 1H), 6.81 and 7.08 (2d, 1H), 7.63-7.67 (m, 2H), 7.71-7.81 (m, 1H), 7.89-8.00 (2d, 1H), 8.08-8.16 (m, 2H), 8.50-8.57 (m, 2H); MS (ESI) m/z 460 ([M+H]$^+$).

Preparation of 2-[[2-(4-chlorophenyl)quinazolin-4-yl]carbonyl]-5-hydroxy-6-dimethylamino-1,2,3,4-tetrahydroisoquinoline (compound 30)

Reaction of 2-(4-chlorophenyl)quinazoline-4-carboxylic acid with 5-hydroxy-6-dimethylamino-1,2,3,4-tetrahydroisoquinoline hydrochloride gave compound 30 (8% yield) as a brown solid. $^1$H NMR (300 MHz, CDCl$_3$) δ 2.74-3.10 (m, 8H), 3.58 and 4.21 (2t, 2H), 4.48 and 5.10 (2s, 2H), 6.34 and 6.88 (2d, 1H), 6.96 and 7.17 (2d, 1H), 7.48-8.16 (m, 7H), 8.57-8.62 (m, 2H); MS (ESI) m/z 459 ([M+H]$^+$).

Preparation of 2-[[2-(4-chlorophenyl)quinazolin-4-yl]carbonyl]-5-hydroxy-6-methyl-1,2,3,4-tetrahydroisoquinoline (compound 31)

Reaction of 2-(4-chlorophenyl)quinazoline-4-carboxylic acid with 5-hydroxy-6-methyl-1,2,3,4-tetrahydroisoquinoline hydrochloride gave compound 31 (29% yield) as a white solid. $^1$H NMR (300 MHz, CDCl$_3$) δ 2.22 and 2.25 (2s, 3H), 2.78 and 3.03 (2t, 2H), 3.54 and 4.17 (2t, 2H), 4.43 and 5.05 (2s, 2H), 6.27-6.75 (m, 2H), 6.85-7.03 (m, 3H), 7.45-7.63 (m, 3H), 7.90-8.01 (m, 2H), 8.08-8.12 (m, 1H), 8.52-8.59 (m, 2H); MS (ESI) m/z 430 ([M+H]$^+$).

Preparation of 2-[[2-(4-(dimethylamino)phenyl)quinazolin-4-yl]carbonyl]-5-hydroxy-6-methoxy-1,2,3,4-tetrahydroisoquinoline (compound 32)

Reaction of 2-(4-(dimethylamino)phenyl)quinazoline-4-carboxylic acid with 5-hydroxy-6-methoxy-1,2,3,4-tetrahydroisoquinoline hydrochloride gave compound 32 (20% yield) as a brown solid. $^1$H NMR (300 MHz, DMSO-d$_6$) δ 2.64 and 2.89 (2t, 2H), 3.04 (s, 6H), 3.47 and 4.02 (2t, 2H), 3.74 and 3.80 (2s, 3H), 4.37 and 4.90 (2s, 2H), 6.31-6.92 (m, 4H), 7.55-7.65 (m, 1H), 7.74-7.86 (2d, 1H), 7.96-8.01 (m, 2H), 8.32-8.38 (m, 2H), 8.68 and 8.71 (2s, 1H); MS (ESI) m/z 455 ([M+H]$^+$).

Preparation of 2-[[2-(4-(dimethylamino)phenyl)quinazolin-4-yl]carbonyl]-5,6-dihydroxy-1,2,3,4-tetrahydroisoquinoline (compound 33)

2-[[2-(4-(dimethylamino)phenyl)quinazolin-4-yl]carbonyl]-5,6-dihydroxy-1,2,3,4-tetrahydroisoquinoline was obtained from compound 32 (16% yield, yellow solid) by the same way with the preparation of compound 2. ¹H NMR (300 MHz, DMSO-d₆) δ 2.62 and 2.88 (2t, 2H), 3.03 (s, 6H), 3.46 and 4.01 (2t, 2H), 4.32 and 4.86 (2s, 2H), 6.17 and 6.62 (2d, 1H), 6.50 and 6.70 (2d, 1H), 6.80-6.90 (m, 2H), 7.57-8.01 (m, 4H), 8.30-8.40 (m, 3H), 9.17 (b, 1H); MS (ESI) m/z 441 ([M+H]⁺).

Preparation of 2-[[2-(4-(dimethylamino)phenyl)quinazolin-4-yl]carbonyl]-5,6-dimethoxy-1,2,3,4-tetrahydroisoquinoline (compound 34)

Reaction of 2-(4-(dimethylamino)phenyl)quinazoline-4-carboxylic acid with 5,6-dimethoxy-1,2,3,4-tetrahydroisoquinoline hydrochloride gave compound 34 (11% yield) as a brown solid, ¹H NMR (300 MHz, DMSO-d₆) δ 2.73 and 2.97 (2t, 2H), 3.03 (s, 6H), 3.47 and 4.02 (2t, 2H), 3.69-3.81 (4s, 6H), 4.40 and 4.92 (2s, 2H), 6.63 and 7.01 (2d, 1H), 6.80 and 7.07 (2d, 1H), 6.83-6.86 (m, 2H), 7.55-7.65 (m, 1H), 7.77-7.88 (2d, 1H), 7.96-8.02 (m, 2H), 8.32-8.38 (m, 2H); MS (ESI) m/z 469 ([M+H]⁺).

Preparation of 2-[[2-(4-(dimethylamino)phenyl)quinazolin-4-yl]carbonyl]-5-hydroxy-6-dimethylamino-1,2,3,4-tetrahydroisoquinoline (compound 35)

Reaction of 2-(4-(dimethylamino)phenyl)quinazoline-4-carboxylic acid with 5-hydroxy-6-dimethylamino-1,2,3,4-tetrahydroisoquinoline hydrochloride gave compound 35 (10% yield) as a brown solid. ¹H NMR (300 MHz, DMSO-d₆) δ 2.56 and 2.60 (2s, 6H), 2.73 and 2.89 (2t, 2H), 3.03 and 3.04 (2s, 6H), 3.47 and 4.03 (2t, 2H), 4.38 and 4.91 (2s, 2H), 6.76-7.02 (m, 4H), 7.56-8.01 (m, 5H), 8.31-8.39 (m, 2H); MS (ESI) m/z 468 ([M+H]⁺).

Preparation of 2-[[2-(4-(dimethylamino)phenyl)quinazolin-4-yl]carbonyl]-5-hydroxy-6-methyl-1,2,3,4-tetrahydroisoquinoline (compound 36)

Reaction of 2-(4-(dimethylamino)phenyl)quinazoline-4-carboxylic acid with 5-hydroxy-6-methyl-1,2,3,4-tetrahydroisoquinoline hydrochloride gave compound 36 (39% yield) as a brown solid. ¹H NMR (300 MHz, CDCl₃) δ 2.25 and 2.28 (2s, 3H), 2.81 and 3.03 (2t, 2H), 3.12 (s, 6H), 3.61 and 4.21 (2t, 2H), 4.50 and 5.08 (2s, 2H), 4.69 and 4.77 (2s, 1H), 6.36-7.09 (m, 4H), 7.48-7.56 (m, 1H), 7.88-7.98 (m, 2H), 8.20-8.23 (m, 1H), 8.56-8.61 (m, 2H); MS (ESI) m/z 439 ([M+H]⁺).

Preparation of 2-[[2-(4-(trifluoromethyl)phenyl)quinazolin-4-yl]carbonyl]-5-hydroxy-6-methoxy-1,2,3,4-tetrahydroisoquinoline (compound 37)

Reaction of 2-(4-(trifluoromethyl)phenyl)quinazoline-4-carboxylic acid with 5-hydroxy-6-methoxy-1,2,3,4-tetrahydroisoquinoline hydrochloride gave compound 37 (15% yield) as off-white oil. ¹H NMR (300 MHz, DMSO-d₆) δ 2.62 and 2.91 (2t, 2H), 3.50 and 4.04 (2t, 2H), 3.74 and 3.80 (2s, 3H), 4.40 and 4.93 (2s, 2H), 6.31 and 6.77 (2d, 1H), 6.71 and 6.91 (2d, 1H), 7.26-7.84 (m, 1H), 7.90-8.02 (m, 3H), 8.11-8.24 (m, 2H), 8.68-8.76 (m, 3H); MS (ESI) m/z 480 ([M+H]⁺).

Preparation of 2-[[2-(4-(trifluoromethyl)phenyl)quinazolin-4-yl]carbonyl]-5,6-dihydroxy-1,2,3,4-tetrahydroisoquinoline (compound 38)

2-[[2-(4-(trifluoromethyl)phenyl)quinazolin-4-yl]carbonyl]-5,6-dihydroxy-1,2,3,4-tetrahydroisoquinoline was obtained from compound 37 (41% yield, light yellow solid) by the same way with the preparation of compound 2. ¹H NMR (300 MHz, CDCl₃) δ 2.83 and 3.07 (2t, 2H), 3.57 and 4.21 (2t, 2H), 4.44 and 5.06 (2s, 2H), 5.43 (b, 1H), 6.23 and 7.01 (2d, 1H), 6.20 and 6.81 (2d, 1H), 7.60-7.71 (m, 1H), 7.77-7.82 (m, 2H), 7.94-8.07 (m, 2H), 8.20-8.23 (m, 1H), 8.73-8.80 (m, 2H); MS (ESI) m/z 466 ([M+H]⁺).

Preparation of 2-[[2-(4-(trifluoromethyl)phenyl)quinazolin-4-yl]carbonyl]-5,6-dimethoxy-1,2,3,4-tetrahydroisoquinoline (compound 39)

Reaction of 2-(4-(trifluoromethyl)phenyl)quinazoline-4-carboxylic acid with 5,6-dimethoxy-1,2,3,4-tetrahydroisoquinoline hydrochloride gave compound 39 (13% yield) as a white solid. ¹H NMR (300 MHz, DMSO-d₆) δ 2.72 and 2.99 (2t, 2H), 3.50 and 4.04 (2t, 2H), 3.68-3.82 (4s, 6H), 4.43 and 4.94 (2s, 2H), 6.62 and 7.01 (2d, 1H), 6.81 and 7.08 (2d, 1H), 7.82-7.85 (m, 1H), 7.93-8.04 (m, 3H), 8.12-8.24 (m, 2H), 8.70-8.76 (m, 2H); MS (ESI) m/z 494 ([M+H]⁺).

Preparation of 2-[[2-(4-(trifluoromethyl)phenyl)quinazolin-4-yl]carbonyl]-5-hydroxy-6-dimethylamino-1,2,3,4-tetrahydroisoquinoline (compound 40)

Reaction of 2-(4-(trifluoromethyl)phenyl)quinazoline-4-carboxylic acid with 5-hydroxy-6-dimethylamino-1,2,3,4-tetrahydroisoquinoline hydrochloride gave compound 40 (15% yield) as a brown solid. ¹H NMR (300 MHz, CDCl₃) δ 2.56 and 2.70 (2s, 6H), 2.85 and 3.10 (2t, 2H), 3.58 and 4.22 (2t, 2H), 4.48 and 5.10 (2s, 2H), 6.33 and 6.83 (2d, 1H), 6.97 and 7.16 (2d, 1H), 7.62-8.55 (m, 7H), 8.74-8.80 (m, 2H); MS (ESI) m/z 493 ([M+H]⁺).

Preparation of 2-[[2-(4-(trifluoromethyl)phenyl)quinazolin-4-yl]carbonyl]-5-hydroxy-6-methyl-1,2,3,4-tetrahydroisoquinoline (compound 41)

Reaction of 2-(4-(trifluoromethyl)phenyl)quinazoline-4-carboxylic acid with 5-hydroxy-6-methyl-1,2,3,4-tetrahydroisoquinoline hydrochloride gave compound 41 (21% yield) as a white solid. ¹H NMR (300 MHz, DMSO-d₆) δ 2.13 and 2.17 (2s, 3H), 2.65 and 2.93 (2t, 2H), 3.51 and 4.06 (2t, 2H), 4.42 and 4.94 (2s, 2H), 6.29 and 6.75 (2d, 1H), 6.80 and 7.00 (2dm, 1H), 7.75-7.85 (m, 1H), 7.91-8.03 (m, 3H), 8.11-8.24 (m, 2H), 8.36 and 8.45 (2s, 1H), 8.69-8.74 (m, 2H); MS (ESI) m/z 464 ([M+H]⁺).

Preparation of 2-[[2-(3-fluorophenyl)quinazolin-4-yl]carbonyl]-5-hydroxy-6-methoxy-1,2,3,4-tetrahydroisoquinoline (compound 42)

Reaction of 2-(3-fluorophenyl)quinazoline-4-carboxylic acid with 5-hydroxy-6-methoxy-1,2,3,4-tetrahydroisoquinoline hydrochloride gave compound 42 (24% yield) as a white solid. ¹H NMR (300 MHz, DMSO-d₆) δ 2.63 and 2.90 (2t, 2H), 3.50 and 4.04 (2t, 2H), 3.74 and 3.80 (2s, 3H), 4.40 and 4.92 (2s, 2H), 6.32 and 6.77 (2d, 1H), 6.71 and 6.91 (2d, 1H), 7.44-7.46 (m, 1H), 7.61-7.82 (m, 2H), 7.89-8.00 (2d, 1H), 8.08-8.26 (m, 3H), 8.31-8.41 (m, 1H); 8.68-8.72 (2s, 1H); MS (ESI) m/z 430 ([M+H]⁺).

Preparation of 2-[[2-(3-fluorophenyl)quinazolin-4-yl]carbonyl]-5,6-dihydroxy-1,2,3,4-tetrahydroisoquinoline (compound 43)

2-[[2-(3-fluorophenyl)quinazolin-4-yl]carbonyl]-5,6-dihydroxy-1,2,3,4-tetrahydroisoquinoline was obtained from compound 42 (4% yield, light yellow solid) by the same way with the preparation of compound 2. ¹H NMR (300 MHz, CD₃OD) δ 2.79 and 3.06 (2t, 2H), 3.55 and 4.15 (2t, 2H), 4.40 and 4.99 (2s, 2H), 6.15 and 6.66 (2d, 1H), 6.55 and 6.76 (2d, 1H), 7.26-7.29 (m, 1H), 7.54-7.58 (m, 1H), 7.66-7.77 (m, 1H), 7.89-8.09 (m, 2H), 8.15-8.20 (t, 1H), 8.29-8.46 (m, 2H); MS (ESI) m/z 416 ([M+H]⁺).

Preparation of 2-[[2-(3-fluorophenyl)quinazolin-4-yl]carbonyl]-5,6-dimethoxy-1,2,3,4-tetrahydroisoquinoline (compound 44)

Reaction of 2-(3-fluorophenyl)quinazoline-4-carboxylic acid with 5,6-dimethoxy-1,2,3,4-tetrahydroisoquinoline hydrochloride gave compound 44 (11% yield) as a white solid. ¹H NMR (300 MHz, CDCl₃) δ 2.90 and 3.13 (2t, 2H), 3.56 and 4.17 (2t, 2H), 3.83-3.91 (4s, 6H), 4.47 and 5.07 (2s, 2H), 6.52 and 6.91 (2d, 1H), 6.72 and 7.02 (2d, 1H), 7.22-7.23 (m, 1H), 7.49-7.65 (m, 2H), 7.94-8.18 (m, 3H), 8.33-8.47 (m, 2H); MS (ESI) m/z 444 ([M+H]⁺).

Preparation of 2-[[2-(3-fluorophenyl)quinazolin-4-yl]carbonyl]-5-hydroxy-6-dimethylamino-1,2,3,4-tetrahydroisoquinoline (compound 45)

Reaction of 2-(3-fluorophenyl)quinazoline-4-carboxylic acid with 5-hydroxy-6-dimethylamino-1,2,3,4-tetrahydroisoquinoline hydrochloride gave compound 45 (11% yield) as a brown solid. ¹H NMR (300 MHz, CDCl₃) δ 2.66 and 3.15 (2d, 6H), 2.85 and 3.07 (2t, 2H), 3.58 and 4.21 (2t, 2H), 4.49 and 5.09 (2s, 2H), 6.34 and 6.82 (2d, 1H), 6.97 and 7.15 (2d, 1H), 7.19-8.06 (m, 6H), 8.13-8.18 (m, 1H), 8.34-8.47 (m, 2H); MS (ESI) m/z 443 ([M+H]⁺).

Preparation of 2-[[2-(3-fluorophenyl)phenyl)quinazolin-4-yl]carbonyl]-5-hydroxy-6-methyl-1,2,3,4-tetrahydroisoquinoline (compound 46)

Reaction of 2-(3-fluorophenyl)quinazoline-4-carboxylic acid with 5-hydroxy-6-methyl-1,2,3,4-tetrahydroisoquinoline hydrochloride gave compound 46 (6% yield) as a white solid. ¹H NMR (300 MHz, CDCl₃) δ 2.13 and 2.17 (2s, 3H), 2.65 and 2.93 (2t, 2H), 3.51 and 4.05 (2t, 2H), 4.42 and 4.93 (2s, 2H), 6.29 and 6.75 (2d, 1H), 6.80 and 7.00 (2d, 1H), 7.42-7.45 (m, 1H), 7.61-7.82 (m, 2H), 7.89-8.01 (2d, 1H), 8.12 and 8.44 (m, 5H); MS (ESI) m/z 414 ([M+H]⁺).

Preparation of 2-[[2-(3-methoxylphenyl)quinazolin-4-yl]carbonyl]-5-hydroxy-6-methoxy-1,2,3,4-tetrahydroisoquinoline (compound 47)

Reaction of 2-(3-methoxylphenyl)quinazoline-4-carboxylic acid with 5-hydroxy-6-methoxy-1,2,3,4-tetrahydroisoquinoline hydrochloride gave compound 47 (17% yield) as a white solid. ¹H NMR (300 MHz, DMSO-d₆) δ 2.67 and 2.90 (2t, 2H), 3.50 and 4.04 (2t, 2H), 3.74-3.88 (4s, 6H), 4.39 and 4.92 (2s, 2H), 6.32 and 6.77 (2d, 1H), 6.70 and 6.91 (2d, 1H), 7.15-7.18 (m, 1H), 7.46-7.53 (m, 1H), 7.77-8.19 (m, 6H), 8.68-8.72 (2s, 1H); MS (ESI) m/z 442 ([M+H]⁺).

Preparation of 2-[[2-(3-methoxylphenyl)quinazolin-4-yl]carbonyl]-5,6-dihydroxy-1,2,3,4-tetrahydroisoquinoline (compound 48)

Reaction of 2-(3-methoxylphenyl)quinazoline-4-carboxylic acid with 5,6-dihydroxy-1,2,3,4-tetrahydroisoquinoline hydrobromide gave compound 48 (9% yield) as brown oil. ¹H NMR (300 MHz, CD₃OD) δ 2.83 and 3.05 (2t, 2H), 3.55 and 4.14 (2t, 2H), 3.87-3.92 (2s, 3H), 4.40 and 4.98 (2s, 2H), 6.15 and 6.64 (2d, 1H), 6.54 and 6.75 (2d, 1H), 7.08-7.12 (m, 1H), 7.41-7.47 (m, 1H), 7.69-7.74 (m, 1H), 7.88-8.21 (m, 5H); MS (ESI) m/z 428 ([M+H]⁺).

Preparation of 2-[[2-(3-methoxylphenyl)quinazolin-4-yl]carbonyl]-5,6-dimethoxy-1,2,3,4-tetrahydroisoquinoline (compound 49)

Reaction of 2-(3-methoxylphenyl)quinazoline-4-carboxylic acid with 5,6-dimethoxy-1,2,3,4-tetrahydroisoquinoline hydrochloride gave compound 49 (11% yield) as a white solid. ¹H NMR (300 MHz, CDCl₃) δ 2.92 and 3.15 (2t, 2H), 3.57 and 4.17 (2t, 2H), 3.82-3.98 (m, 9H), 4.47 and 5.07 (2s, 2H), 6.53 and 6.91 (2d, 1H), 6.72 and 7.02 (2d, 1H), 7.11-7.14 (m, 1H), 7.44-7.50 (t, 1H), 7.63-7.69 (m, 1H), 7.98-8.09 (m, 2H), 8.29-8.38 (m, 3H); MS (ESI) m/z 456 ([M+H]⁺).

Preparation of 2-[[2-(3-methoxylphenyl)quinazolin-4-yl]carbonyl]-5-hydroxy-6-dimethylamino-1,2,3,4-tetrahydroisoquinoline (compound 50)

Reaction of 2-(3-methoxylphenyl)quinazoline-4-carboxylic acid with 5-hydroxy-6-dimethylamino-1,2,3,4-tetrahydroisoquinoline hydrochloride gave compound 50 (10% yield) as a brown solid. ¹H NMR (300 MHz, CDCl₃) δ 2.64 and 2.68 (2s, 6H), 2.87 and 3.09 (2t, 2H), 3.60 and 4.21 (2t, 2H), 3.94 and 3.97 (2s, 3H), 4.50 and 5.09 (2s, 2H), 6.34 and 6.82 (2d, 1H), 6.95-7.16 (m, 2H), 7.42-7.49 (m, 1H), 7.55-7.65 (m, 1H), 7.90-8.06 (m, 2H), 8.13-8.29 (m, 3H); MS (ESI) m/z 455 ([M+H]⁺).

Preparation of 2-[[2-(3-methoxylphenyl)phenyl)quinazolin-4-yl]carbonyl]-5-hydroxy-6-methyl-1,2,3,4-tetrahydroisoquinoline (compound 51)

Reaction of 2-(3-methoxylphenyl)quinazoline-4-carboxylic acid with 5-hydroxy-6-methyl-1,2,3,4-tetrahydroisoquinoline hydrochloride gave compound 51 (31% yield) as a light yellow solid. ¹H NMR (300 MHz, CDCl₃) δ 2.25 and 2.28 (2s, 3H), 2.83 and 3.05 (2t, 2H), 3.62 and 4.23 (2t, 2H), 3.96 and 3.99 (2s, 3H), 4.50 and 5.10 (2s, 2H), 6.36 and 6.82 (2d, 1H), 6.91 and 7.08 (2d, 1H), 7.12-7.15 (m, 1H), 7.47-7.51 (m, 1H), 7.61-7.70 (m, 1H), 8.01-8.11 (m, 2H), 8.27-8.31 (m, 2H), 8.41-8.45 (m, 1H); MS (ESI) m/z 426 ([M+H]⁺).

Preparation of 2-[[2-(3-(trifluoromethyl)phenyl)quinazolin-4-yl]carbonyl]-5-hydroxy-6-methoxy-1,2,3,4-tetrahydroisoquinoline (compound 52)

Reaction of 2-(3-(trifluoromethyl)phenyl)quinazoline-4-carboxylic acid with 5-hydroxy-6-methoxy-1,2,3,4-tetrahydroisoquinoline hydrochloride gave compound 52 (18% yield) as a white solid. ¹H NMR (300 MHz, DMSO-d₆) δ 2.63 and 2.91 (2t, 2H), 3.51 and 4.04 (2t, 2H), 3.74 and 3.80 (2s, 3H), 4.40 and 4.93 (2s, 2H), 6.31 and 6.77 (2d, 1H), 6.70 and 6.91 (2d, 1H), 7.74-8.01 (m, 4H), 8.10-8.16 (m, 1H), 8.20-8.26 (m, 1H), 8.67 and 8.72 (2s, 1H), 8.73-8.85 (m, 2H); MS (ESI) m/z 480 ([M+H]⁺).

Preparation of 2-[[2-(3-(trifluoromethyl)phenyl)quinazolin-4-yl]carbonyl]-5,6-dihydroxy-1,2,3,4-tetrahydroisoquinoline (compound 53)

2-[[2-(3-(trifluoromethyl)phenyl)quinazolin-4-yl]carbonyl]-5,6-dihydroxy-1,2,3,4-tetrahydroisoquinoline was obtained from compound 52 (17% yield, white solid) by the same way with the preparation of compound 2. $^1$H NMR (300 MHz, CDCl$_3$) δ 2.83 and 3.07 (2t, 2H), 3.58 and 4.21 (2t, 2H), 4.43 and 5.06 (2s, 2H), 6.23 and 6.71 (2d, 1H), 6.62 and 6.81 (2d, 1H), 7.61-7.70 (m, 2H), 7.78-7.80 (m, 1H), 7.94-8.06 (m, 2H), 8.18-8.22 (m, 1H), 8.81-8.96 (m, 2H); MS (ESI) m/z 466 ([M+H]$^+$).

Preparation of 2-[[2-(3-(trifluoromethyl)phenyl)quinazolin-4-yl]carbonyl]-5,6-dimethoxy-1,2,3,4-tetrahydroisoquinoline (compound 54)

Reaction of 2-(3-(trifluoromethyl)phenyl)quinazoline-4-carboxylic acid with 5,6-dimethoxy-1,2,3,4-tetrahydroisoquinoline hydrochloride gave compound 54 (12% yield) as a white solid. $^1$H NMR (300 MHz, DMSO-d$_6$) δ 2.74 and 2.99 (2t, 2H), 3.52 and 4.04 (2t, 2H), 3.68-3.82 (4s, 6H), 4.43 and 4.95 (2s, 2H), 6.62 and 7.01 (2d, 1H), 6.80 and 7.08 (2d, 1H), 7.75-7.88 (m, 2H), 7.93-8.04 (m, 2H), 8.11-8.17 (m, 1H), 8.21-8.26 (m, 1H), 8.74-8.85 (m, 2H); MS (ESI) m/z 494 ([M+H]$^+$).

Preparation of 2-[[2-(3-(trifluoromethyl)phenyl)quinazolin-4-yl]carbonyl]-5-hydroxy-6-dimethylamino-1,2,3,4-tetrahydroisoquinoline (compound 55)

Reaction of 2-(3-(trifluoromethyl)phenyl)quinazoline-4-carboxylic acid with 5-hydroxy-6-dimethylamino-1,2,3,4-tetrahydroisoquinoline hydrochloride gave compound 55 (5% yield) as a brown solid. $^1$H NMR (300 MHz, CDCl$_3$) δ 2.71 and 2.77 (2s, 6H), 2.85 and 3.11 (2t, 2H), 3.59 and 4.22 (2t, 2H), 4.49 and 5.11 (2s, 2H), 6.36 and 6.86 (2d, 1H), 6.99-7.17 (m, 2H), 7.62-7.70 (m, 2H), 7.77-7.80 (m, 1H), 7.96-8.07 (m, 2H), 8.16-8.21 (m, 1H), 8.82-8.96 (m, 2H); MS (ESI) m/z 493 ([M+H]$^+$).

Preparation of 2-[[2-(3-(trifluoromethyl)phenyl)quinazolin-4-yl]carbonyl]-5-hydroxy-6-methyl-1,2,3,4-tetrahydroisoquinoline (compound 56)

Reaction of 2-(3-(trifluoromethyl)phenyl)quinazoline-4-carboxylic acid with 5-hydroxy-6-methyl-1,2,3,4-tetrahydroisoquinoline hydrochloride gave compound 56 (14% yield) as a white solid. $^1$H NMR (300 MHz, CDCl$_3$) δ 2.25 and 2.28 (2s, 3H), 2.82 and 3.06 (2t, 2H), 3.61 and 4.25 (2t, 2H), 4.48 and 5.11 (2s, 2H), 6.34 and 6.83 (2d, 1H), 6.90 and 7.09 (2d, 1H), 7.63-7.71 (m, 2H), 7.79-7.81 (m, 1H), 7.98-8.09 (m, 2H), 8.25-8.30 (m, 1H), 8.88-8.97 (m, 2H); MS (ESI) m/z 464 ([M+H]$^+$).

Preparation of 2-[[2-(2,4-difluorophenyl)quinazolin-4-yl]carbonyl]-5-hydroxy-6-methoxy-1,2,3,4-tetrahydroisoquinoline (compound 57)

Reaction of 2-(2,4-difluorophenyl)quinazoline-4-carboxylic acid with 5-hydroxy-6-methoxy-1,2,3,4-tetrahydroisoquinoline hydrochloride gave compound 57 (11% yield) as a white solid. $^1$H NMR (300 MHz, CDCl$_3$) δ 2.62 and 2.88 (2t, 2H), 3.49 and 4.01 (2t, 2H), 3.74 and 3.79 (2s, 3H), 4.39 and 4.90 (2s, 2H), 6.34 and 6.76 (2d, 1H), 6.72 and 6.90 (2d, 1H), 7.27-7.31 (m, 1H), 7.42-7.46 (m, 1H), 7.82-7.84 (m, 1H), 7.89 and 7.99 (2s, 1H), 8.09-8.26 (m, 3H), 8.68 and 8.73 (2s, 1H); MS (ESI) m/z 448 ([M+H]$^+$).

Preparation of 2-[[2-(2,4-difluorophenyl)quinazolin-4-yl]carbonyl]-5,6-dihydroxy-1,2,3,4-tetrahydroisoquinoline (compound 58)

2-[[2-(2,4-difluorophenyl)quinazolin-4-yl]carbonyl]-5,6-dihydroxy-1,2,3,4-tetrahydroisoquinoline was obtained from compound 57 (20% yield, light yellow solid) by the same way with the preparation of compound 2. $^1$H NMR (300 MHz, CDCl$_3$) δ 2.83 and 3.04 (2t, 2H), 3.61 and 4.18 (2t, 2H), 4.48 and 5.02 (2s, 2H), 6.28 and 6.69 (2d, 1H), 6.64 and 6.79 (2d, 1H), 6.97-7.09 (m, 2H), 7.66-7.74 (m, 1H), 7.99-8.10 (m, 2H), 8.18-8.29 (m, 2H); MS (ESI) m/z 434 ([M+H]$^+$).

Preparation of 2-[[2-(2,4-difluorophenyl)quinazolin-4-yl]carbonyl]-5,6-dimethoxy-1,2,3,4-tetrahydroisoquinoline (compound 59)

Reaction of 2-(2,4-difluorophenyl)quinazoline-4-carboxylic acid with 5,6-dimethoxy-1,2,3,4-tetrahydroisoquinoline hydrochloride gave compound 59 (12% yield) as a white solid. $^1$H NMR (300 MHz, DMSO-d$_6$) δ 2.72 and 2.97 (2t, 2H), 3.50 and 4.01 (2t, 2H), 3.68-3.81 (m, 6H), 4.42 and 4.92 (2s, 2H), 6.64 and 7.00 (2d, 1H), 6.82 and 7.07 (2d, 1H), 7.28-7.49 (m, 2H), 7.75-7.84 (m, 1H), 7.93-8.10 (m, 1H), 8.13-8.26 (m, 3H); MS (ESI) m/z 462 ([M+H]$^+$).

Preparation of 2-[[2-(2,4-difluorophenyl)quinazolin-4-yl]carbonyl]-5-hydroxy-6-dimethylamino-1,2,3,4-tetrahydroisoquinoline (compound 60)

Reaction of 2-(2,4-difluorophenyl)quinazoline-4-carboxylic acid with 5-hydroxy-6-dimethylamino-1,2,3,4-tetrahydroisoquinoline hydrochloride gave compound 60 (8% yield) as a brown solid. $^1$H NMR (300 MHz, CDCl$_3$) δ 2.64 and 2.70 (2s, 6H), 2.85 and 3.08 (2t, 2H), 3.62 and 4.19 (2t, 2H), 4.53 and 5.07 (2s, 2H), 6.38 and 6.81 (2d, 1H), 6.96-7.15 (m, 3H), 7.63-7.70 (m, 1H), 7.96-8.09 (m, 2H), 8.14-8.26 (m, 2H); MS (ESI) m/z 461 ([M+H]$^+$).

Preparation of 2-[[2-(2,4-difluorophenyl)quinazolin-4-yl]carbonyl]-5-hydroxy-6-methyl-1,2,3,4-tetrahydroisoquinoline (compound 61)

Reaction of 2-(2,4-difluorophenyl)quinazoline-4-carboxylic acid with 5-hydroxy-6-methyl-1,2,3,4-tetrahydroisoquinoline hydrochloride gave compound 61 (22% yield) as a white solid. $^1$H NMR (300 MHz, CDCl$_3$) δ 2.25 and 2.28 (2s, 3H), 2.82 and 3.04 (2t, 2H), 3.65 and 4.21 (2t, 2H), 4.54 and 5.08 (2s, 2H), 6.39 and 6.81 (2d, 1H), 6.90-7.08 (m, 3H), 7.63-7.73 (m, 1H), 7.99-8.11 (m, 2H), 8.22-8.28 (m, 2H); MS (ESI) m/z 432 ([M+H]$^+$).

Preparation of 2-[[2-(4-acetamidophenyl)quinazolin-4-yl]carbonyl]-5-hydroxy-6-methoxy-1,2,3,4-tetrahydroisoquinoline (compound 62)

Reaction of 2-(4-acetamidophenyl)quinazoline-4-carboxylic acid with 5-hydroxy-6-methoxy-1,2,3,4-tetrahydroisoquinoline hydrochloride gave compound 62 (9% yield) as a white solid. $^1$H NMR (300 MHz, DMSO-d$_6$) δ 2.10 (s, 3H), 2.63 and 2.89 (2t, 2H), 3.47 and 4.03 (2t, 2H), 3.74 and 3.80 (2s, 3H), 4.38 and 4.91 (2s, 2H), 6.32 and 6.77 (2d, 1H), 6.70 and 6.91 (2d, 1H), 7.64-7.93 (m, 4H), 8.03-8.13 (m, 2H), 8.41-8.49 (m, 2H), 8.69 and 8.74 (2s, 1H), 10.23 (s, 1H); MS (ESI) m/z 469 ([M+H]$^+$).

Preparation of 2-[[2-(4-acetamidophenyl)quinazolin-4-yl]carbonyl]-5,6-dimethoxy-1,2,3,4-tetrahydroisoquinoline (compound 63)

Reaction of 2-(4-acetamidophenyl)quinazoline-4-carboxylic acid with 5,6-dimethoxy-1,2,3,4-tetrahydroisoquinoline hydrochloride gave compound 63 (7% yield) as a yellow solid. $^1$H NMR (300 MHz, DMSO-d$_6$) δ 2.09 (s, 3H), 2.73 and 2.98 (2t, 2H), 3.49 and 4.02 (2t, 2H), 3.68-3.81 (4s, 6H), 4.41 and 4.93 (2s, 2H), 6.63 and 7.01 (2d, 1H), 6.80 and 7.08 (2d, 1H), 7.65-7.80 (m, 3H), 7.84-7.95 (2d, 1H), 8.03-8.13 (m, 2H), 8.41-8.49 (m, 2H), 10.23 (s, 1H); MS (ESI) m/z 483 ([M+H]$^+$).

Preparation of 2-[[2-(4-acetamidophenyl)quinazolin-4-yl]carbonyl]-5-hydroxy-6-methyl-1,2,3,4-tetrahydroisoquinoline (compound 64)

Reaction of 2-(4-acetamidophenyl)quinazoline-4-carboxylic acid with 5-hydroxy-6-methyl-1,2,3,4-tetrahydroisoquinoline hydrochloride gave compound 64 (8% yield) as a yellow solid. $^1$H NMR (300 MHz, DMSO-d$_6$) δ 2.09-2.17 (m, 6H), 2.66 and 2.92 (2t, 2H), 3.49 and 4.06 (2t, 2H), 4.40 and 4.93 (2s, 2H), 6.30 and 6.74 (2d, 1H), 6.79 and 7.00 (2d, 1H), 7.64-7.95 (m, 4H), 8.02-8.13 (m, 2H), 8.39-8.50 (m, 3H), 10.22-10.24 (m, 1H); MS (ESI) m/z 453 ([M+H]$^+$).

Preparation of 2-[[2-(4-(acetamidomethyl)phenyl)quinazolin-4-yl]carbonyl]-5-hydroxy-6-methoxy-1,2,3,4-tetrahydroisoquinoline (compound 65)

Reaction of 2-(4-(acetamidomethyl)phenyl)quinazoline-4-carboxylic acid with 5-hydroxy-6-methoxy-1,2,3,4-tetrahydroisoquinoline hydrochloride gave compound 65 (15% yield) as a white solid. $^1$H NMR (300 MHz, DMSO-d$_6$) δ 1.91 (s, 3H), 2.63 and 2.90 (2t, 2H), 3.48 and 4.03 (2t, 2H), 3.74 and 3.80 (2s, 3H), 4.34-4.37 (m, 2H), 4.38 and 4.92 (2s, 2H), 6.31 and 6.77 (2d, 1H), 6.70 and 6.91 (2d, 1H), 7.42-7.47 (m, 2H), 7.67-7.77 (m, 1H), 7.85-7.97 (2d, 1H), 8.02-8.17 (m, 2H), 8.42-8.50 (m, 3H), 8.68 and 8.73 (2s, 1H); MS (ESI) m/z 483 ([M+H]$^+$).

Preparation of 2-[[2-(4-(acetamidomethyl)phenyl)quinazolin-4-yl]carbonyl]-5,6-dihydroxy-1,2,3,4-tetrahydroisoquinoline (compound 66)

2-[[2-(4-(acetamidomethyl)phenyl)quinazolin-4-yl]carbonyl]-5,6-dihydroxy-1,2,3,4-tetrahydroisoquinoline was obtained from compound 65 (10% yield, gray solid) by the same way with the preparation of compound 2. $^1$H NMR (300 MHz, DMSO-d$_6$) δ 1.91 (s, 3H), 2.64 and 2.89 (2t, 2H), 3.46 and 4.02 (2t, 2H), 4.34-4.35 (m, 2H), 4.37 and 4.87 (2s, 2H), 6.16 and 6.62 (2d, 1H), 6.50 and 6.72 (2d, 1H), 7.42-7.47 (m, 2H), 7.68-8.23 (m, 5H), 8.38-8.51 (m, 3H), 9.10-9.20 (m, 1H); MS (ESI) m/z 469 ([M+H]$^+$).

Preparation of 2-[[2-(4-(acetamidomethyl)phenyl)quinazolin-4-yl]carbonyl]-5,6-dimethoxy-1,2,3,4-tetrahydroisoquinoline (compound 67)

Reaction of 2-(4-(acetamidomethyl)phenyl)quinazoline-4-carboxylic acid with 5,6-dimethoxy-1,2,3,4-tetrahydroisoquinoline hydrochloride gave compound 67 (5% yield) as a white solid. $^1$H NMR (300 MHz, DMSO-d$_6$) δ 1.91 (s, 3H), 2.73 and 2.98 (2t, 2H), 3.48 and 4.03 (2t, 2H), 3.69-3.82 (4s, 6H), 4.34-4.36 (m, 2H), 4.41 and 4.93 (2s, 2H), 6.62 and 7.01 (2d, 1H), 6.80 and 7.08 (2d, 1H), 7.42-7.47 (m, 2H), 7.75-8.17 (m, 4H), 8.44-8.51 (m, 3H); MS (ESI) m/z 497 ([M+H]$^+$).

Preparation of 2-[[2-(4-(acetamidomethyl)phenyl)quinazolin-4-yl]carbonyl]-5-hydroxy-6-dimethylamino-1,2,3,4-tetrahydroisoquinoline (compound 68)

Reaction of 2-(4-(acetamidomethyl)phenyl)quinazoline-4-carboxylic acid with 5-hydroxy-6-dimethylamino-1,2,3,4-tetrahydroisoquinoline hydrochloride gave compound 68 (5% yield) as a white solid. $^1$H NMR (300 MHz, DMSO-d$_6$) δ 1.91 (s, 3H), 2.56 and 2.60 (2s, 6H), 2.63 and 2.90 (2t, 2H), 3.48 and 4.04 (2t, 2H), 4.34-4.37 (m, 2H), 4.39 and 4.92 (2s, 2H), 6.31-7.02 (m, 2H), 7.41-7.47 (m, 2H), 7.66-7.78 (m, 1H), 7.88-7.98 (m, 1H), 8.02-8.17 (m, 2H), 8.43-8.51 (m, 3H); MS (ESI) m/z 496 ([M+H]$^+$).

Preparation of 2-[[2-(4-(acetamidomethyl)phenyl)quinazolin-4-yl]carbonyl]-5-hydroxy-6-methyl-1,2,3,4-tetrahydroisoquinoline (compound 69)

Reaction of 2-(4-(acetamidomethyl)phenyl)quinazoline-4-carboxylic acid with 5-hydroxy-6-methyl-1,2,3,4-tetrahydroisoquinoline hydrochloride gave compound 69 (13% yield) as a white solid. $^1$H NMR (300 MHz, DMSO-d$_6$) δ 1.91 (s, 3H), 2.13 and 2.17 (2s, 3H), 2.66 and 2.92 (2t, 2H), 3.49 and 4.05 (2t, 2H), 4.35-4.37 (m, 2H), 4.40 and 4.93 (2s, 2H), 6.29 and 6.74 (2d, 1H), 6.79 and 7.00 (2d, 1H), 7.42-7.47 (m, 2H), 7.68-8.11 (m, 5H), 8.43-8.46 (m, 3H); MS (ESI) m/z 467 ([M+H]$^+$).

Preparation of 2-[[2-(4-pyrimidinyl)quinazolin-4-yl]carbonyl]-5-hydroxy-6-methoxy-1,2,3,4-tetrahydroisoquinoline (compound 70)

Reaction of 2-(4-pyrimidinyl)quinazoline-4-carboxylic acid with 5-hydroxy-6-methoxy-1,2,3,4-tetrahydroisoquinoline hydrochloride gave compound 70 (13% yield) as a light brown solid. $^1$H NMR (300 MHz, DMSO-d$_6$) δ 2.61 and 2.90 (2t, 2H), 3.49 and 4.04 (2t, 2H), 3.73 and 3.80 (2s, 3H), 4.38 and 4.92 (2s, 2H), 6.30 and 6.77 (2d, 1H), 6.70 and 6.91 (2d, 1H), 7.90-8.31 (m, 4H), 8.48-8.54 (m, 1H), 8.68-8.74 (2s, 1H), 9.06-9.43 (m, 1H), 9.44 (s, 1H); MS (ESI) m/z 414 ([M+H]$^+$).

Preparation of 2-[[2-(4-pyrimidinyl)quinazolin-4-yl]carbonyl]-5,6-dihydroxy-1,2,3,4-tetrahydroisoquinoline (compound 71)

2-[[2-(4-pyrimidinyl)quinazolin-4-yl]carbonyl]-5,6-dihydroxy-1,2,3,4-tetrahydroisoquinoline was obtained from compound 70 (12% yield, light yellow solid) by the same way with the preparation of compound 2. $^1$H NMR (300 MHz, CD$_3$OD) δ 2.80 and 3.08 (2t, 2H), 3.55 and 4.16 (2t, 2H), 4.39 and 4.99 (2s, 2H), 6.15 and 6.67 (2d, 1H), 6.54 and 6.76 (2d, 1H), 7.83-8.03 (m, 2H), 8.12-8.22 (m, 2H), 8.33-8.38 (m, 1H), 8.65-8.75 (m, 1H), 9.05-9.10 (m, 1H), 9.42 (m, 1H); MS (ESI) m/z 400 ([M+H]$^+$).

Preparation of 2-[[2-(4-pyrimidinyl)quinazolin-4-yl]carbonyl]-5,6-dimethoxy-1,2,3,4-tetrahydroisoquinoline (compound 72)

Reaction of 2-(4-pyrimidinyl)quinazoline-4-carboxylic acid with 5,6-dimethoxy-1,2,3,4-tetrahydroisoquinoline hydrochloride gave compound 72 (17% yield) as a brown solid. $^1$H NMR (300 MHz, CDCl$_3$) δ 2.86 and 3.13 (2t, 2H), 3.54 and 4.17 (2t, 2H), 3.81-3.90 (m, 6H), 4.43 and 5.06 (2s, 2H), 6.51 and 6.91 (2d, 1H), 6.71 and 7.01 (2d, 1H), 7.74-7.81 (m, 2H), 8.04-8.13 (m, 2H), 8.39-8.41 (2s, 1H), 8.65-8.70 (m, 1H), 9.04-9.06 (m, 1H), 9.57 (s, 1H); MS (ESI) m/z 428 ([M+H]$^+$).

Preparation of 2-[[2-(4-pyrimidinyl)quinazolin-4-yl]carbonyl]-5-hydroxy-6-methyl-1,2,3,4-tetrahydroisoquinoline (compound 73)

Reaction of 2-(4-pyrimidinyl)quinazoline-4-carboxylic acid with 5-hydroxy-6-methyl-1,2,3,4-tetrahydroisoquinoline hydrochloride gave compound 73 (15% yield) as a white solid. $^1$H NMR (300 MHz, CDCl$_3$) δ 2.25-2.28 (m, 3H), 2.78 and 3.05 (2t, 2H), 3.56 and 4.21 (2t, 2H), 4.46 and 5.09 (2s, 2H), 6.30-7.07 (m, 2H), 7.74-7.82 (m, 1H), 8.04-8.12 (m, 2H), 8.35-8.42 (m, 1H), 8.65-8.75 (m, 1H), 9.02-9.10 (m, 1H), 9.55-9.60 (m, 1H); MS (ESI) m/z 398 ([M+H]$^+$).

Preparation of 2-[[2-(2-(acetamido)ethyl)quinazolin-4-yl]carbonyl]-5-hydroxy-6-methoxy-1,2,3,4-tetrahydroisoquinoline (compound 74)

Reaction of 2-(2-(acetamido)ethyl)quinazoline-4-carboxylic acid with 5-hydroxy-6-methoxy-1,2,3,4-tetrahydroisoquinoline hydrochloride gave compound 74 (30% yield) as a light yellow solid. $^1$H NMR (300 MHz, DMSO-d$_6$) δ 1.74 (d, 3H), 2.60 and 2.86 (2t, 2H), 3.16 (t, 2H), 3.44 and 3.98 (2t, 2H), 3.59 (t, 2H), 3.73 and 3.79 (2s, 3H), 4.33 and 4.87 (2s, 2H), 6.32-6.91 (m, 2H), 7.65-7.75 (m, 1H), 7.82-7.92 (m, 2H), 8.01-8.05 (m, 2H), 8.66-8.70 (m, 1H); MS (ESI) m/z 421 ([M+H]$^+$).

Preparation of 2-[[2-(2-(acetamido)ethyl)quinazolin-4-yl]carbonyl]-5,6-dihydroxy-1,2,3,4-tetrahydroisoquinoline (compound 75)

2-[[2-(2-(acetamido)ethyl)quinazolin-4-yl]carbonyl]-5,6-dihydroxy-1,2,3,4-tetrahydroisoquinoline was obtained from compound 74 (25% yield, brown solid) by the same way with the preparation of compound 2. $^1$H NMR (300 MHz, CD$_3$OD) δ 1.86-1.88 (m, 3H), 2.76 and 3.03 (2t, 2H), 3.26-3.29 (m, 2H), 3.52 and 4.11 (2t, 2H), 3.74-3.84 (m, 2H), 4.35 and 4.94 (2s, 2H), 6.18-6.75 (m, 2H), 7.23-7.89 (m, 2H), 7.98-8.07 (m, 3H); MS (ESI) m/z 407 ([M+H]$^+$).

Preparation of 2-[[2-(2-(acetamido)ethyl)quinazolin-4-yl]carbonyl]-5,6-dimethoxy-1,2,3,4-tetrahydroisoquinoline (compound 76)

Reaction of 2-(2-(acetamido)ethyl)quinazoline-4-carboxylic acid with 5,6-dimethoxy-1,2,3,4-tetrahydroisoquinoline hydrochloride gave compound 76 (17% yield) as a white solid. $^1$H NMR (300 MHz, DMSO-d$_6$) δ 1.74-1.75 (m, 3H), 2.69 and 2.95 (2t, 2H), 3.14-3.19 (m, 2H), 3.45 and 3.99 (2t, 2H), 3.57-3.61 (m, 2H), 3.74-3.80 (3s, 6H), 4.36 and 4.89 (2s, 2H), 6.64 and 6.99 (2d, 1H), 6.82 and 7.05 (2d, 1H), 7.67-7.75 (m, 1H), 7.85-7.94 (m, 2H), 8.02-8.06 (m, 2H); MS (ESI) m/z 435 ([M+H]$^+$).

Preparation of 2-[[2-(2-(acetamido)ethyl)quinazolin-4-yl]carbonyl]-5-hydroxy-6-dimethylamino-1,2,3,4-tetrahydroisoquinoline (compound 77)

Reaction of 2-(2-(acetamido)ethyl)quinazoline-4-carboxylic acid with 5-hydroxy-6-dimethylamino-1,2,3,4-tetrahydroisoquinoline hydrochloride gave compound 77 (9% yield) as brown oil. $^1$H NMR (300 MHz, CD$_3$OD) δ 1.86 and 1.88 (2s, 3H), 2.62 and 2.66 (2s, 6H), 2.79 and 3.03 (2t, 2H), 3.26-3.30 (m, 2H), 3.54 and 4.14 (2t, 2H), 3.73-3.82 (m, 2H), 4.41 and 4.99 (2s, 2H), 6.35 and 6.79 (2d, 1H), 6.91 and 7.10 (2d, 1H), 7.67-7.77 (m, 1H), 7.88-8.07 (m, 3H); MS (ESI) m/z 434 ([M+H]$^+$).

Preparation of 2-[[2-(2-(acetamido)ethyl)quinazolin-4-yl]carbonyl]-5-hydroxy-6-methyl-1,2,3,4-tetrahydroisoquinoline (compound 78)

Reaction of 2-(2-(acetamido)ethyl)quinazoline-4-carboxylic acid with 5-hydroxy-6-methyl-1,2,3,4-tetrahydroisoquinoline hydrochloride gave compound 78 (7% yield) as a white solid. $^1$H NMR (300 MHz, DMSO-d$_6$) δ 1.74 and 1.76 (2s, 3H), 2.12 and 2.16 (2s, 3H), 2.62 and 2.88 (2t, 2H), 3.12-3.20 (m, 2H), 3.48 and 4.00 (2t, 2H), 3.54-3.64 (m, 2H), 4.35 and 4.88 (2s, 2H), 6.31 and 6.72 (2d, 1H), 6.80 and 6.98 (2d, 1H), 7.72-7.92 (m, 3H), 8.01-8.06 (m, 2H), 8.34 and 8.42 (2s, 1H); MS (ESI) m/z 405 ([M+H]$^+$).

Preparation of 2-[[2-(4-thiazolyl)quinazolin-4-yl]carbonyl]-5-hydroxy-6-methoxy-1,2,3,4-tetrahydroisoquinoline (compound 79)

Reaction of 2-(4-thiazolyl)quinazoline-4-carboxylic acid with 5-hydroxy-6-methoxy-1,2,3,4-tetrahydroisoquinoline hydrochloride gave compound 79 (9% yield) as a white solid. $^1$H NMR (300 MHz, DMSO-d$_6$) δ 2.62 and 2.89 (2t, 2H), 3.47 and 4.02 (2t, 2H), 3.73 and 3.80 (2s, 3H), 4.37 and 4.91 (2s, 2H), 6.31 and 6.77 (2d, 1H), 6.70 and 6.91 (2d, 1H), 7.70-7.97 (m, 2H), 8.10-8.18 (m, 2H), 8.66-8.72 (m, 2H), 9.27-9.29 (m, 1H); MS (ESI) m/z 419 ([M+H]$^+$).

Preparation of 2-[[2-(4-thiazolyl)quinazolin-4-yl]carbonyl]-5,6-dihydroxy-1,2,3,4-tetrahydroisoquinoline (compound 80)

2-[[2-(4-thiazolyl)quinazolin-4-yl]carbonyl]-5,6-dihydroxy-1,2,3,4-tetrahydroisoquinoline was obtained from compound 79 (24% yield, light yellow solid) by the same way with the preparation of compound 2. $^1$H NMR (300 MHz, CDCl$_3$) δ 2.79 and 3.00 (2t, 2H), 3.51 and 4.16 (2t, 2H), 4.39 and 4.98 (2s, 2H), 6.19-6.88 (m, 2H), 7.63-7.71 (m, 1H), 7.94-8.05 (m, 2H), 8.28-8.31 (2s, 1H), 8.56 and 8.64 (2s, 1H), 9.05-9.08 (2s, 1H); MS (ESI) m/z 405 ([M+H]$^+$).

Preparation of 2-[[2-(4-thiazolyl)quinazolin-4-yl]carbonyl]-5,6-dimethoxy-1,2,3,4-tetrahydroisoquinoline (compound 81)

Reaction of 2-(4-thiazolyl)quinazoline-4-carboxylic acid with 5,6-dimethoxy-1,2,3,4-tetrahydroisoquinoline hydrochloride gave compound 81 (15% yield) as a white solid. $^1$H NMR (300 MHz, CDCl$_3$) δ 2.86 and 3.12 (2t, 2H), 3.54 and 4.16 (2t, 2H), 3.81-3.90 (m, 6H), 4.43 and 5.05 (2s, 2H), 6.51 and 6.90 (2d, 1H), 6.71 and 7.01 (2d, 1H), 7.63-7.68 (m, 1H), 7.94-8.04 (m, 2H), 8.28-8.31 (m, 1H), 8.53-8.57 (2s, 1H), 9.02-9.03 (2s, 1H); MS (ESI) m/z 433 ([M+H]$^+$).

Preparation of 2-[[2-(4-thiazolyl)quinazolin-4-yl]carbonyl]-5-hydroxy-6-dimethylamino-1,2,3,4-tetrahydroisoquinoline (compound 82)

Reaction of 2-(4-thiazolyl)quinazoline-4-carboxylic acid with 5-hydroxy-6-dimethylamino-1,2,3,4-tetrahydroisoquinoline hydrochloride gave compound 82 (39% yield) as a light yellow solid. $^1$H NMR (300 MHz, CD$_3$OD) δ 2.63 and 2.67 (2s, 6H), 2.82 and 3.06 (2m, 2H), 3.58 and 4.17 (2t, 2H), 4.46 and 5.03 (2s, 2H), 6.31 and 6.81 (2d, 1H), 6.91 and 7.12 (2d, 1H), 7.69-7.95 (m, 2H), 8.04-8.12 (m, 2H), 8.22-8.28 (m, 1H), 8.63-8.73 (2s, 1H), 9.21-9.23 (m, 1H); MS (ESI) m/z 432 ([M+H]$^+$).

Preparation of 2-[[2-(4-thiazolyl)quinazolin-4-yl]carbonyl]-5-hydroxy-6-methyl-1,2,3,4-tetrahydroisoquinoline (compound 83)

Reaction of 2-(4-thiazolyl)quinazoline-4-carboxylic acid with 5-hydroxy-6-methyl-1,2,3,4-tetrahydroisoquinoline hydrochloride gave compound 83 (40% yield) as a white solid. $^1$H NMR (300 MHz, CDCl$_3$) δ 2.25 and 2.28 (2s, 3H), 2.79 and 3.04 (2t, 2H), 3.59 and 4.22 (2t, 2H), 4.47 and 5.09 (2s, 2H), 6.32 and 6.82 (2d, 1H), 6.89 and 7.08 (2d, 1H), 7.58-7.69 (m, 1H), 7.93-8.05 (m, 2H), 8.31-8.35 (m, 1H), 8.56 and 8.61 (2s, 1H), 9.04 (s, 1H); MS (ESI) m/z 403 ([M+H]$^+$).

Preparation of 2-[[2-(3-pyridinyl)quinazolin-4-yl]carbonyl]-5-hydroxy-6-methoxy-1,2,3,4-tetrahydroisoquinoline (compound 84)

Reaction of 2-(3-pyridinyl)quinazoline-4-carboxylic acid with 5-hydroxy-6-methoxy-1,2,3,4-tetrahydroisoquinoline hydrochloride gave compound 84 (16% yield) as a light yellow solid. $^1$H NMR (300 MHz, CD$_3$OD) δ 2.82 and 3.08 (2t, 2H), 3.58 and 4.17 (2t, 2H), 3.83 and 3.89 (2s, 3H), 4.45 and 5.03 (2s, 2H), 6.29 and 6.79 (2d, 1H), 6.71 and 6.92 (2d, 1H), 7.60-8.25 (m, 5H), 8.71-8.72 (m, 1H), 8.92-9.05 (m, 1H), 9.68 and 9.73 (2s, 1H); MS (ESI) m/z 413 ([M+H]$^+$).

Preparation of 2-[[2-(3-pyridinyl)quinazolin-4-yl]carbonyl]-5,6-dihydroxy-1,2,3,4-tetrahydroisoquinoline (compound 85)

2-[[2-(3-pyridinyl)quinazolin-4-yl]carbonyl]-5,6-dihydroxy-1,2,3,4-tetrahydroisoquinoline was obtained from compound 84 (20% yield, gray solid) by the same way with the preparation of compound 2. $^1$H NMR (300 MHz, CD$_3$OD) δ 2.81 and 3.09 (2t, 2H), 3.58 and 4.17 (2t, 2H), 4.41 and 5.00 (2s, 2H), 6.17 and 6.67 (2d, 1H), 6.55 and 6.76 (2d, 1H), 7.64-8.26 (m, 5H), 8.69-8.73 (m, 1H), 8.93-9.03 (m, 1H), 9.68 and 9.74 (2s, 1H); MS (ESI) m/z 399 ([M+H]$^+$).

Preparation of 2-[[2-(3-pyridinyl)quinazolin-4-yl]carbonyl]-5,6-dimethoxy-1,2,3,4-tetrahydroisoquinoline (compound 86)

Reaction of 2-(3-pyridinyl)quinazoline-4-carboxylic acid with 5,6-dimethoxy-1,2,3,4-tetrahydroisoquinoline hydrochloride gave compound 86 (7% yield) as a white solid. $^1$H NMR (300 MHz, DMSO-d$_6$) δ 2.73 and 2.99 (2t, 2H), 3.51 and 4.03 (2t, 2H), 3.68-3.81 (4s, 6H), 4.44 and 4.94 (2s, 2H), 6.62 and 7.01 (2d, 1H), 6.80 and 7.08 (2d, 1H), 7.59-8.22 (m, 5H), 8.76-8.83 (m, 2H), 9.61-9.66 (m, 1H); MS (ESI) m/z 427 ([M+H]$^+$).

Preparation of 2-[[2-(3-pyridinyl)quinazolin-4-yl]carbonyl]-5-hydroxy-6-dimethylamino-1,2,3,4-tetrahydroisoquinoline (compound 87)

Reaction of 2-(3-pyridinyl)quinazoline-4-carboxylic acid with 5-hydroxy-6-dimethylamino-1,2,3,4-tetrahydroisoquinoline hydrochloride gave compound 87 (7% yield) as yellow oil. $^1$H NMR (300 MHz, CD$_3$OD) δ 2.77 and 2.80 (2s, 6H), 2.84 and 3.07 (2t, 2H), 3.60 and 4.20 (2t, 2H), 4.50 and 5.06 (2s, 2H), 6.39 and 6.88 (2d, 1H), 7.01 and 7.22 (2d, 1H), 7.62-7.82 (m, 2H), 7.96-8.25 (m, 3H), 8.71 (m, 1H), 8.92-9.02 (2d, 1H), 9.65 and 9.73 (2s, 1H); MS (ESI) m/z 426 ([M+H]$^+$).

Preparation of 2-[[2-(3-pyridinyl)quinazolin-4-yl]carbonyl]-5-hydroxy-6-methyl-1,2,3,4-tetrahydroisoquinoline (compound 88)

Reaction of 2-(3-pyridinyl)quinazoline-4-carboxylic acid with 5-hydroxy-6-methyl-1,2,3,4-tetrahydroisoquinoline hydrochloride gave compound 88 (13% yield) as a white solid. $^1$H NMR (300 MHz, DMSO-d$_6$) δ 2.13 and 2.17 (2s, 3H), 2.66 and 2.92 (2t, 2H), 3.52 and 4.05 (2t, 2H), 4.43 and 4.94 (2s, 2H), 6.30 and 6.75 (2d, 1H), 6.80 and 7.00 (2d, 1H), 7.61-8.23 (m, 5H), 8.39-8.45 (2s, 1H), 8.75-8.83 (m, 2H), 9.60 and 9.65 (2s, 1H); MS (ESI) m/z 397 ([M+H]$^+$).

Preparation of 2-[[2-(3,4,5-trimethoxyphenyl)quinazolin-4-yl]carbonyl]-5-hydroxy-6-methoxy-1,2,3,4-tetrahydroisoquinoline (compound 89)

Reaction of 2-(3,4,5-trimethoxyphenyl)quinazoline-4-carboxylic acid with 5-hydroxy-6-methoxy-1,2,3,4-tetrahydroisoquinoline hydrochloride gave compound 89 (18.9% yield). $^1$H NMR (300 MHz, DMSO-d$_6$) δ 2.77 and 2.90 (2t, 2H), 3.52 and 4.05 (2t, 2H), 3.74-3.80 (m, 6H), 3.87 and 3.92 (2s, 6H), 4.40 and 4.92 (2s, 2H), 6.31-6.92 (m, 2H), 7.67-8.17 (m, 6H), 8.70 and 8.73 (2s, 1H); MS (ESI) m/z 502 ([M+H]$^+$).

Preparation of 2-[[2-(3,4,5-trimethoxyphenyl)quinazolin-4-yl]carbonyl]-5-methoxy-1,2,3,4-tetrahydroisoquinoline (compound 90)

Reaction of 2-(3,4,5-trimethoxyphenyl)quinazoline-4-carboxylic acid with 5-methoxy-1,2,3,4-tetrahydroisoquinoline hydrochloride gave compound 90 (36.3% yield). $^1$H NMR (300 MHz, DMSO-d$_6$) δ 2.79 and 2.90 (2t, 2H), 3.56 and 4.08 (2t, 2H), 3.76-3.81 (m, 6H), 3.86 and 3.92 (2s, 6H), 4.50 and 4.99 (2s, 2H), 6.49-7.28 (m, 3H), 7.67-8.18 (m, 6H); MS (ESI) m/z 486 ([M+H]$^+$).

Preparation of 2-[[2-(3,4,5-trimethoxyphenyl)quinazolin-4-yl]carbonyl]-6-methoxy-1,2,3,4-tetrahydroisoquinoline (compound 91)

Reaction of 2-(3,4,5-trimethoxyphenyl)quinazoline-4-carboxylic acid with 6-methoxy-1,2,3,4-tetrahydroisoquinoline hydrochloride gave compound 91 (57.1% yield). $^1$H NMR (300 MHz, DMSO-d$_6$) δ 2.86 and 3.03 (2t, 2H), 3.51 and 4.04 (2t, 2H), 3.72-3.78 (m, 6H), 3.87 and 3.92 (2s, 6H), 4.43 and 4.94 (2s, 2H), 6.65-7.27 (m, 3H), 7.68-8.18 (m, 6H); MS (ESI) m/z 486 ([M+H]$^+$).

Preparation of 2-[[2-(3,4,5-trimethoxyphenyl)quinazolin-4-yl]carbonyl]-5,7-dimethoxy-1,2,3,4-tetrahydroisoquinoline (compound 92)

Reaction of 2-(3,4,5-trimethoxyphenyl)quinazoline-4-carboxylic acid with 5,7-dimethoxy-1,2,3,4-tetrahydroisoquinoline hydrochloride gave compound 92 (33.3% yield). $^1$H NMR (300 MHz, DMSO-d$_6$) δ 2.81 and 2.99 (2t, 2H), 3.45 (s, 1H), 3.49 and 4.04 (2t, 2H), 3.73-3.77 (m, 6H), 3.86 and 3.92 (m, 8H), 4.24 and 4.79 (2s, 2H), 6.33-6.50 (m, 2H), 7.72-8.17 (m, 6H); MS (ESI) m/z 516 ([M+H]$^+$).

Preparation of 2-[[2-(3,4,5-trimethoxyphenyl)quinazolin-4-yl]carbonyl]-5-hydroxy-1,2,3,4-tetrahydroisoquinoline (compound 93)

Reaction of 2-(3,4,5-trimethoxyphenyl)quinazoline-4-carboxylic acid with 5-hydroxy-1,2,3,4-tetrahydroisoquinoline hydrochloride gave compound 93 (18.8% yield). $^1$H NMR (300 MHz, DMSO-d$_6$) δ 2.74 and 2.87 (2t, 2H), 3.54 and 4.05 (2t, 2H), 3.76-3.78 (2s, 3H), 3.86 and 3.92 (2s, 6H), 4.46 and 4.96 (2s, 2H), 6.30-7.08 (m, 3H), 7.64-8.17 (m, 6H), 9.50 and 9.53 (2s, 1H); MS (ESI) m/z 472 ([M+H]$^+$).

Preparation of 2-[[2-(3,4,5-trimethoxyphenyl)quinazolin-4-yl]carbonyl]-6-fluoro-1,2,3,4-tetrahydroisoquinoline (compound 94)

Reaction of 2-(3,4,5-trimethoxyphenyl)quinazoline-4-carboxylic acid with 6-fluoro-1,2,3,4-tetrahydroisoquinoline hydrochloride gave compound 94 (63.4% yield). $^1$H NMR (300 MHz, DMSO-d$_6$) δ 2.88 and 3.07 (2t, 2H), 3.54 and 4.05 (2t, 2H), 3.76-3.78 (2s, 3H), 3.87 and 3.92 (2s, 6H), 4.50 and 5.00 (2s, 2H), 6.93-7.14 (m, 2H), 7.38-7.91 (m, 4H), 7.99-8.18 (m, 3H); MS (ESI) m/z 474 ([M+H]$^+$).

Preparation of 2-[[2-(4-nitrophenyl)quinazolin-4-yl]carbonyl]-5-hydroxy-6-methoxy-1,2,3,4-tetrahydroisoquinoline (compound 95)

Reaction of 2-(4-nitrophenyl)quinazoline-4-carboxylic acid with 5-hydroxy-6-methoxy-1,2,3,4-tetrahydroisoquinoline hydrochloride gave compound 95 (99.5% yield). $^1$H NMR (300 MHz, DMSO-d$_6$) δ 2.62 and 2.91 (2t, 2H), 3.50 and 4.04 (2t, 2H), 3.74-3.80 (2s, 3H), 4.41 and 4.93 (2s, 2H), 6.31 and 6.78 (2d, 1H), 6.71 and 6.91 (2d, 1H), 7.75-7.84 (m, 1H), 7.87-8.03 (2d, 1H), 8.16-8.26 (m, 2H), 8.41-8.46 (m, 2H), 8.72-8.79 (m, 3H); MS (ESI) m/z 457 ([M+H]$^+$).

Preparation of 2-[[2-(4-aminophenyl)quinazolin-4-yl]carbonyl]-5-hydroxy-6-methoxy-1,2,3,4-tetrahydroisoquinoline (compound 96)

Into a 1-L round-bottom flask purged and maintained with an inert atmosphere of nitrogen, was placed 2-[[2-(4-nitrophenyl)quinazolin-4-yl]carbonyl]-5-hydroxy-6-methoxy-1,2,3,4-tetrahydroisoquinoline (9 g, 19.72 mmol, 1.00 equiv), water (300 mL), ethanol (300 mL), Fe (2.5 g, 2.30 equiv) and NH$_4$Cl (2.4 g, 44.87 mmol, 2.30 equiv). The resulting solution was stirred overnight at 90° C. The solids were collected by filtration. The residue was dissolved in 200 mL of DMSO. The solids were filtered out. The resulting solution was diluted with 3 L of H$_2$O. The solids were collected by filtration. The filter cake was washed with 1×1 L of water. This resulted in 2.5 g (30%) of 2-[[2-(4-aminophenyl)quinazolin-4-yl]carbonyl]-6-methoxy-1,2,3,4-tetrahydroisoquinolin-5-ol as a yellow solid. $^1$H NMR (300 MHz, DMSO-d$_6$) δ 2.62 and 2.88 (2t, 2H), 3.45 and 4.01 (2t, 2H), 3.74-3.80 (2s, 3H), 4.36 and 4.89 (2s, 2H), 5.80 (s, 2H), 6.31-6.92 (m, 4H), 7.53-7.63 (m, 1H), 7.73-7.84 (2d, 1H), 7.94-7.99 (m, 2H), 8.18-8.25 (m, 2H), 8.68-8.74 (2s, 1H); MS (ESI) m/z 427 ([M+H]$^+$).

Preparation of 2-[[6-fluoro-2-(4-fluorophenyl)quinazolin-4-yl]carbonyl]-5-hydroxy-6-methoxy-1,2,3,4-tetrahydroisoquinoline (compound 97)

Reaction of 6-fluoro-2-(4-fluorophenyl)quinazoline-4-carboxylic acid with 5-hydroxy-6-methoxy-1,2,3,4-tetrahydroisoquinoline hydrochloride gave compound 97 (29.6% yield). $^1$H NMR (300 MHz, DMSO-d$_6$) δ 2.66 and 2.91 (2t, 2H), 3.52 and 4.02 (2t, 2H), 3.74 and 3.80 (2s, 3H), 4.44 and 4.90 (2s, 2H), 6.32-6.92 (m, 2H), 7.40-7.46 (m, 1H), 7.61-7.78 (m, 2H), 8.03-8.10 (m, 1H), 8.15-8.38 (m, 3H), 8.69 and 8.73 (2s, 1H); MS (ESI) m/z 448 ([M+H]$^+$).

Preparation of 2-[[6-fluoro-2-(4-fluorophenyl)quinazolin-4-yl]carbonyl]-5-methoxy-1,2,3,4-tetrahydroisoquinoline (compound 98)

Reaction of 6-fluoro-2-(4-fluorophenyl)quinazoline-4-carboxylic acid with 5-methoxy-1,2,3,4-tetrahydroisoquinoline hydrochloride gave compound 98 (13.4% yield). $^1$H NMR (400 MHz, CDCl$_3$) δ 2.83 and 3.05 (2t, 2H), 3.61 and 4.20 (2t, 2H), 3.85 and 3.89 (2s, 3H), 4.57 and 5.12 (2s, 2H), 6.44-6.93 (m, 2H), 7.10-7.27 (m, 2H), 7.50-7.53 (m, 1H), 7.69-7.76 (m, 2H), 8.18-8.21 (m, 1H), 8.33-8.36 (m, 1H), 8.40-8.45 (m, 1H); MS (ESI) m/z 432 ([M+H]$^+$).

Preparation of 2-[[6-fluoro-2-(4-fluorophenyl)quinazolin-4-yl]carbonyl]-6-methoxy-1,2,3,4-tetrahydroisoquinoline (compound 99)

Reaction of 6-fluoro-2-(4-fluorophenyl)quinazoline-4-carboxylic acid with 6-methoxy-1,2,3,4-tetrahydroisoquinoline hydrochloride gave compound 99 (50.6% yield). $^1$H NMR (400 MHz, DMSO-d$_6$) δ 2.80 and 3.03 (2t, 2H), 3.54 and 4.02 (2t, 2H), 3.72 and 3.74 (2s, 3H), 4.47 and 4.92 (2s, 2H), 6.65-7.27 (m, 3H), 7.40-7.48 (m, 1H), 7.62-7.82 (m, 2H), 8.05-8.10 (m, 1H), 8.20-8.39 (m, 3H); MS (ESI) m/z 432 ([M+H]$^+$).

Preparation of 2-[[6-fluoro-2-(4-fluorophenyl)quinazolin-4-yl]carbonyl]-5,7-dimethoxy-1,2,3,4-tetrahydroisoquinoline (compound 100)

Reaction of 6-fluoro-2-(4-fluorophenyl)quinazoline-4-carboxylic acid with 5,7-dimethoxy-1,2,3,4-tetrahydroisoquinoline hydrochloride gave compound 100 (42.3% yield). $^1$H NMR (300 MHz, DMSO-d$_6$) δ 2.76 and 3.00 (2t, 2H), 3.48 (s, 1H), 3.52 and 4.04 (2t, 2H), 3.74-3.75 (2s, 3H), 3.87 (s, 2H), 4.32 and 4.78 (2s, 2H), 6.36-6.50 (m, 2H), 7.42-7.48 (m, 1H), 7.64-7.81 (2m, 2H), 8.03-8.39 (m, 4H); MS (ESI) m/z 462 ([M+H]$^+$).

Preparation of 2-[[6-fluoro-2-(4-fluorophenyl)quinazolin-4-yl]carbonyl]-5-hydroxy-1,2,3,4-tetrahydroisoquinoline (compound 101)

Reaction of 6-fluoro-2-(4-fluorophenyl)quinazoline-4-carboxylic acid with 5-hydroxy-1,2,3,4-tetrahydroisoquinoline hydrochloride gave compound 101 (22.8% yield). $^1$H NMR (300 MHz, DMSO-d$_6$) δ 2.62 and 2.88 (2t, 2H), 3.54 and 4.05 (2t, 2H), 4.49 and 4.95 (2s, 2H), 6.35-6.79 (m, 2H), 6.85-7.07 (m, 1H), 7.42-7.45 (m, 1H), 7.64-7.80 (m, 2H), 8.04-8.10 (m 1H), 8.15-8.39 (m, 3H), 9.49 and 9.53 (2s, 1H); MS (ESI) m/z 418 ([M+H]$^+$).

Preparation of 2-[[6-fluoro-2-(4-fluorophenyl)quinazolin-4-yl]carbonyl]-6-fluoro-1,2,3,4-tetrahydroisoquinoline (compound 102)

Reaction of 6-fluoro-2-(4-fluorophenyl)quinazoline-4-carboxylic acid with 6-fluoro-1,2,3,4-tetrahydroisoquinoline hydrochloride gave compound 102 (26.7% yield). $^1$H NMR (400 MHz, CDCl$_3$) δ 2.95 and 3.13 (2t, 2H), 3.64 and 4.20 (2t, 2H), 4.56 and 5.09 (2s, 2H), 6.82-7.28 (m, 4H), 7.50-7.54 (m, 1H), 7.70-7.77 (m, 2H), 8.17-8.21 (m, 1H), 8.28-8.35 (m 1H), 8.40-8.44 (m, 1H); $^{19}$F (376 MHz, DMSO-$d_6$) δ −108.2, −112.8, −115.0, −115.6; MS (ESI) m/z 420 ([M+H]$^+$).

Preparation of 2-[[6-fluoro-2-(3,4,5-trimethoxyphenyl)quinazolin-4-yl]carbonyl]-5-hydroxy-6-methoxy-1,2,3,4-tetrahydroisoquinoline (compound 103)

Reaction of 6-fluoro-2-(3,4,5-trimethoxyphenyl)quinazoline-4-carboxylic acid with 5-hydroxy-6-methoxy-1,2,3,4-tetrahydroisoquinoline hydrochloride gave compound 103 (18.6% yield). $^1$H NMR (300 MHz, DMSO-$d_6$) δ 2.82 and 2.91 (2t, 2H), 3.56 and 4.02 (2t, 2H), 3.74-3.80 (m, 6H), 3.86 and 3.91 (2s, 6H), 4.45 and 4.90 (2s, 2H), 6.33-6.91 (m, 2H), 7.62-7.86 (m, 3H), 8.00-8.06 (m, 1H), 8.21-8.28 (m, 1H), 8.70 and 8.73 (2s, 1H); MS (ESI) m/z 520 ([M+H]$^+$).

Preparation of 2-[[6-fluoro-2-(3,4,5-trimethoxyphenyl)quinazolin-4-yl]carbonyl]-5-methoxy-1,2,3,4-tetrahydroisoquinoline (compound 104)

Reaction of 6-fluoro-2-(3,4,5-trimethoxyphenyl)quinazoline-4-carboxylic acid with 5-methoxy-1,2,3,4-tetrahydroisoquinoline hydrochloride gave compound 104 (41.1% yield). $^1$H NMR (300 MHz, DMSO-$d_6$) δ 2.88 and 3.03 (2t, 2H), 3.55 and 4.02 (2t, 2H), 3.72-3.3.77 (m, 6H), 3.86 and 3.92 (2s, 6H), 4.48 and 4.92 (2s, 2H), 6.63-7.27 (m, 3H), 7.62-7.85 (m, 3H), 7.98-8.07 (m, 1H), 8.23-8.26 (m, 1H); MS (ESI) m/z 504 ([M+H]$^+$).

Preparation of 2-[[6-fluoro-2-(3,4,5-trimethoxyphenyl)quinazolin-4-yl]carbonyl]-6-methoxy-1,2,3,4-tetrahydroisoquinoline (compound 105)

Reaction of 6-fluoro-2-(3,4,5-trimethoxyphenyl)quinazoline-4-carboxylic acid with 6-methoxy-1,2,3,4-tetrahydroisoquinoline hydrochloride gave compound 105 (53.8% yield). $^1$H NMR (300 MHz, DMSO-$d_6$) δ 2.84 and 2.90 (2t, 2H), 3.60 and 4.06 (2t, 2H), 3.76-3.3.81 (m, 6H), 3.85 and 3.92 (2s, 6H), 4.55 and 4.98 (2s, 2H), 6.50-7.27 (m, 3H), 7.62-7.86 (m, 3H), 7.98-8.07 (m, 1H), 8.23-8.28 (m, 1H); MS (ESI) m/z 504 ([M+H]$^+$).

Preparation of 2-[[6-fluoro-2-(3,4,5-trimethoxyphenyl)quinazolin-4-yl]carbonyl]-5,7-dimethoxy-1,2,3,4-tetrahydroisoquinoline (compound 106)

Reaction of 6-fluoro-2-(3,4,5-trimethoxyphenyl)quinazoline-4-carboxylic acid with 5,7-dimethoxy-1,2,3,4-tetrahydroisoquinoline hydrochloride gave compound 106 (34.3% yield). $^1$H NMR (300 MHz, DMSO-$d_6$) δ 2.84 and 2.99 (2t, 2H), 3.48 (s, 1H), 3.53 and 4.03 (2t, 2H), 3.69-3.3.81 (m, 6H), 3.86-3.92 (m, 8H), 4.31 and 4.77 (2s, 2H), 6.35-6.50 (m, 2H), 7.66-7.85 (m, 3H), 8.02-8.05 (m, 1H), 8.23-8.28 (m, 1H); MS (ESI) m/z 534 ([M+H]$^+$).

Preparation of 2-[[6-fluoro-2-(3,4,5-trimethoxyphenyl)quinazolin-4-yl]carbonyl]-5-hydroxy-1,2,3,4-tetrahydroisoquinoline (compound 107)

Reaction of 6-fluoro-2-(3,4,5-trimethoxyphenyl)quinazoline-4-carboxylic acid with 5-hydroxy-1,2,3,4-tetrahydroisoquinoline hydrochloride gave compound 107 (15.4% yield). $^1$H NMR (300 MHz, DMSO-$d_6$) δ 2.80 and 2.89 (2t, 2H), 3.59 and 4.07 (2t, 2H), 3.77-3.3.80 (m, 3H), 3.87 and 3.92 (2s, 6H), 4.51 and 4.95 (2s, 2H), 6.35-6.79 (m, 2H), 6.89-7.11 (m, 1H), 7.64-7.85 (m, 3H), 8.00-8.09 (m, 1H), 8.22-8.29 (m, 1H), 9.51 and 9.53 (2s, 1H); MS (ESI) m/z 490 ([M+H]$^+$).

Preparation of 2-[[6-fluoro-2-(3,4,5-trimethoxyphenyl)quinazolin-4-yl]carbonyl]-6-fluoro-1,2,3,4-tetrahydroisoquinoline (compound 108)

Reaction of 6-fluoro-2-(3,4,5-trimethoxyphenyl)quinazoline-4-carboxylic acid with 6-fluoro-1,2,3,4-tetrahydroisoquinoline hydrochloride gave compound 108 (54.3% yield). $^1$H NMR (300 MHz, DMSO-$d_6$) δ 2.92 and 3.07 (2t, 2H), 3.58 and 4.04 (2t, 2H), 3.76-3.3.77 (d, 3H), 3.86 and 3.91 (2s, 6H), 4.55 and 4.98 (2s, 2H), 6.95-7.41 (m, 3H), 7.65-7.85 (m, 3H), 7.99-8.05 (m, 1H), 8.23-8.28 (m, 1H); MS (ESI) m/z 492 ([M+H]$^+$).

Preparation of 2-[[6,7-dimethoxy-2-(4-fluorophenyl)quinazolin-4-yl]carbonyl]-5-hydroxy-6-methoxy-1,2,3,4-tetrahydroisoquinoline (compound 109)

Reaction of 6,7-dimethoxy-2-(4-fluorophenyl)quinazoline-4-carboxylic acid with 5-hydroxy-6-methoxy-1,2,3,4-tetrahydroisoquinoline hydrochloride gave compound 109 (18.0% yield). $^1$H NMR (300 MHz, DMSO-$d_6$) δ 2.67 and 2.92 (2t, 2H), 3.45-4.06 (m, 11H), 4.37 and 4.90 (2s, 2H), 6.27-7.11 (m, 3H), 7.36-7.42 (m, 1H), 7.50-7.65 (m, 2H), 8.12-8.20 (m, 1H), 8.29-8.35 (m, 1H), 8.68 and 8.73 (2s, 1H); MS (ESI) m/z 490 ([M+H]$^+$).

Preparation of 2-[[6,7-dimethoxy-2-(4-fluorophenyl)quinazolin-4-yl]carbonyl]-5-methoxy-1,2,3,4-tetrahydroisoquinoline (compound 110)

Reaction of 6,7-dimethoxy-2-(4-fluorophenyl)quinazoline-4-carboxylic acid with 5-methoxy-1,2,3,4-tetrahydroisoquinoline hydrochloride gave compound 110 (20.2% yield). $^1$H NMR (400 MHz, DMSO-$d_6$) δ 2.67 and 2.92 (2t, 2H), 3.51-4.09 (m, 11H), 4.47 and 4.98 (2s, 2H), 6.47-7.28 (m, 4H), 7.38-7.42 (m, 1H), 7.51-7.55 (2s, 1H), 7.59-7.63 (m, 1H), 8.15-8.20 (m, 1H), 8.30-8.35 (m, 1H); $^{19}$F (376 MHz, DMSO-$d_6$) δ-113.0; MS (ESI) m/z 474 ([M+H]$^+$).

Preparation of 2-[[6,7-dimethoxy-2-(4-fluorophenyl)quinazolin-4-yl]carbonyl]-6-methoxy-1,2,3,4-tetrahydroisoquinoline (compound 111)

Reaction of 6,7-dimethoxy-2-(4-fluorophenyl)quinazoline-4-carboxylic acid with 6-methoxy-1,2,3,4-tetrahydroisoquinoline hydrochloride gave compound 111 (19.2% yield). $^1$H NMR (400 MHz, DMSO-$d_6$) δ 2.81 and 3.05 (2t, 2H), 3.48-4.06 (m, 11H), 4.41 and 4.93 (2s, 2H), 6.66-6.92 (m, 3H), 7.14-7.27 (m, 1H), 7.37-7.41 (m, 1H), 7.51 and 7.54 (2s, 1H), 7.59-7.63 (m, 1H), 8.15-8.20 (m, 1H), 8.31-8.35 (m, 1H); $^{19}$F (376 MHz, DMSO-$d_6$) δ −113.0; MS (ESI) m/z 474 ([M+H]$^+$).

Preparation of 2-[[6,7-dimethoxy-2-(4-fluorophenyl)quinazolin-4-yl]carbonyl]-5,7-dimethoxy-1,2,3,4-tetrahydroisoquinoline (compound 112)

Reaction of 6,7-dimethoxy-2-(4-fluorophenyl)quinazoline-4-carboxylic acid with 5,7-dimethoxy-1,2,3,4-tetrahydroisoquinoline hydrochloride gave compound 112 (49.2% yield). $^1$H NMR (300 MHz, DMSO-$d_6$) δ 2.76 and 3.02 (2t, 2H), 3.45-4.08 (m, 14H), 4.24 and 4.78 (2s, 2H), 6.34-6.52

(m, 2H), 6.96 and 7.14 (2s, 1H), 7.36-7.41 (m, 1H), 7.52-7.65 (m, 2H), 8.11-8.21 (m, 1H), 8.28-8.35 (m, 1H); MS (ESI) m/z 504 ([M+H]$^+$).

Preparation of 2-[[6,7-dimethoxy-2-(4-fluorophenyl) quinazolin-4-yl]carbonyl]-5-hydroxy-1,2,3,4-tetrahydroisoquinoline (compound 113)

Reaction of 6,7-dimethoxy-2-(4-fluorophenyl)quinazoline-4-carboxylic acid with 5-hydroxy-1,2,3,4-tetrahydroisoquinoline hydrochloride gave compound 113 (27.4% yield). $^1$H NMR (300 MHz, DMSO-d$_6$) δ 2.64 and 2.89 (2t, 2H), 3.47-4.09 (m, 8H), 4.42 and 4.94 (2s, 2H), 6.29-6.78 (m, 2H), 6.85-7.12 (m, 2H), 7.36-7.42 (m, 1H), 7.50-7.65 (m, 2H), 8.12-8.21 (m, 1H), 8.29-8.35 (m, 1H), 9.48 and 9.54 (2s, 1H); MS (ESI) m/z 460 ([M+H]$^+$).

Preparation of 2-[[6,7-dimethoxy-2-(4-fluorophenyl) quinazolin-4-yl]carbonyl]-6-fluoro-1,2,3,4-tetrahydroisoquinoline (compound 114)

Reaction of 6,7-dimethoxy-2-(4-fluorophenyl)quinazoline-4-carboxylic acid with 6-fluoro-1,2,3,4-tetrahydroisoquinoline hydrochloride gave compound 114 (17.9% yield). $^1$H NMR (400 MHz, DMSO-d$_6$) δ 2.84 and 3.09 (2t, 2H), 3.50-4.06 (m, 8H), 4.47 and 4.98 (2s, 2H), 6.94-7.43 (m, 5H), 7.52-7.55 (2s, 1H), 7.59-7.65 (m, 1H), 8.13-8.21 (m, 1H), 8.30-8.35 (m, 1H); $^{19}$F (376 MHz, DMSO-d$_6$) δ −113.0, −116.1, −116.3; MS (ESI) m/z 462 ([M+H]$^+$).

Preparation of 2-[[6,7-dimethoxy-2-(3,4,5-trimethoxyphenyl)quinazolin-4-yl]carbonyl]-5-hydroxy-6-methoxy-1,2,3,4-tetrahydroisoquinoline (compound 115)

Reaction of 6,7-dimethoxy-2-(3,4,5-trimethoxyphenyl) quinazoline-4-carboxylic acid with 5-hydroxy-6-methoxy-1, 2,3,4-tetrahydroisoquinoline hydrochloride gave compound 115 (13.6% yield). $^1$H NMR (300 MHz, DMSO-d$_6$) δ 2.83 and 2.90 (2t, 2H), 3.49-4.05 (m, 20H), 4.37 and 4.90 (2s, 2H), 6.27-7.16 (m, 3H), 7.46 and 7.50 (2s, 1H), 7.78 and 7.84 (2s, 2H), 8.70 and 8.73 (2s, 1H); MS (ESI) m/z 562 ([M+H]$^+$).

Preparation of 2-[[6,7-dimethoxy-2-(3,4,5-trimethoxyphenyl)quinazolin-4-yl]carbonyl]-5-methoxy-1,2,3,4-tetrahydroisoquinoline (compound 116)

Reaction of 6,7-dimethoxy-2-(3,4,5-trimethoxyphenyl) quinazoline-4-carboxylic acid with 5-methoxy-1,2,3,4-tetrahydroisoquinoline hydrochloride gave compound 116 (41.6% yield). $^1$H NMR (300 MHz, DMSO-d$_6$) δ 2.84 and 2.90 (2t, 2H), 3.52-4.09 (m, 20H), 4.45 and 4.96 (2s, 2H), 6.45-7.26 (m, 4H), 7.45 and 7.49 (2s, 1H), 7.76 and 7.82 (2s, 2H); MS (ESI) m/z 546 ([M+H]$^+$).

Preparation of 2-[[6,7-dimethoxy-2-(3,4,5-trimethoxyphenyl)quinazolin-4-yl]carbonyl]-6-methoxy-1,2,3,4-tetrahydroisoquinoline (compound 117)

Reaction of 6,7-dimethoxy-2-(3,4,5-trimethoxyphenyl) quinazoline-4-carboxylic acid with 6-methoxy-1,2,3,4-tetrahydroisoquinoline hydrochloride gave compound 117 (32.7% yield). $^1$H NMR (300 MHz, DMSO-d$_6$) δ 2.89 and 3.05 (2t, 2H), 3.48-4.05 (m, 20H), 4.40 and 4.92 (2s, 2H), 6.65-7.26 (m, 4H), 7.47 and 7.50 (2s, 1H), 7.78 and 7.83 (2s, 2H); MS (ESI) m/z 546 ([M+H]$^+$).

Preparation of 2-[[6,7-dimethoxy-2-(3,4,5-trimethoxyphenyl)quinazolin-4-yl]carbonyl]-5,7-dimethoxy-1,2,3,4-tetrahydroisoquinoline (compound 118)

Reaction of 6,7-dimethoxy-2-(3,4,5-trimethoxyphenyl) quinazoline-4-carboxylic acid with 5,7-dimethoxy-1,2,3,4-tetrahydroisoquinoline hydrochloride gave compound 118 (45.3% yield). $^1$H NMR (300 MHz, DMSO-d$_6$) δ 2.86 and 3.01 (2t, 2H), 3.45-4.05 (m, 23H), 4.23 and 4.77 (2s, 2H), 6.33-6.49 (m, 2H), 6.90 and 7.15 (2s, 1H), 7.48 and 7.50 (2s, 1H), 7.78 and 7.83 (2s, 2H); MS (ESI) m/z 576 ([M+H]$^+$).

Preparation of 2-[[6,7-dimethoxy-2-(3,4,5-trimethoxyphenyl)quinazolin-4-yl]carbonyl]-5-hydroxy-1,2,3,4-tetrahydroisoquinoline (compound 119)

Reaction of 6,7-dimethoxy-2-(3,4,5-trimethoxyphenyl) quinazoline-4-carboxylic acid with 5-hydroxy-1,2,3,4-tetrahydroisoquinoline hydrochloride gave compound 119 (9.3% yield). $^1$H NMR (300 MHz, DMSO-d$_6$) δ 2.80 and 2.90 (2t, 2H), 3.52-4.07 (m, 17H), 4.42 and 4.94 (2s, 2H), 6.29-7.17 (m, 4H), 7.48 and 7.51 (2s, 1H), 7.78 and 7.84 (2s, 2H), 9.50 and 9.52 (2s, 1H); MS (ESI) m/z 532 ([M+H]$^+$).

Preparation of 2-[[6,7-dimethoxy-2-(3,4,5-trimethoxyphenyl)quinazolin-4-yl]carbonyl]-6-fluoro-1,2,3,4-tetrahydroisoquinoline (compound 120)

Reaction of 6,7-dimethoxy-2-(3,4,5-trimethoxyphenyl) quinazoline-4-carboxylic acid with 6-fluoro-1,2,3,4-tetrahydroisoquinoline hydrochloride gave compound 120 (56.2% yield). $^1$H NMR (300 MHz, DMSO-d$_6$) δ 2.93 and 3.09 (2t, 2H), 3.51-4.05 (m, 17H), 4.47 and 4.98 (2s, 2H), 6.91-7.42 (m, 4H), 7.48 and 7.51 (2s, 1H), 7.78 and 7.83 (2s, 2H); MS (ESI) m/z 534 ([M+H]$^+$).

Pharmaceutical Preparation

The following illustrate representative pharmaceutical dosage forms containing a compound of formula (I), or a pharmaceutically acceptable salt thereof for therapeutic or prophylactic use in, e.g., humans. The formulations may be obtained by conventional procedures well known in the pharmaceutical art and are not limited to the representative pharmaceutical dosage forms.

Tablet (Direct Pressure)

The sieved compound (5.0 mg) is mixed with lactose (14.1 mg), Crosspovidone USNF (0.8 mg) and magnesium stearate (0.1 mg). The mixture is compressed into tablets.

Tablet (Hydroassembly)

The sieved compound (5.0 mg) is mixed with lactose (16.0 mg), starch (4.0 mg) and polysorbate 80 (0.3 mg). Pure water is added to the mixture and the mixture dissolved. The mixture is formed into a particle and the particle dried, sieved and mixed with colloidal silicon dioxide (2.7 mg) and magnesium stearate (2.0 mg). The particle is compressed into tablets.

Powder and Capsule

The sieved compound (5.0 mg) is mixed with lactose (14.8 mg), polyinylpyrrolidone (10.0 mg) and magnesium stearate (0.2 mg). The mixture is filled into No. 5 gelatin capsule using suitable equipment.

Injection

The compound (100 mg), mannitol (180 mg) and Na$_2$HPO$_4$.12H$_2$O (26 mg) are dissolved in about 2974 ml of distilled water.

Biological Tests

1) Growth of Cancer Cell Lines

Cancer cells used in this study to determine the effect of tetrahydroisoquinolin-2-yl-(quinazolin-4-yl)methanone compounds were obtained from the following sources: Human OVCAR-3 (ovary), SK-MEL-28 (melanoma), MDA-MB-231 (breast), HeLa (cervix), PC3 (prostate), HepG2 (liver), A549 (lung), Caki-1 (kidney), HCT116 (colon) and PANC-1 (pancreas) from the American Type Culture Collection (ATCC) (Manassas, Va.); U251 (brain) from Riken (Japan); MKN-45 (stomach) from DSMZ (Germany). All cell lines except MDA-MB-231, HCT116, Caki-1 and PANC-1 were grown in RPMI1640 medium (Invitrogen, Carlsbad, Calif.) supplemented with 10% fetal bovine serum ("FBS"), 1 mM sodium pyruvate, 10 mM HEPES and 100 U/ml penicillin and 100 µg/ml streptomycin ("P/S"). MDA-MB-231, HCT116, Caki-1 and PANC-1 cells were maintained in Dulbecco's modified Eagle's medium ("DMEM", Invitrogen) supplemented with 10% FBS, P/S, 10 mM HEPES and 2 mM L-glutamine. All cells were incubated at 37° C. under humidified 5% $CO_2$.

2) In Vitro Cell Proliferation Assay Against Human Tumor Cell Lines

The growth inhibition of the tetrahydroisoquinolin-2-yl-(quinazolin-4-yl)methanone compounds against a variety of human tumor cells was evaluated to study the relative importance of particular substituent groups on the compounds. The tetrahydroisoquinolin-2-yl-(quinazolin-4-yl)methanone compounds, prepared as described above, were tested with DMSO as a control.

The growth inhibition assay of representative tetrahydroisoquinolin-2-yl-(quinazolin-4-yl)methanone derivatives against human tumor cell lines was performed using the Sulforhodamine B ("SRB") method (Skehan et al., J. National Cancer Institute, 82: 1107-1112 (1990)). Briefly, exponentially growing tumor cells were seeded into a 96-well plate at a density of $2-3 \times 10^3$ cells/well and treated with tetrahydroisoquinolin-2-yl-(quinazolin-4-yl)methanone compounds the next day. Triplicate wells were used for each treatment. The cells were incubated with the various compounds for 96 hours at 37° C. in a humidified 5% $CO_2$ atmosphere. After 96-hour incubation, cells were fixed with 10% trichloroacetic acid ("TCA"), incubated for 1 hour at 4° C., and washed 3 times with tap water. Subsequently, cells were stained with 0.4% sulforhodamine B in 1% acetic acid for 30 minutes, washed 4 times with 1% acetic acid, and air-dried again. After 5 minutes agitation in 10 mM Tris solution, the absorbance of each well was measured at 530 nm using Benchmark Plus Microplate reader (Bio-Rad Laboratories, Hercules, Calif.).

To translate the $OD_{530}$ values into the number of live cells in each well, the $OD_{530}$ values were compared to those on standard $OD_{530}$-versus-cell number curves generated for each cell line. The percent survival was calculated using the formula:

% Survival=live cell number[test]/live cell number [control]×100

The $IC_{50}$ values were calculated by non-linear regression analysis.

The compounds were screened against at least cancer cell lines including PANC-1, MDA-MB-231, HCT116 and Caki-1, at approximately 1 µM concentration. The inhibition of cell growth ($IC_{50}$, µM) of some tetrahydroisoquinolin-2-yl-(quinazolin-4-yl) methanone compounds are shown in Table 2.

TABLE 2

Inhibition of cell growth ($IC_{50}$, µM) by tetrahydroisoquinolin-2-yl-(quinazolin-4-yl)methanone compounds against human cancer cell lines

| Compound No. | MDA-MB-231 | HCT116 | Caki-1 | Panc-1 | MKN-45 | SK-MEL-28 | HeLa | Ovcar3 | U251 | HepG2 | A549 | PC-3 |
|---|---|---|---|---|---|---|---|---|---|---|---|---|
| 1 | 0.060 | 0.069 | 0.056 | 0.057 | 0.058 | 0.063 | 0.063 | 0.060 | 0.067 | 0.12 | 0.14 | 0.076 |
| 3 | 1.20 | 1.39 | 1.10 | 1.45 | | | | | | | | |
| 5 | 0.38 | 0.47 | 0.36 | 0.40 | | | | | | | | |
| 7 | 0.90 | 1.10 | 0.61 | 0.53 | 0.19 | 0.36 | 0.24 | 0.16 | 0.64 | 0.72 | | |
| 12 | 0.23 | 0.29 | 0.20 | 0.18 | | | | | | | | |
| 16 | 1.50 | 2.05 | 1.61 | 1.72 | | | | | | | | |
| 17 | 0.066 | 0.081 | 0.057 | 0.062 | 0.063 | 0.069 | 0.074 | 0.074 | 0.067 | 0.14 | 0.15 | 0.076 |
| 19 | 0.84 | 1.08 | 0.85 | 1.06 | | | | | | | | |
| 21 | 0.27 | 0.34 | 0.23 | 0.22 | | | | | | | | |
| 22 | 0.052 | 0.086 | 0.057 | 0.056 | 0.055 | 0.072 | 0.064 | 0.080 | 0.069 | 0.19 | 0.15 | 0.076 |
| 24 | 0.41 | 0.49 | 0.38 | 0.46 | | | | | | | | |
| 25 | 2.53 | | | 1.77 | | | | | | | | |
| 26 | 0.19 | 0.22 | 0.16 | 0.18 | | | | | | | | |
| 27 | 0.54 | 0.50 | 0.46 | 0.42 | | | | | | | | |
| 31 | 0.63 | 0.91 | 0.64 | 0.85 | | | | | | | | |
| 32 | 0.43 | 0.52 | 0.37 | 0.47 | | | | | | | | |
| 37 | 0.42 | 0.55 | 0.36 | 0.43 | | | | | | | | |
| 42 | 0.12 | 0.14 | 0.082 | 0.12 | 0.051 | 0.098 | 0.12 | 0.15 | 0.11 | 0.20 | 0.21 | 0.15 |
| 46 | 0.58 | 0.54 | 0.52 | 0.51 | | | | | | | | |
| 47 | 0.49 | 0.81 | 0.59 | 0.50 | | | | | | | | |
| 52 | 1.62 | 2.67 | 1.91 | 2.51 | | | | | | | | |
| 54 | 3.44 | 1.65 | | | | | | | | | | |
| 57 | 0.17 | 0.22 | 0.21 | 0.19 | | 0.20 | | 0.23 | 0.17 | 0.31 | | 0.21 |
| 61 | 1.84 | 2.76 | 2.47 | 2.31 | | | | | | | | |
| 62 | 0.20 | 0.34 | 0.20 | 0.21 | | | | | | | | |
| 64 | 0.52 | 0.89 | 0.63 | 0.68 | | | | | | | | |
| 70 | 0.045 | 0.068 | 0.055 | 0.054 | 0.058 | 0.059 | 0.074 | 0.068 | 0.064 | 0.096 | 0.11 | 0.049 |

TABLE 2-continued

Inhibition of cell growth (IC$_{50}$, μM) by tetrahydroisoquinolin-2-yl-(quinazolin-4-yl)methanone compounds against human cancer cell lines

| Compound No. | MDA-MB-231 | HCT116 | Caki-1 | Panc-1 | MKN-45 | SK-MEL-28 | HeLa | Ovcar3 | U251 | HepG2 | A549 | PC-3 |
|---|---|---|---|---|---|---|---|---|---|---|---|---|
| 72 | 0.46 | 0.55 | 0.39 | 0.49 | | | | | | | | |
| 73 | 0.21 | 0.26 | 0.19 | 0.20 | | | | | | | | |
| 79 | 0.17 | 0.20 | 0.16 | 0.17 | | | | | | | | |
| 81 | 1.00 | 1.26 | 1.21 | 1.43 | | | | | | | | |
| 83 | 0.21 | 0.29 | 0.25 | 0.23 | | | | | | | | |
| 84 | 0.13 | 0.15 | 0.093 | 0.15 | 0.071 | 0.13 | 0.15 | 0.14 | 0.11 | 0.20 | 0.24 | 0.15 |
| 88 | 0.67 | 1.12 | 0.97 | 0.93 | | | | | | | | |
| 95 | 0.11 | 0.16 | | 0.20 | | | | | | | | |
| 96 | 0.23 | 0.36 | | 0.28 | | | | | | | | |
| 97 | 0.16 | 0.17 | 0.11 | 0.13 | 0.087 | 0.11 | 0.16 | 0.073 | 0.13 | 0.18 | | |

Tetrahydroisoquinolin-2-yl-(quinazolin-4-yl)methanone compounds shown in Table 2 are active against a broad range of tumor cell lines. Many of the compounds have activities, as determined by the IC$_{50}$ value, of significantly less than 1 μM or 0.5 μM or even 0.1 μM. As can be seen from Table 2, many of the other compounds tested exhibited IC$_{50}$<1 μM for a number of cell lines, with IC$_{50}$<0.3 μM in several. Values of IC$_{50}$ of less than or equal to 2.0 μM, 1.5 μM, 1.0 μM or 0.5 μM can reflect significant therapeutic activity. The IC$_{50}$ of the compounds of Table 2 thus reflect significant therapeutic activity.

3) Xenograft Study

Tumor growth inhibition by tetrahydroisoquinolin-2-yl-(quinazolin-4-yl)methanone compounds in an animal model was carried out by performing an ex vivo xenograft study of nude mice was conducted with Compound 1. Suitable human cancer cell lines are those that have been tested previously for inhibition of cancer cell growth. The antitumor efficacy of Compound 1 was evaluated against subcutaneously injected tumor xenografts in nude mice. Tumor volume was measured after treatment with Compound 1.

A suspension of MDA-MB-231 cells (5×10$^6$ cells in 0% Marigel) was injected subcutaneously into the right flank of CR female NCr nu/nu mice on day 0. A sufficient number of mice were injected with MDA-MB-231 cell suspension (0.2 ml/mouse) so that tumors in a volume range as narrow as possible were selected for the trial on the day of treatment initiation. Animals with tumors in the proper size range (100~150 mm$^3$) were assigned to various treatment groups. Compound 1 was dissolved in the mixture of 15% dimethylacetamide and 30% Solutol® HS 15 in water. Solvent alone served as control. Compound 1 (50 mg/kg) was given by intraperitoneal injections three times per week starting from day 15 after inoculation of MDA-MB-231 cells. To quantify tumor growth, three perpendicular diameters of the tumors were measured with calipers every 3-4 days, and the body weight of the mice was monitored for toxicity. The tumor volume was calculated using the formula: tumor volume (mm$^3$)=(width)×(length)×(height)×π/6. Results are shown in FIG. 1.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:
1. A compound of formula (I):

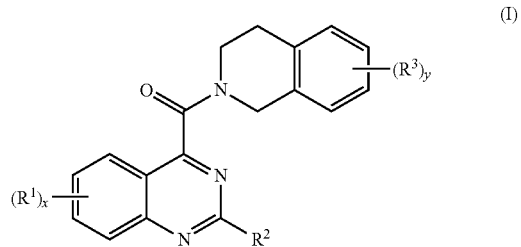

wherein:
each R$^1$, independently, is hydrogen, halogen, or —O—R$^4$;
R$^2$ is —(CR$^a$R$^b$)$_z$—R$^5$;
each R$^3$, independently, is hydrogen, halogen, —N(R$^4$)$_2$, —O—R$^4$, alkyl, alkoxy, alkenyl, alkynyl, cycloalkyl, heterocyclyl, aryl, or heteroaryl;
each R$^a$, independently, is hydrogen, halogen, hydroxy, alkyl, alkoxy, alkenyl, alkynyl, cycloalkyl, heterocyclyl, aryl, or heteroaryl;
each R$^b$, independently, is hydrogen, halogen, hydroxy, alkyl, alkoxy, alkenyl, alkynyl, cycloalkyl, heterocyclyl, aryl, or heteroaryl;
each R$^4$, independently, is hydrogen or C$_1$-C$_6$ alkyl;
R$^5$ is hydrogen, halo, alkyl, hydroxy, alkyl, alkoxy, alkenyl, alkynyl, cycloalkyl, heterocyclyl, —N(R$^4$)CO—R$^4$ or Ar;
Ar is aryl or heteroaryl, wherein each of aryl and heteroaryl is optionally substituted by one to five substituents independently selected from hydrogen, halogen, —R$^4$, —N(R$^4$)$_2$, nitro, —(CH$_2$)$_n$—NHCO—R$^4$, —O—R$^4$, alkyl, alkenyl, alkynyl, cycloalkyl, heterocyclyl, aryl, or heteroaryl;
n is 0, 1, 2, or 3;
x is 0, 1, 2, 3, or 4;
y is 0, 1, 2, 3, or 4; and
z is 0, 1, 2, 3, 4, 5, or 6;
or a pharmaceutically acceptable salt thereof.

2. The compound of claim 1, wherein $R^2$ is —$(CR^aR^b)_z$—$N(R^4)CO$—$R^4$, or Ar.

3. The compound of claim 1, wherein $R^2$ is Ar optionally substituted by one to five substituents independently selected from hydrogen, halogen, —$R^4$, —$N(R^4)_2$, and —O—$R^4$.

4. The compound of claim 3, wherein $R^2$ is aryl optionally substituted by one to five substituents independently selected from hydrogen, halogen, —$R^4$, —$N(R^4)_2$, and —O—$R^4$.

5. The compound of claim 3, wherein $R^2$ is heteroaryl optionally substituted by one to five substituents independently selected from hydrogen, halogen, —$R^4$, —$N(R^4)_2$, and —O—$R^4$.

6. The compound of claim 1, wherein x is 1 or 2 and each $R^1$, independently, is hydrogen, halogen or —$OR^4$.

7. The compound of claim 1, wherein y is 1 or 2 and each $R^3$, independently, is hydrogen, halogen, —$R^4$, —$N(R^4)_2$, or —$OR^4$.

8. The compound of claim 1, having the structure of formula (II):

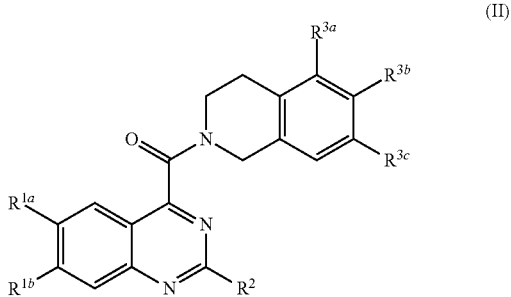

(II)

wherein:
each of $R^{1a}$ and $R^{1b}$, independently, is H, halogen, hydroxy, alkyl, haloalkyl, or alkoxy;
$R^2$ is acetamidoethyl or Ar, wherein Ar is selected from phenyl and heteroaryl, wherein each of phenyl and heteroaryl is optionally substituted by one to five substituents independently selected from hydrogen, halogen, —$R^4$, —$N(R^4)_2$, nitro, —O—$R^4$, —NHCO—$CH_3$, —$CH_2$—NHCO—$CH_3$, and trifluoromethyl;
each of $R^{3a}$, $R^{3b}$, and $R^{3c}$, independently, is H, halogen, hydroxy, alkyl, alkoxy, or —$N(R^4)_2$; and
each $R^4$, independently, is hydrogen or $C_1$-$C_6$ alkyl.

9. The compound of claim 8, wherein:
each of $R^{1a}$ and $R^{1b}$, independently, is hydrogen, halogen, or alkoxy;
$R^2$ is acetamidoethyl, 4-pyrimidinyl, 4-thiazolyl, 3-pyridinyl, or phenyl optionally substituted by 1 to 3 substituents independently selected from hydrogen, halogen, nitro, trifluoromethyl, amino, dimethylamino, —NHCO—$CH_3$, —$CH_2$—NHCO—$CH_3$, methyl, or methoxy;
each of $R^{3a}$, $R^{3b}$, and $R^{3c}$, independently, is hydrogen, halogen, hydroxyl, dimethylamino, methyl or methoxy; and
y is 1 or 2.

10. The compound of claim 8, wherein $R^{3c}$ is H.

11. The compound of claim 8 or salt thereof, wherein:
each $R^1$ is independently hydrogen or halogen;
$R^2$ is phenyl, 4-nitrophenyl, 4-aminophenyl, 3-fluorophenyl, 4-fluorophenyl, 2,4-difluorophenyl, 4-methylphenyl, 3-methoxyphenyl, 4-methoxyphenyl, 4-chlorophenyl, 4-(dimethylamino)phenyl, 3-(trifluoromethyl) phenyl, 4-(trifluoromethyl)phenyl, 4-acetamidophenyl, 4-pyrimidinyl, 4-thiazolyl or 3-pyridinyl;
$R^{3a}$ is hydroxy or methoxy;
$R^{3b}$ is methoxy, methyl, or dimethylamino; and
$R^{3c}$ is hydrogen.

12. The compound of claim 1, having an $IC_{50}$ of not greater than 1.0 µM with respect to at least one cell line for a tumor selected from breast tumors, prostate tumors, colon tumors, ovary tumors, kidney tumors, pancreas tumors, glioblastoma, stomach tumors, lung tumors, liver tumors, cervix and melanoma.

13. The compound of claim 12, wherein the cell line is selected from human MDA-MB-231, PC3, HCT116, OVCAR-3, Caki-1, PANC-1, U251, MKN-45, A549, HepG2, HeLa and SK-MEL-28.

14. The compound of claim 1, having an $IC_{50}$ of not greater than 0.1 µM with respect to at least one cell line for a tumor selected from breast tumors, prostate tumors, colon tumors, ovary tumors, kidney tumors, pancreas tumors, glioblastoma, stomach tumors, lung tumors, liver tumors, cervix and melanoma.

15. The compound or salt of claim 14, wherein the cell line is selected from human MDA-MB-231, PC3, HCT116, OVCAR-3, Caki-1, PANC-1, U251, MKN-45, A549, HepG2, HeLa and SK-MEL-28.

16. A compound selected from the group consisting of:
2-[[2-(4-fluorophenyl)quinazolin-4-yl]carbonyl]-5-hydroxy-6-methoxy-1,2,3,4-tetrahydroisoquinoline;
2-[[2-(4-fluorophenyl)quinazolin-4-yl]carbonyl]-5,6-dihydroxy-1,2,3,4-tetrahydroisoquinoline; 2-[[2-(4-fluorophenyl)quinazolin-4-yl]carbonyl]-5,6-dimethoxy-1,2,3,4-tetrahydroisoquinoline; 2-[[2-(4-fluorophenyl)quinazolin-4-yl]carbonyl]-5-hydroxy-6-dimethylamino-1,2,3,4-tetrahydroisoquinoline; 2-[[2-(4-fluorophenyl)quinazolin-4-yl]carbonyl]-5-hydroxy-6-methyl-1,2,3,4-tetrahydroisoquinoline; 2-[[2-(4-fluorophenyl)quinazolin-4-yl]carbonyl]-5-methoxy-1,2,3,4-tetrahydroisoquinoline; 2-[[2-(4-fluorophenyl)quinazolin-4-yl]carbonyl]-6-methoxy-1,2,3,4-tetrahydroisoquinoline; 2-[[2-(4-fluorophenyl)quinazolin-4-yl]carbonyl]-5,7-dimethoxy-1,2,3,4-tetrahydroisoquinoline; 2-[[2-(4-fluorophenyl)quinazolin-4-yl]carbonyl]-5-hydroxy-1,2,3,4-tetrahydroisoquinoline; 2-[[2-(4-fluorophenyl)quinazolin-4-yl]carbonyl]-5-fluoro-1,2,3,4-tetrahydroisoquinoline; 2-[[2-(4-fluorophenyl)quinazolin-4-yl]carbonyl]-6-fluoro-1,2,3,4-tetrahydroisoquinoline; 2-[[2-(4-methylphenyl)quinazolin-4-yl]carbonyl]-5-hydroxy-6-methoxy-1,2,3,4-tetrahydroisoquinoline; 2-[[2-(4-methylphenyl)quinazolin-4-yl]carbonyl]-5,6-dihydroxy-1,2,3,4-tetrahydroisoquinoline; 2-[[2-(4-methylphenyl)quinazolin-4-yl]carbonyl]-5,6-dimethoxy-1,2,3,4-tetrahydroisoquinoline; 2-[[2-(4-methylphenyl)quinazolin-4-yl]carbonyl]-5-hydroxy-6-dimethylamino-1,2,3,4-tetrahydroisoquinoline; 2-[[2-(4-methylphenyl)quinazolin-4-yl]carbonyl]-5-hydroxy-6-methyl-1,2,3,4-tetrahydroisoquinoline; 2-[[2-phenylquinazolin-4-yl]carbonyl]-5-hydroxy-6-methoxy-1,2,3,4-tetrahydroisoquinoline; 2-[[2-phenylquinazolin-4-yl]carbonyl]-5,6-dihydroxy-1,2,3,4-tetrahydroisoquinoline; 2-[[2-phenylquinazolin-4-yl]carbonyl]-5,6-dimethoxy-1,2,3,4-tetrahydroisoquinoline; 2-[[2-phenylquinazolin-4-yl]carbonyl]-5-hydroxy-6-dimethylamino-1,2,3,4-tetrahydroisoquinoline; 2-[[2-phenylquinazolin-4-yl]carbonyl]-5-hydroxy-6-methyl-1,2,3,4-tetrahydroisoquinoline; 2-[[2-(4-methoxyphenyl)quinazolin-4-yl]carbonyl]-5-hydroxy-6-methoxy-1,2, 3,4-tetrahydroisoquinoline; 2-[[2-(4-methoxylphenyl)quinazolin-4-yl]carbonyl]-5,6-dihydroxy-1,2,3,4-tetrahydroisoquinoline; 2-[[2-(4-methoxylphenyl)quinazolin-4-yl]carbonyl]-5,6-dimethoxy-1,2,3,4-tetrahydroisoquinoline; 2-[[2-(4-methoxylphenyl)quinazolin-4-yl]carbonyl]-5-hydroxy-6-dimethylamino-1,2,3,4-tetrahydroisoquinoline; 2-[[2-(4-methoxylphenyl)quinazolin-4-yl]carbonyl]-5-hydroxy-6-methyl-1,2,3,4-tetrahydroisoquinoline; 2-[[2-(4-chlorophenyl)quinazolin-4-yl]carbonyl]-5-hydroxy-6-methoxy-1,2,3,4-tetrahydroisoquinoline; 2-[[2-(4-chlorophenyl)quinazolin-4-yl]carbonyl]-5,6-dihydroxy-1,2,3,4-tetrahydroisoquinoline; 2-[[2-(4-chlorophenyl)quinazolin-4-yl]carbonyl]-5,6-dimethoxy-1,2,3,4-tetrahydroisoquinoline; 2-[[2-(4-chlorophenyl)quinazolin-4-yl]carbonyl]-5-hydroxy-6-dimethylamino-1,2,3,4-tetrahydroisoquinoline; 2-[[2-(4-chlorophenyl)quinazolin-4-yl]carbonyl]-5-hydroxy-6-methyl-1,2,3,4-tetrahydroisoquinoline; 2-[[2-(4-(dimethylamino)phenyl)quinazolin-4-yl]carbonyl]-5-hydroxy-6-methoxy-1,2,3,4-tetrahydroisoquinoline; 2-[[2-(4-(dimethylamino)phenyl)quinazolin-4-yl]carbonyl]-5,6-dihydroxy-1,2,3,4-tetrahydroisoquinoline; 2-[[2-(4-(dimethylamino)phenyl)quinazolin-4-yl]carbonyl]-5,6-dimethoxy-1,2,3,4-tetrahydroisoquinoline; 2-[[2-(4-(dimethylamino)phenyl)quinazolin-4-yl]carbonyl]-5-hydroxy-6-dimethylamino-1,2,3,4-tetrahydroisoquinoline; 2-[[2-(4-(dimethylamino)phenyl)quinazolin-4-yl]carbonyl]-5-hydroxy-6-methyl-1,2,3,4-tetrahydroisoquinoline; 2-[[2-(4-(trifluoromethyl)phenyl)quinazolin-4-yl]carbonyl]-5-hydroxy-6-methoxy-1,2,3,4-tetrahydroisoquinoline; 2-[[2-(4-(trifluoromethyl)phenyl)quinazolin-4-yl]carbonyl]-5,6-dihydroxy-1,2,3,4-tetrahydroisoquinoline; 2-[[2-(4-(trifluoromethyl)phenyl)quinazolin-4-yl]carbonyl]-5,6-dimethoxy-1,2,3,4-tetrahydroisoquinoline; 2-[[2-(4-(trifluoromethyl)phenyl)quinazolin-4-yl]carbonyl]-5-hydroxy-6-dimethylamino-1,2,3,4-tetrahydroisoquinoline; 2-[[2-(4-(trifluoromethyl)phenyl)quinazolin-4-yl]carbonyl]-5-hydroxy-6-methyl-1,2,3,4-tetrahydroisoquinoline; 2-[[2-(3-fluorophenyl)quinazolin-4-yl]carbonyl]-5-hydroxy-6-methoxy-1,2,3,4-tetrahydroisoquinoline; 2-[[2-(3-fluorophenyl)quinazolin-4-yl]carbonyl]-5,6-dihydroxy-1,2,3,4-tetrahydroisoquinoline; 2-[[2-(3-fluorophenyl)quinazolin-4-yl]carbonyl]-5,6-dimethoxy-1,2,3,4-tetrahydroisoquinoline; 2-[[2-(3-fluorophenyl)quinazolin-4-yl]carbonyl]-5-hydroxy-6-dimethylamino-1,2,3,4-tetrahydroisoquinoline; 2-[[2-(3-fluorophenyl)phenyl)quinazolin-4-yl]carbonyl]-5-hydroxy-6-methyl-1,2,3,4-tetrahydroisoquinoline; 2-[[2-(3-methoxylphenyl)quinazolin-4-yl]carbonyl]-5-hydroxy-6-methoxy-1,2,3,4-tetrahydroisoquinoline; 2-[[2-(3-methoxylphenyl)quinazolin-4-yl]carbonyl]-5,6-dihydroxy-1,2,3,4-tetrahydroisoquinoline; 2-[[2-(3-methoxylphenyl)quinazolin-4-yl]carbonyl]-5,6-dimethoxy-1,2,3,4-tetrahydroisoquinoline; 2-[[2-(3-methoxylphenyl)quinazolin-4-yl]carbonyl]-5-hydroxy-6-dimethylamino-1,2,3,4-tetrahydroisoquinoline; 2-[[2-(3-methoxylphenyl)phenyl)quinazolin-4-yl]carbonyl]-5-hydroxy-6-methyl-1,2,3,4-tetrahydroisoquinoline; 2-[[2-(3-(trifluoromethyl)phenyl)quinazolin-4-yl]carbonyl]-5-hydroxy-6-methoxy-1,2,3,4-tetrahydroisoquinoline; 2-[[2-(3-(trifluoromethyl)phenyl)quinazolin-4-yl]carbonyl]-5,6-dihydroxy-1,2,3,4-tetrahydroisoquinoline; 2-[[2-(3-(trifluoromethyl)phenyl)quinazolin-4-yl]carbonyl]-5,6-dimethoxy-1,2,3,4-tetrahydroisoquinoline; 2-[[2-(3-(trifluoromethyl)phenyl)quinazolin-4-yl]carbonyl]-5-hydroxy-6-dimethylamino-1,2,3,4-tetrahydroisoquinoline; 2-[[2-(3-(trifluoromethyl)phenyl)quinazolin-4-yl]carbonyl]-5-hydroxy-6-methyl-1,2,3,4-tetrahydroisoquinoline; 2-[[2-(2,4-difluorophenyl)quinazolin-4-yl]carbonyl]-5-hydroxy-6-methoxy-1,2,3,4-tetrahydroisoquinoline; 2-[[2-(2,4-difluorophenyl)quinazolin-4-yl]carbonyl]-5,6-dihydroxy-1,2,3,4-tetrahydroisoquinoline; 2-[[2-(2,4-difluorophenyl)quinazolin-4-yl]carbonyl]-5,6-dimethoxy-1,2,3,4-tetrahydroisoquinoline; 2-[[2-(2,4-difluorophenyl)quinazolin-4-yl]carbonyl]-5-hydroxy-6-dimethylamino-1,2,3,4-tetrahydroisoquinoline; 2-[[2-(2,4-difluorophenyl)quinazolin-4-yl]carbonyl]-5-hydroxy-6-methyl-1,2,3,4-tetrahydroisoquinoline; 2-[[2-(4-acetamidophenyl)quinazolin-4-yl]carbonyl]-5-hydroxy-6-methoxy-1,2,3,4-tetrahydroisoquinoline; 2-[[2-(4-acetamidophenyl)quinazolin-4-yl]carbonyl]-5,6-dimethoxy-1,2,3,4-tetrahydroisoquinoline; 2-[[2-(4-acetamidophenyl)quinazolin-4-yl]carbonyl]-5-hydroxy-6-methyl-1,2,3,4-tetrahydroisoquinoline; 2-[[2-(4-(acetamidomethyl)phenyl)quinazolin-4-yl]carbonyl]-5-hydroxy-6-methoxy-1,2,3,4-tetrahydroisoquinoline; 2-[[2-(4-(acetamidomethyl)phenyl)quinazolin-4-yl]carbonyl]-5,6-dihydroxy-1,2,3,4-tetrahydroisoquinoline; 2-[[2-(4-(acetamidomethyl)phenyl)quinazolin-4-yl]carbonyl]-5,6-dimethoxy-1,2,3,4-tetrahydroisoquinoline; 2-[[2-(4-(acetamidomethyl)phenyl)quinazolin-4-yl]carbonyl]-5-hydroxy-6-dimethylamino-1,2,3,4-tetrahydroisoquinoline; 2-[[2-(4-(acetamidomethyl)phenyl)quinazolin-4-yl]carbonyl]-5-hydroxy-6-methyl-1,2,3,4-tetrahydroisoquinoline; 2-[[2-(4-pyrimidinyl)quinazolin-4-yl]carbonyl]-5-hydroxy-6-methoxy-1,2,3,4-tetrahydroisoquinoline; 2-[[2-(4-pyrimidinyl)quinazolin-4-yl]carbonyl]-5,6-dihydroxy-1,2,3,4-tetrahydroisoquinoline; 2-[[2-(4-pyrimidinyl)quinazolin-4-yl]carbonyl]-5,6-dimethoxy-1,2,3,4-tetrahydroisoquinoline; 2-[[2-(4-pyrimidinyl)quinazolin-4-yl]carbonyl]-5-hydroxy-6-methyl-1,2,3,4-tetrahydroisoquinoline; 2-[[2-(2-(acetamido)ethyl)quinazolin-4-yl]carbonyl]-5-hydroxy-6-methoxy-1,2,3,4-tetrahydroisoquinoline; 2-[[2-(2-(acetamido)ethyl)quinazolin-4-yl]carbonyl]-5,6-dihydroxy-1,2,3,4-tetrahydroisoquinoline; 2-[[2-(2-(acetamido)ethyl)quinazolin-4-yl]carbonyl]-5,6-dimethoxy-1,2,3,4-tetrahydroisoquinoline; 2-[[2-(2-(acetamido)ethyl)quinazolin-4-yl]carbonyl]-5-hydroxy-6-dimethylamino-1,2,3,4-tetrahydroisoquinoline; 2-[[2-(2-(acetamido)ethyl)quinazolin-4-yl]carbonyl]-5-hydroxy-6-methyl-1,2,3,4-tetrahydroisoquinoline; 2-[[2-(4-thiazolyl)quinazolin-4-yl]carbonyl]-5-hydroxy-6-methoxy-1,2,3,4-tetrahydroisoquinoline; 2-[[2-(4-thiazolyl)quinazolin-4-yl]carbonyl]-5,6-dihydroxy-1,2,3,4-tetrahydroisoquinoline; 2-[[2-(4-thiazolyl)quinazolin-4-yl]carbonyl]-5,6-dimethoxy-1,2,3,4-tetrahydroisoquinoline; 2-[[2-(4-thiazolyl)quinazolin-4-yl]carbonyl]-5-hydroxy-6-dimethylamino-1,2,3,4-tetrahydroisoquinoline; 2-[[2-(4-thiazolyl)quinazolin-4-yl]carbonyl]-5-hydroxy-6-methyl-1,2,3,4-tetrahydroisoquinoline; 2-[[2-(3-pyridinyl)quinazolin-4-yl]carbonyl]-5-hydroxy-6-methoxy-1,2,3,4-tetrahydroisoquinoline; 2-[[2-(3-pyridinyl)quinazolin-4-yl]carbonyl]-5,6-dihydroxy-1,2,3,4-tetrahydroisoquinoline; 2-[[2-(3-pyridinyl)quinazolin-4-yl]carbonyl]-5,6-dimethoxy-1,2,3,4-tetrahydroisoquinoline; 2-[[2-(3-pyridinyl)quinazolin-4-yl]carbonyl]-5-hydroxy-6-dimethylamino-1,2,3,4-tetrahydroisoquinoline; 2-[[2-(3-pyridinyl)quinazolin-4-yl]carbonyl]-5-hydroxy-6-methyl-1,2,3,4-tetrahydroisoquinoline; 2-[[2-(3,4,5-trimethoxyphenyl)quinazolin-4-yl]carbonyl]-5-hydroxy-6-methoxy-1,2,3,4-tetrahydroisoquinoline; 2-[[2-(3,4,5- trimethoxyphenyl)quinazolin-4-yl]carbonyl]-5-methoxy-1,2,3,4-tetrahydroisoquinoline; 2-[[2-(3,4,5-trimethoxyphenyl)quinazolin-4-yl]carbonyl]-6-methoxy-1,2,3,4-tetrahydroisoquinoline; 2-[[2-(3,4,5-trimethoxyphenyl)quinazolin-4-yl]carbonyl]-5,7-dimethoxy-1,2,3,4-tetrahydroisoquinoline; 2-[[2-(3,4,5-trimethoxyphenyl)quinazolin-4-yl]carbonyl]-5-hydroxy-1,2,3,4-tetrahydroisoquinoline; 2-[[2-(3,4,5-trimethoxyphenyl)quinazolin-4-yl]carbonyl]-6-fluoro-1,2,3,4-tetrahydroisoquinoline; 2-[[2-(4-nitrophenyl)quinazolin-4-yl]carbonyl]-5-hydroxy-6-methoxy-1,2,3,4-tetrahydroisoquinoline; 2-[[2-(4-aminophenyl)quinazolin-4-yl]carbonyl]-5-hydroxy-6-methoxy-1,2,3,4-tetrahydroisoquinoline; 2-[[6-fluoro-2-(4-fluorophenyl)quinazolin-4-yl]carbonyl]-5-hydroxy-6-methoxy-1,2,3,4-tetrahydroisoquinoline; 2-[[6-fluoro-2-(4-fluorophenyl)quinazolin-4-yl]carbonyl]-5-methoxy-1,2,3,4-tetrahydroisoquinoline; 2-[[6-fluoro-2-(4-fluorophenyl)quinazolin-4-yl]carbonyl]-6-methoxy-1,2,3,4-tetrahydroisoquinoline; 2-[[6-fluoro-2-(4-fluorophenyl)quinazolin-4-yl]carbonyl]-5,7-dimethoxy-1,2,3,4-tetrahydroisoquinoline; 2-[[6-fluoro-2-(4-fluorophenyl)quinazolin-4-yl]carbonyl]-5-hydroxy-1,2,3,4-tetrahydroisoquinoline; 2-[[6-fluoro-2-(4-fluorophenyl)quinazolin-4-yl]carbonyl]-6-fluoro-1,2,3,4-tetrahydroisoquinoline; 2-[[6-fluoro-2-(3,4,5-trimethoxyphenyl)quinazolin-4-yl]carbonyl]-5-hydroxy-6-methoxy-1,2,3,4-tetrahydroisoquinoline; 2-[[6-fluoro-2-(3,4,5-trimethoxyphenyl)quinazolin-4-yl]carbonyl]-5-methoxy-1,2,3,4-tetrahydroisoquinoline; 2-[[6-fluoro-2-(3,4,5-trimethoxyphenyl)quinazolin-4-yl]carbonyl]-6-methoxy-1,2,3,4-tetrahydroisoquinoline; 2-[[6-fluoro-2-(3,4,5-trimethoxyphenyl)quinazolin-4-yl]carbonyl]-5,7-dimethoxy-1,2,3,4-tetrahydroisoquinoline; 2-[[6-fluoro-2-(3,4,5-trimethoxyphenyl)quinazolin-4-yl]carbonyl]-5-hydroxy-1,2,3,4-tetrahydroisoquinoline; 2-[[6-fluoro-2-(3,4,5-trimethoxyphenyl)quinazolin-4-yl]carbonyl]-6-fluoro-1,2,3,4-tetrahydroisoquinoline; 2-[[6,7-dimethoxy-2-(4-fluorophenyl)quinazolin-4-yl]carbonyl]-5-hydroxy-6-methoxy-1,2,3,4-tetrahydroisoquinoline; 2-[[6,7-dimethoxy-2-(4-fluorophenyl)quinazolin-4-yl]carbonyl]-5-methoxy-1,2,3,4-tetrahydroisoquinoline; 2-[[6,7-dimethoxy-2-(4-fluorophenyl)quinazolin-4-yl]carbonyl]-6-methoxy-1,2,3,4-tetrahydroisoquinoline; 2-[[6,7-dimethoxy-2-(4-fluorophenyl)quinazolin-4-yl]carbonyl]-5,7-dimethoxy-1,2,3,4-tetrahydroisoquinoline; 2-[[6,7-dimethoxy-2-(4-fluorophenyl)quinazolin-4-yl]carbonyl]-5-hydroxy-1,2,3,4-tetrahydroisoquinoline; 2-[[6,7-dimethoxy-2-(4-fluorophenyl)quinazolin-4-yl]carbonyl]-6-fluoro-1,2,3,4-tetrahydroisoquinoline; 2-[[6,7-dimethoxy-2-(3,4,5-trimethoxyphenyl)quinazolin-4-yl]carbonyl]-5-hydroxy-6-methoxy-1,2,3,4-tetrahydroisoquinoline; 2-[[6,7-dimethoxy-2-(3,4,5-trimethoxyphenyl)quinazolin-4-yl]carbonyl]-5-methoxy-1,2,3,4-tetrahydroisoquinoline; 2-[[6,7-dimethoxy-2-(3,4,5-trimethoxyphenyl)quinazolin-4-yl]carbonyl]-6-methoxy-1,2,3,4-tetrahydroisoquinoline; 2-[[6,7-dimethoxy-2-(3,4,5-trimethoxyphenyl)quinazolin-4-yl]carbonyl]-5,7-dimethoxy-1,2,3,4-tetrahydroisoquinoline; 2-[[6,7-dimethoxy-2-(3,4,5-trimethoxyphenyl)quinazolin-4-yl]carbonyl]-5-hydroxy-1,2,3,4-tetrahydroisoquinoline; and 2-[[6,7-dimethoxy-2-(3,4,5-trimethoxyphenyl)quinazolin-4-yl]carbonyl]-6-fluoro-1,2,3,4-tetrahydroisoquinoline; or a pharmaceutically acceptable salt thereof.

17. A compound of claim 1, wherein the compound of formula (I) is covalently bonded to a cell-specific targeting moiety, or a pharmaceutically acceptable salt thereof.

18. A pharmaceutical composition comprising a compound of claim 1, or a pharmaceutically acceptable salt thereof, and a pharmaceutically acceptable carrier.

19. A method of making a compound of formula (I), comprising:

contacting a compound of formula (IV):

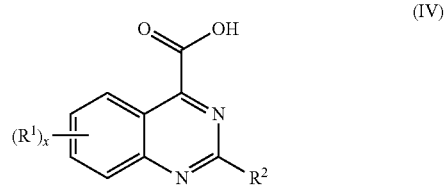

(IV)

wherein:

each $R^1$, independently, is hydrogen, halogen, or —O—$R^4$;

$R^2$ is —$(CR^aR^b)_z$—$R^5$;

each $R^a$, independently, is hydrogen, halogen, hydroxy, alkyl, alkoxy, alkenyl, alkynyl, cycloalkyl, heterocyclyl, aryl, or heteroaryl;

each $R^b$, independently, is hydrogen, halogen, hydroxy, alkyl, alkoxy, alkenyl, alkynyl, cycloalkyl, heterocyclyl, aryl, or heteroaryl;

each $R^4$, independently, is hydrogen or $C_1$-$C_6$ alkyl;

$R^5$ is hydrogen, halo, alkyl, hydroxy, alkyl, alkoxy, alkenyl, alkynyl, cycloalkyl, heterocyclyl, —N($R^4$)CO—$R^4$ or Ar;

Ar is aryl or heteroaryl, wherein each of aryl and heteroaryl is optionally substituted by one to five substituents independently selected from hydrogen, halogen, —$R^4$, —N($R^4$)$_2$, nitro, —$(CH_2)_n$—NHCO—$R^4$, —O—$R^4$, alkyl, alkenyl, alkynyl, cycloalkyl, heterocyclyl, aryl, or heteroaryl;

n is 0, 1, 2, or 3;

x is 0, 1, 2, 3, or 4; and z is 0, 1, 2, 3, 4, 5, or 6;

with a compound of formula (IIIa):

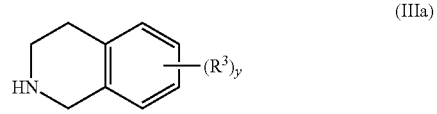

(IIIa)

wherein:

each $R^3$, independently, is hydrogen, halogen, —N($R^4$)$_2$, —O—$R^4$, alkyl, alkoxy, alkenyl, alkynyl, cycloalkyl, heterocyclyl, aryl, or heteroaryl;

each $R^4$, independently, is hydrogen or $C_1$-$C_6$ alkyl; and y is 0, 1, 2, 3, or 4.

20. The method of claim 19, wherein $R^2$ is —$(CR^aR^b)_z$—N($R^4$)CO—$R^4$, or Ar.

* * * * *